(12) United States Patent
Pandey et al.

(10) Patent No.: US 9,533,986 B2
(45) Date of Patent: Jan. 3, 2017

(54) BICYCLIC DIHYDROPYRIDONE KINASE INHIBITORS

(71) Applicant: PORTOLA PHARMACEUTICALS, INC., South San Francisco, CA (US)

(72) Inventors: Anjali Pandey, Fremont, CA (US); Yonghong Song, Foster City, CA (US); Qing Xu, Foster City, CA (US)

(73) Assignee: PORTOLA PHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 14/432,146

(22) PCT Filed: Sep. 27, 2013

(86) PCT No.: PCT/US2013/000224
§ 371 (c)(1),
(2) Date: Mar. 27, 2015

(87) PCT Pub. No.: WO2014/051653
PCT Pub. Date: Apr. 3, 2014

(65) Prior Publication Data
US 2015/0266871 A1 Sep. 24, 2015

Related U.S. Application Data

(60) Provisional application No. 61/706,681, filed on Sep. 27, 2012.

(51) Int. Cl.
| | | |
|---|---|---|
| *A61K 31/519* | (2006.01) | |
| *C07D 471/04* | (2006.01) | |
| *C07D 217/24* | (2006.01) | |
| *C07D 401/12* | (2006.01) | |
| *C07D 401/04* | (2006.01) | |

(52) U.S. Cl.
CPC ........... *C07D 471/04* (2013.01); *C07D 217/24* (2013.01); *C07D 401/04* (2013.01); *C07D 401/12* (2013.01)

(58) Field of Classification Search
CPC .................................................. C07D 471/04
See application file for complete search history.

(56) References Cited

U.S. PATENT DOCUMENTS

| | | |
|---|---|---|
| 2011/0053897 A1 | 3/2011 | Che et al. |
| 2012/0142671 A1 | 6/2012 | Jia et al. |
| 2012/0172448 A1 | 7/2012 | Lampe et al. |

FOREIGN PATENT DOCUMENTS

| | | |
|---|---|---|
| WO | 2008/123755 A1 | 10/2008 |
| WO | 2010/105179 A2 | 9/2010 |
| WO | 2012/085167 A1 | 6/2012 |
| WO | 2014/051653 | 4/2014 |

OTHER PUBLICATIONS

Berge, S.M. et al., "Pharmaceutical Salts," Journal of Pharmaceutical Science, 66:1-19, 1977.
Braselmann et al., "R406, an Orally Available Spleen Tyrosine Kinase Inhibitor Blocks Fc Receptor Signaling and Reduces Immune Complex-Mediated Inflammation," J Pharmacol Exp Ther 319(3): 998-1008 (2006).
Burnett and Knapper, "Targenting Treatment in AML," Hematology Am Soc Hematol Educ Program 2007: 429-34 (2007).
Chen, L., et.al, "Protein tyrosine phosphatase receptor—type O truncated (PTPROt) regulates SYK phosphorylation, proximal B-cell—receptor signaling, and cellular proliferation," Blood, 2006; 108:3428-3433.
Chen, Monti et al., "SYK-dependent tonic B-cell receptor signaling is a rational treatment target in diffuse large B-cell lymphoma," Blood 111(4): 2230-7 (2008).
Chen, R. et al., "MicroRNA regulation in mantle cell lymphoma," Journal of Clinical Oncology, 2007 ASCO Annual Meeting Proceedings (Post-Meeting Edition).vol. 25, No. 18S (Jun. 20 Supplement), 2007: 8056.
Cheng, Alec et al., "SYK tyrosine kinase required formouse viability and B-cell development," Nature 378(6554):303-6 (1995).
Couture, C. et al., "Activation of p56lck by p72,k through Physical Association and N-Terminal Tyrosine Phosphorylationt," Mol. Cell. Biol., 14:5249-5258, 1994.
Couture, C. et al., "p56lck-independent activation and tyrosine phosphorylation of p72sYk by T-cell antigen receptor/CD3 stimulation," Proc. Natl. Acad. Sci. USA, 91:5301-5305, 1994.
Crow, A.R. et al., "Inhibition of Immune Thrombocytopenic Purpura (ITP) by an Orally Bioavailabl Inhibitor of Syk Kinase Activity," Blood, 106:abstract 2165, 2005.
Crowley, M.T. et al., "A Critical Role for Syk in Signal Transduction and Phagocytosis Mediated by Fc g Receptors on Macrophages," J. Exp. Med., 186:1027-1039, 1997.
Friedberg, JW et al, "Inhibition of Syk with fostamatinib disodium has significant clinical activity in non-Hodgkin lymphoma and chronic lymphocytic leukemia," Blood 2010; 115(13), 2578-2585.
Garcia-Bustos et al., "PIK1, an essential phosphatidylinositol 4-kinase associated with the yeast nucleus," (1994), EMBO J. 13:2352-2361.
Gobessi et al., "Constitutive activation of the protein tyrosine kinase Syk in Chronic Lymphocytic Leukemia B-cells", *Blood* (ASH Annual Meeting Abstracts) 2007 110: Abstract 1123.
Gururajan et al., "Cutting Edge: Constitutive B Cell Receptor Signaling is Critical for Basal Growth of B Lymphoma," 2006, 176:5715-5719.
Gururajan et al., "Spleen Tyrosine Kinase (Syk), a Novel Target of Curcumin, Is Required for B Lymphoma Growth," J Immunol 178(1): 111-21 (2007).

(Continued)

*Primary Examiner* — Brian McDowell
(74) *Attorney, Agent, or Firm* — Mintz, Levin, Cohn, Ferris, Glovsky and Popeo, P.C.

(57) ABSTRACT

Provided are bicyclic dihydropyridone compounds for inhibiting of JAK/Syk kinase, intermediates used in making such compounds, methods for their preparation, pharmaceutical compositions thereof, methods for inhibiting JAK/Syk kinase activity, and methods for treating conditions mediated at least in part by JAK/Syk kinase activity.

18 Claims, 8 Drawing Sheets

(56) References Cited

OTHER PUBLICATIONS

Hanks & Hunter, "The eukaryotic protein kinase superfamily: kinase (catalytic) domain structure and classification," (1995), FASEB J. 9:576-596.
Heinrich, Griffith et al., "Inhibition of c-kit receptor tyrosine kinase activity by STI 571, a selective tyrosine kinase inhibitor," Blood 96(3): 925-32 (2000).
Hiles et al., "Phosphatidylinositol 3-Kinase: Structure and Expression of the 110 kd Catalytic Subunit," (1992), Cell 70:419-429.
Hutchcroft, J E. et al., "Association of the 72-kDa Protein-tyrosine Kinase PTK72 with the B Cell Antigen Receptor," J. Biol. Chem., 267:8613-8619, 1992.
Irish et al., "Altered B-cell receptor signaling kinetics distinguish human follicular lymphoma B cells from tumor-infiltrating nonmalignant B cells," Blood, 2006; 108: 3135-3142.
Jumaa, Hendriks et al., "B cell signaling and tumorigenesis," Annu Rev Immunol 23: 415-45 (2005).
Knighton et al., "Crystal structure of the catalytic subunit of cyclic adenosine monophosphate-dependent protein kinase," (1991), Science 253:407-414.
Kraus et al., "Survival of Resting Mature B Lymphocytes Depends on BCR Signaling via the Iga/β Heterodimer," Cell 117(6): 787-800 (2004).
Kuno, Y. et.al., "Constitutive kinase activation of the *TEL-Syk* fusion gene in myelodysplastic syndrome with t(9;12)(q22;p12)," Blood, 2001; 97:1050-1055.
Kunz et al., "Target of Rapamycin in Yeast, TOR2, Is an Essential Phosphatidylinositol Kinase Homolog Required for G1 Progression," (1993), Cell 73:585-596.
Kuppers, R., "Mechanisms of B-Cell Lymphoma Pathogenesis," Nat Rev Cancer, 2005; 5:251-262.
Lam, Kuhn et al., "In Vivo Ablation of Surface Immunoglobulin on Mature B Cells by Inducible Gene Targeting Results in Rapid Cell Death," Cell 90(6): 1073-83 (1997).
LaTour, S. et al., "Regulation of T-Cell Antigen Receptor Signalling by Syk Tyrosine Protein Kinase," Mol Cell Biol., 17:4434-4441, 1997.
Law, D.A. et al., "Genetic and Pharmacological Analyses of Syk Function in allbb3 Signaling in Platelets," Blood, 93:2645-2652, 1999.
LeSeux, L. et. al., "Syk-dependent mTOR activation in follicular lymphoma cells," Blood, 2006; 108:4156-4162.
Linfeng, Chen et al., "SYK-dependent tonic B-cell receptor signaling is a rational treatment target in diffuse large B-cell lymphoma," *Blood*, Feb. 2008; 111: 2230-2237.
Poole, A. et al., "The Fc receptor g-chain and the tyrosine kinase Syk are essential for activation of mouse platelets by collagen," EMBO J., 16:2333-2341, 1997.
Reilly, M.P., "Heparin-induced thrombocytopenia/thrombosis in a transgenic mouse model requires human platelet factor 4 and platelet activation through FcgRIIA," Blood, 98:2442-2447, 2001.
Rinaldi, A. et.al, "Genomic and expression profiling identifies the B-cell associated tyrosine kinase Syk as a possible therapeutic target in mantle cell lymphoma," Br. J. Haematol., 2006; 132:303-316.
Rolli, Gallwitz et al. "Amplification of B Cell Antigen Receptor Signaling by a Syk/ITAM Positive Feedback Loop," Mol Cell 10(5): 1057-69 (2002).
Rossi, A.B. et al., "Identification of the Syk kinase inhibitor R112 by a human mast cell screen," J Allergy Clin Immunol., 118:749-755, 2006.
Takata, M. et al., "Tyrosine kinases Lyn and Syk regulate B cell receptorcoupled Ca2+ mobilization through distinct pathways," EMBO J., 13:1341-1349, 1994.
Underhill, D.M and Goodridge, H. S., "The many faces of ITAMs," *Trends Immunol.*, 28:66-73, 2007.
Wossning, T. et al., "Deregulated Syk inhibits differentiation and induces growth factor—independent proliferation of pre—B cells," JEM, 2006; 203:2829-2840.
Yousefi, S. et al., "Requirement of Lyn and Syk Tyrosine Kinases for the Prevention of Apoptosis by Cytokinesin Human Eosinophils," J. E. Med., 183:1407-1414, 1996.

BICYCLIC DIHYDROPYRIDONE KINASE INHIBITORS

CROSS REFERENCE TO RELATED APPLICATIONS

This application claims the benefit of U.S. Provisional Patent Application No. 61/706,681, filed Sep. 27, 2012; the entire disclosure of which is incorporated herein by reference.

BACKGROUND OF THE INVENTION

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease and hormone-related diseases. As a consequence, there has been substantial efforts in medicinal chemistry to find inhibitors of protein kinases for use as therapeutic agents.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, Fc receptors in immune cells and at GPVI and FcγRIIa in platelets to downstream intracellular molecules such as Syk and ZAP-70 (Underhill, D. M and Goodridge, H. S., *Trends Immunol.*, 28:66-73, 2007).

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact.

Syk, along with Zap-70, is a member of the Syk family of protein tyrosine kinases. The interaction of Syk or ZAP-70 with diphosphorylated ITAM sequences induces a conformation change in the kinases that allows for tyrosine phosphorylation of the kinase itself. Phosphorylated Syk family members activate a multitude of downstream signaling pathway proteins which include Src homology 2 (SH2) domain containing leukocyte-specific phosphoprotein of 76 kDa (SLP-76), Linker of Activation of T-cells (LAT) and PLC (phospholipase C)γ2.

Human pathologies attributed to dysfunctional ITAM-mediated signaling include autoimmune diseases such as rheumatoid arthritis, systemic lupus, multiple sclerosis, hemolytic anemia, immune-thrombocytopenia purpura, and heparin-induced thrombocytopenia and arteriosclerosis. Interestingly, many of the above mentioned diseases are thought to occur through crosslinking of Fc receptors by antibodies which, via Syk, activate a signaling cascade in mast, basophil and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the tyrosine kinase activity of Syk (Rossi, A. B. et al., *J Allergy Clin Immunol.*, 118:749-755, 2006). In immune-thrombocytopenia, antibody bound platelets are cleared by the spleen by an Fc receptor/ITAM/Syk-mediated process (Crow, A. R. et al., *Blood*, 106:abstract 2165, 2005). Drug-induced thrombocytopenia, caused by heparin-platelet factor 4 immune complexes that activate platelet FcγRIIa, also involve Syk signaling downstream of receptor engagement (Reilly, M. P., *Blood*, 98:2442-2447, 2001).

Platelet agonists induce inside-out integrin signaling resulting in fibrinogen binding and platelet aggregation. This initiates outside-in signaling which produces further stimulation of platelets. Syk is activated during both phases of integrin signaling, and inhibition of Syk is shown to inhibit platelet adhesion to immobilized proteins (Law, D. A. et al., *Blood*, 93:2645-2652, 1999). Release of arachidonic acid and serotonin and platelet aggregation induced by collagen are markedly inhibited in platelets derived from Syk deficient mouse (Poole, A. et al., *EMBO J.*, 16:2333-2341, 1997). Thus Syk inhibitors may also possess anticoagulation action.

Because of the role Syk plays in Ig-induced platelet activation, it is likely to be important in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). For example, restenosis of an atherosclerotic coronary artery after PTCA (Percutaeous Transluminal Coronary Angioplasty) occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

In addition to the role Syk plays in Ig-induced platelet activations, Syk plays a very important role in collagen-mediated signaling. The primary adhesive protein responsible for platelet adhesion and activation is collagen. Collagen is a filamentous protein contained within the fibrotic caps of atheromas which becomes exposed to blood during plaque rupture. Collagen functions initially by binding von Willebrand factor which tethers platelets through binding platelet membrane GPIb. Collagen functions secondarily by engaging the two collagen receptors on platelets, GPVI and integrin $\alpha 2\beta 1$.

GPVI exists in platelet membranes as a complex with FcR$\gamma$, an interaction required for the expression of GPVI. Activation of Fc$\gamma$RIIa on platelets results in platelet shape change, secretion and thrombosis. Signaling by the GPVI/FcR$\gamma$ complex is initiated by tyrosine phosphorylation of the ITAM domain of FCR$\gamma$ followed by the recruitment of Syk. Activation of GPVI leads to induction of multiple platelet functions including: activation of integrins $\alpha 2\beta 1$ to achieve firm platelet adhesion, and GP IIb-IIIa which mediates platelet aggregation and thrombosis growth; platelet secretion, allowing for the delivery of inflammatory proteins such as CD40L, RANTES and TGF$\beta$ to the vessel wall; and the expression of P-selectin which allows for the recruitment of leukocytes. Therefore, it is believed that Syk inhibitors can inhibit thrombotic events mediated by platelet adhesion, activation and aggregation.

It has been reported that the tyrosine phosphorylation of intracellular protein (activation) induced by stimulation of a receptor for IgG antibody, Fc$\gamma$R, and the phagocytosis mediated by Fc$\gamma$R are considerably inhibited in macrophages derived from Syk deficient mouse (Crowley, M. T. et al., *J. Exp. Med.*, 186:1027-1039, 1997). This suggests that Syk has a markedly important role in the Fc$\gamma$R-mediated phagocytosis of macrophages.

It has also been reported that an antisense oligonucleotide of Syk suppresses the apoptosis inhibition of eosinophils induced by GM-CSF (Yousefi, S. et al., *J. E. Med.*, 183: 1407-1414, 1996), showing that Syk is essential for the life extending signal of eosinophils caused by GM-CSF and the like. Since life extension of eosinophils is closely related to the transition of diseases into a chronic state in allergic disorders, such as asthma, Syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., *J. Biol. Chem.*, 267:8613-8619, 1992; and Takata, M. et al., *EMBO J.*, 13:1341-1349, 1994). Thus, Syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., *Proc. Natl. Acad. Sci. USA*, 91:5301-5305, 1994; and Couture, C. et al., *Mol. Cell. Biol.*, 14:5249-5258, 1994). Syk is present in mature T-cell populations, such as intraepithelial $\gamma\delta$ T-cells and naïve $\alpha\beta$ T-cells, and has been reported to be capable of phosphorylation of multiple components of the TCR signaling cascade (Latour, S. et. al., *Mol Cell Biol.*, 17:4434-4441, 1997). As a consequence, Syk inhibitors may serve as agents for inhibiting cellular immunity mediated by T-cell antigen receptor.

Recent comparative genomic hybridization studies have identified Syk as another gene important in the pathogenesis of Mantle Cell Lymphoma (MCL) (Chen, R. et al. *Journal of Clinical Oncology*, 2007 ASCO Annual Meeting Proceedings (Post-Meeting Edition). Vol 25, No 18S (June 20 Supplement), 2007: 8056). MCL represents 5-10% of all non-Hodgkins lymphomas and it is a difficult form of lymphoma to treat. It has the worst prognosis among the B cell lymphomas with median survival of three years. It has been reported that Syk is overexpressed in MCL (Rinaldi, A, et. al, *Br. J. Haematol.*, 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L., et. al, Blood, 2006; 108:4156-4162).

Several lines of evidence suggest that many B-cell lymphomas depend upon B-cell receptor (BCR)-mediated survival signals. BCR signaling induces receptor oligomerization and phosphorylation of Ig$\alpha$ and $\beta$ immunoreceptor tyrosine-based activated motifs by SRC family kinases. ITAM phosphorylation results in the recruitment and activation of Syk that initiates downstream events and amplifies the original BCR signal. Given the role of tonic BCR signaling in normal B cell and Syk-dependent survival of non-Hodgkins lymphoma cell lines in vitro (Chen, L., et. al, *Blood*, 2006; 108:3428-3433), Syk inhibition is a promising rational treatment target for certain B-cell lymphomas and chronic lymphocytic leukemia (CLL) (Stefania Gobessi, Luca Laurenti, Pablo Longo, Laura Carsetti, Giuseppe Leone, Dimitar G. Efremov, Constitutive activation of the protein tyrosine kinase Syk in Chronic Lymphocytic Leukemia B-cells, Blood, 2007, 110, Abstract 1123). Recent data shows that administration of a multikinase inhibitor which inhibits Syk, may have significant clinical activity in CLL patients (Friedberg J W et al, Blood 2010; 115 (13),).

The oncogenic potential of the spleen tyrosine kinase (Syk) has been described in a number of different settings. Clinically, Syk over-expression is reported in Mantle Cell Lymphoma (Rinaldi, A, et al, *Br. J. Haematol.*, 2006; 132:303-316) and the TEL-Syk fusion protein (Translocated ETS Leukemia) generated by a chromosomal translocation (t(9; 12)(q22; p12)) leads to increased Syk activity and is associated with myelodysplastic syndrome (Kuno, Y., et. al, *Blood*, 2001; 97:1050-1055). Leukemia is induced in mice by adoptively transferring bone marrow cells that express human TEL-Syk (Wossning, T., JEM, 2006; 203:2829-2840). Further, in mouse primary bone marrow cells, overexpression of Syk results in IL-7 independent growth in culture (Wossning, T., et. al, JEM, 2006; 203:2829-2840). Additional recent studies also suggest that Syk-dependant survival signals may play a role in B-cell malignancies, including DLBCL (Diffuse Large B-Cell Lymphoma), mantle cell lymphoma and follicular lymphoma (Gururajan, Jennings et al. 2006; Irish, Czerwinski et al. J Immunol 176(10): 5715-9 (2006). Given the role of tonic BCR signaling in normal B cells and Syk-dependent survival of NHL cell lines in vitro, the specific inhibition of Syk may prove promising for the treatment of certain B-cell lymphomas.

Interestingly, Syk signaling appears to be required for B-cell development and survival in humans and mouse. Inducible loss of the B-cell receptor (Lam, K., et. al, Cell, 1997; 90:1073-1083) or Igα (Kraus, M., et. al, Cell, 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et. al, Blood, 2006; 108:3428-3433). Finally, B-cell lymphomas rarely exhibit loss of BCR expression, and anti-idiotype therapy rarely leads to resistance (Kuppers, R. Nat Rev Cancer, 2005; 5:251-262).

Engagement of the antigen-specific B cell receptor (BCR) activates multiple signaling pathways that ultimately regulate the cells activation status, promoting survival and clonal expansion. Signaling through the BCR is made possible by its association with two other members of the immunoglobulin super-family; Igα and Igβ, each bearing an immunotyrosine based activation motif (ITAM) (Jumaa, Hendriks et al. Annu Rev Immunol 23: 415-45 (2005). The ITAM domain is directly phosphorylated by Src family kinases in response to BCR engagement. The spleen tyrosine kinase (Syk) docks with and phosphorylates the ITAM, a process that enhances its kinase activity, resulting in Syk autophosphorylation and tyrosine phosphorylation of multiple downstream substrates (Rolli, Gallwitz et al. Mol Cell 10(5): 1057-69 (2002). This signaling pathway is active in B cells beginning at the transition from pro- to pre-B cell stage of development, when the newly formed pre-BCR is expressed. In fact, B cell development arrests at the pro-B cell stage in Syk knockout mice (Cheng, Rowley et al. 1995; Turner, Mee et al. Nature 378(6554): 303-6 (1995). Inducible loss of the B cell receptor (Lam, Kuhn et al. Cell 90(6): 1073-83 (1997) or Igα (Kraus, Alimzhanov et al. Cell 117(6): 787-800 (2004) results in loss of peripheral B cells in mice. Human B cells also appear to require Syk for proliferation and survival. Over-expression of the protein tyrosine phosphatase PTP-RO, a negative regulator of Syk activity, inhibits proliferation and induces apoptosis in cell lines derived from non-Hodgkin's lymphomas (NHL) (Chen, Juszczynski et al. Blood 108(10): 3428-33 (2006). Knock down of Syk by siRNA in the NHL line SUDHL-4 led to a block in the G1/S transition of the cell cycle (Gururajan, Dasu et al. J Immunol 178(1): 111-21 (2007). Together, these data suggest that Syk signaling is required for the development, proliferation, and even survival of human and mouse B cells.

Recently, R406 (Rigel Pharmaceuticals) was reported to inhibit ITAM signaling in response to various stimuli, including FcεR1 and BCR induced Syk activation (Braselmann, Taylor et al. J Pharmacol Exp Ther 319(3): 998-1008 (2006). Interestingly, this ATP-competitive inhibitor of Syk was also active against Flt3, cKit, and JAK kinases, but not against Src kinsase (Braselmann, Taylor et al. 2006). Activating mutations to Flt3 are associated with AML (Acute Myeloid Leukemia) and inhibition of this kinase is currently under clinical development (Burnett and Knapper Hematology Am Soc Hematol Educ Program 2007: 429-34 (2007). Over-activation of the tyrosine kinase cKit is also associated with hematologic malignancies, and a target for cancer therapy (Heinrich, Griffith et al. Blood 96(3): 925-32 (2000). Similarly, JAK3 signaling is implicated in leukemias and lymphomas, and is currently exploited as a potential therapeutic target (Heinrich, Griffith et al. 2000). Importantly, the multi-kinase inhibitory activity of R406 attenuates BCR signaling in lymphoma cell lines and primary human lymphoma samples, resulting in apoptosis of the former (Chen, Monti et al. Blood 111(4): 2230-7 (2008). Further, a phase II clinical trial reported favorable results by this compound in refractory NHL and chronic lymphocytic leukemia (Friedberg J W et al, Blood 2010; 115(13)). Although the precise mechanism of action is unclear for R406, the data suggest that inhibition of kinases that mediate survival signaling in lymphocytes is clinically beneficial.

Additional recent studies also suggest that Syk-dependant survival signals may play a role in B-cell malignancies, including DLBCL, mantle cell lymphoma and follicular lymphoma (see e.g., S. Linfengshen et al. Blood, February 2008; 111: 2230-2237; J. M. Irish et al. Blood, 2006; 108: 3135-3142; A. Renaldi et al. Brit J. Haematology, 2006; 132: 303-316; M. Guruoajan et al. J. Immunol, 2006; 176: 5715-5719; L. Laseux et al. Blood, 2006; 108: 4156-4162.

While progress has been made in this field, there remains a need in the art for compounds that inhibit Syk kinase, as well as for methods for treating conditions in a patient, such as restenosis, and/or inflammation that can benefit from such inhibition. Moreover, the availability of compounds that selectively inhibit one of these kinases as compared to other kinases would also be desirable. The present invention satisfies this and other needs.

BRIEF SUMMARY OF THE INVENTION

In one aspect, provided are compounds of Formula (I):

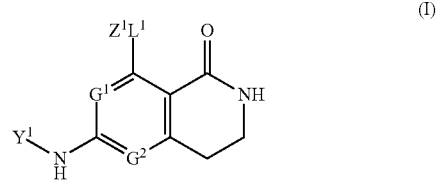

or a tautomer or a pharmaceutically acceptable salt thereof, wherein $Z^1L^1$, $G^1$, $G^2$, and $Y^1$ are described herein.

In another aspect, provided are pharmaceutical compositions comprising a therapeutically effective amount of one or more of such compounds, as well as methods for the use of the compounds in therapeutic applications. The compounds disclosed herein have utility over a wide range of therapeutic applications, and may be used to treat a variety of conditions such as those mediated at least in part by JAK or Syk kinase. For example, such conditions include, but are not limited to, those associated with cardiovascular disease, inflammatory disease, autoimmune disease, or a cell proliferative disorder.

These and other aspects and features of the invention will be apparent upon reference to the following detailed description.

DETAILED DESCRIPTION OF THE INVENTION

Figure 1:
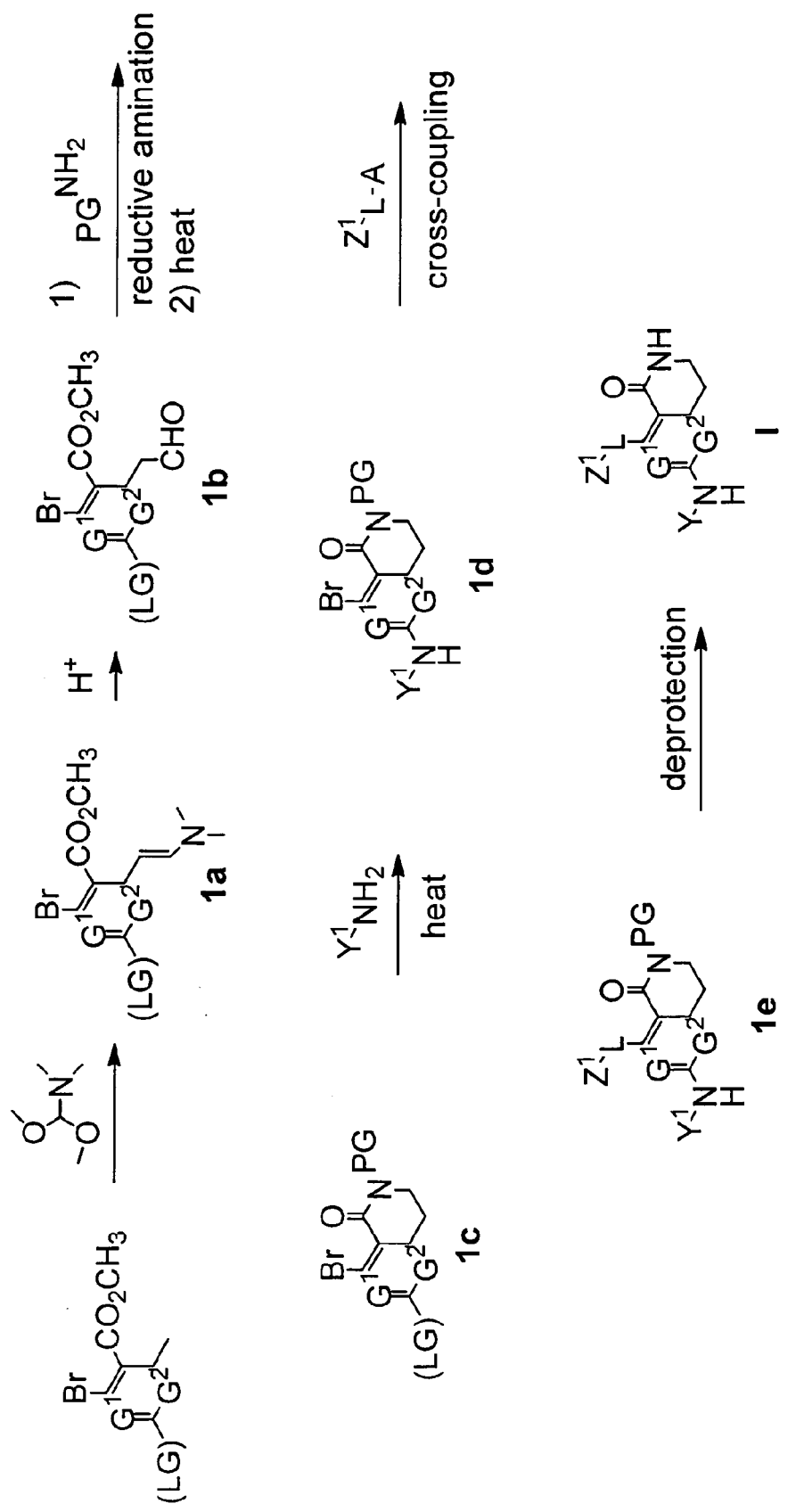
FIG. 1 shows a scheme for the synthesis of compounds of Formula I according to the methods of the invention.

It is noted here that as used in this specification and the appended claims, the singular forms "a," "an," and "the" include plural reference unless the context clearly dictates otherwise.

"Alkoxy" refers to —O(alkyl) where alkyl as defined herein. Representative examples of alkoxy groups include methoxy, ethoxy, t-butoxy, and the like.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. Alkyl includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkenyl" refers to a linear monovalent hydrocarbon radical or a branched monovalent hydrocarbon radical having the number of carbon atoms indicated in the prefix and containing at least one double bond, but no more than three double bonds. For example, $C_{2-8}$alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those hydrocarbon groups having one triple bond and one double bond. For example, $C_{2-8}$alkynyl is meant to include ethynyl, propynyl and the like.

"Amino" refers to a monovalent radical —$NH_2$.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Aryl groups include aromatic ring(s) fused to non-aromatic cycloalkyl groups and where the point of attachment to the remainder of the molecule can be through any suitable ring atom of any ring. Thus the phrase includes, but is not limited to, groups such as phenyl, anthracenyl, naphthyl by way of example. Non-limiting examples of aryl groups include phenyl, 1-naphthyl, 2-naphthyl and 4-biphenyl.

"Bond" when used as an element in a Markush group means that the corresponding group does not exist, and the groups of both sides are directly linked.

"Cycloalkyl" refers to a saturated or partially saturated cyclic group of from 3 to 14 carbon atoms and no ring heteroatoms and having a single ring or multiple rings including fused, bridged, and spiro ring systems. The term "cycloalkyl" includes cycloalkenyl groups, a partially saturated cycloalkyl ring having at least one site of >C=C< ring unsaturation. Examples of cycloalkyl groups include, for instance, adamantyl, cyclopropyl, cyclobutyl, cyclopentyl, cyclooctyl, and cyclohexenyl. "$C_{u'-v'}$cycloalkyl" refers to cycloalkyl groups having u' to v' carbon atoms as ring members. "$C_{u'-v'}$cycloalkenyl" refers to cycloalkenyl groups having u' to v' carbon atoms as ring members.

"Heteroaryl" refers to a cyclic or polycyclic radical having at least one aromatic ring and from one to five ring heteroatom selected from N, O, and S, and optionally one or more oxo (=O) substituents attached to one or more carbon ring atoms, and wherein the nitrogen and sulfur ring atoms are optionally oxidized. A heteroaryl group can be attached to the remainder of the molecule through a heteroatom or through a carbon atom and can contain 5 to 10 carbon atoms. Heteroaryl groups include polycyclic aromatic ring(s) fused to non-aromatic cycloalkyl or heterocyclyl groups, and where the point of attachment to the remainder of the molecule can be through any suitable ring atom of any ring. In a polycyclic heteroaryl group, the ring heteroatom(s) can be in either an aromatic or non-aromatic ring or both. The term "aromatic ring" include any ring having at least one planar resonance structure where 2n+2 pi electrons are delocalized about the ring. Non-limiting examples of heteroaryl groups include xanthine, hypoxanthine, 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl, 6-quinolyl 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. "Bicyclic heteroaryl" refers to a heteroaryl radical that contains two fused rings.

The term "heterocyclyl" or "heterocycloalkyl" refers to a cycloalkyl group containing at least one ring heteroatom and optionally one or more oxo substituents. As used herein, the term "heteroatom" is meant to include oxygen (O), nitrogen (N), and sulfur (S), wherein the heteroatoms are optionally oxidized, and the nitrogen atom(s) are optionally quaternized. Each heterocycle can be attached at any available ring carbon or heteroatom. Each heterocycle may have one or more rings. When multiple rings are present, they can be fused together. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, piperidine, morpholine, piperazine, isoxazoline, pyrazoline, imidazoline, pyrrolidine, and the like.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "haloC$_{1-8}$alkyl" is meant to include difluoromethyl, trifluoromethyl, 2,2,2-trifluoroethyl, 4-chlorobutyl, 3-bromopropyl, and the like. The term "haloalkenyl", and "haloalkynyl" refers to alkenyl and alkynyl radicals having one or more halogen atoms. Additionally, term "haloalkoxy" refers to an alkoxy radical substituted with one or more halogen atoms. In one group of embodiments, the haloakyl, haloalkenyl, haloalkynyl, and haloalkoxy groups have from one to 5 or from one to 3 halo atoms. Examples of haloalkoxy groups include difluoromethoxy and trifluoromethoxy. In one group of embodiments, the halo atoms of the haloalkenyl and haloalkynyl groups are attached to the aliphatic portions of these groups.

The terms "optional" or "optionally" as used throughout the specification means that the subsequently described event or circumstance may but need not occur, and that the description includes instances where the event or circumstance occurs and instances in which it does not. For example, "heteroaryl group optionally substituted with an alkyl group means that the alkyl may but need not be present, and the description includes situations where the heteroaryl group is substituted with an alkyl group and situations where the heteroaryl group is not substituted with the alkyl group.

The term "oxo" includes a mono —O or divalent =O oxygen atom.

The term "phenylene" refers to a divalent phenyl group.

In each of the above embodiments designating a number of atoms e.g. "C$_{1-8}$" is meant to include all possible embodiments that have one fewer atom. Non-limiting examples include C$_{1-4}$, C$_{1-5}$, C$_{1-6}$, C$_{1-7}$, C$_{2-8}$, C$_{2-7}$, C$_{3-8}$, C$_{3-7}$ and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "pharmaceutically acceptable carrier or excipient" means a carrier or excipient that is useful in preparing a pharmaceutical composition that is generally safe, nontoxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refer to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

"Tautomer" refers to alternate forms of a molecule that differ in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

The terms "treat", "treating", "treatment" and grammatical variations thereof as used herein, includes partially or completely delaying, alleviating, mitigating or reducing the intensity, progression, or worsening of one or more attendant symptoms of a disorder or condition and/or alleviating, mitigating or impeding one or more causes of a disorder or condition. Treatments according to the invention may be applied preventively, prophylactically, palliatively or remedially.

The term "wavy line" signifies the point of attachment of the substituent to the remainder of the molecule. When the wavy line is not depicted as being specifically appended to a specific ring atom, the point of attachment can be to any suitable atom of the substituent. For example, the wavy line in the following structure:

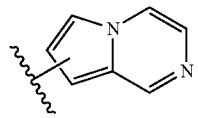

is intended to include, as the point of attachment, any of the six substitutable carbon atoms.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The compounds of the present invention may also contain unnatural proportions of atomic isotopes at one or more of the atoms that constitute such compounds. For example, the compounds may be radiolabeled with isotopes, such as for example deuterium ($^2$H), tritium ($^3$H), iodine-125 ($^{125}$I) or carbon-14 ($^{14}$C). All isotopic variations of the compounds of the present invention, whether radioactive or not, are intended to be encompassed within the scope of the present invention.

Unless indicated otherwise, the nomenclature of substituents that are not explicitly defined herein are arrived at by naming the terminal portion of the functionality followed by the adjacent functionality toward the point of attachment. For example, the substituent "alkoxyalkyl" refers to an akyl group that is substituted with alkoxy, "hydoxyalkyl" refers to an akyl group that is substituted with hydroxyl, and (phenyl)C$_{1-8}$alkyl refers to an akyl group that is substituted with phenyl. For these substituents, the point of attachment is at the alkyl group.

It is understood that the definitions and formulas provided herein are not intended to include impermissible substitution patterns (e.g., methyl substituted with 5 fluoro groups). Such impermissible substitution patterns are well known to the skilled artisan.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of Syk" and related terms and phrases refer to a condition or disorder associated with inappropriate, e.g., less than or greater than normal, activity of Syk and at least partially responsive to or affected by modulation of Syk (e.g., Syk antagonist or agonist results in some improvement in patient well-being in at least some patients). Inappropriate functional activity of Syk might arise as the result of expression of Syk in cells which normally do not express the receptor, greater than normal production of Syk, or slower than normal metabolic inactivation or elimination of Syk or its active metabolites, increased expression of Syk or degree of intracellular activation (leading to, e.g., inflammatory and immune-related disorders and conditions) or decreased expression of Syk. A condition or disorder associated with Syk may include a "Syk-mediated condition or disorder".

As used herein, the phrases "a condition or disorder mediated at least in part by Syk kinase activity", and related phrases and terms refer to a condition or disorder characterized by inappropriate, e.g., greater than normal, Syk activity. Inappropriate Syk functional activity might arise as the result of Syk expression in cells which normally do not express Syk or increased Syk expression or degree of intracellular activation (leading to, e.g., inflammatory and immune-related disorders and conditions). A condition or disorder mediated at least in part by Syk or JAK kinase activity may be completely or partially mediated by inappropriate Syk functional activity. However, a condition or disorder mediated at least in part by Syk kinase activity is one in which modulation of Syk results in some effect on the underlying condition or disorder (e.g., an Syk antagonist results in some improvement in patient well-being in at least some patients).

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

The terms "modulate", "modulation" and the like refer to the ability of a compound to increase or decrease the function and/or expression of Syk, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with Syk, either directly or indirectly, and/or the upregulation or downregulation of the expression of Syk, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of Syk can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Subject" refers to human and non-human animals, especially mammals. Examples of subjects include, but are not limited to, humans, cows, dogs, cats, goats, sheep, pigs and rabbits.

Kinase Inhibitors

In one group of embodiments, provided is a compound of Formula (I):

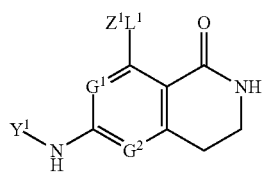

or a tautomer or a pharmaceutically acceptable salt thereof, wherein $G^1$ and $G^2$ are independently selected from the group consisting of N and C—X;

X is independently selected from the group consisting of H, halo, and $C_{1-8}$alkyl;

$L^1$ is selected from the group consisting of a bond, NH, O, and S;

$Z^1$ is selected from the group consisting of aryl and heteroaryl, wherein the aryl and heteroaryl are optionally substituted with 1 to 5 $R^1$;

$R^1$ is independently selected from the group consisting of halo, $C_{1-8}$alkyl, $C_{2-8}$alkenyl, halo$C_{1-8}$alkyl, $(CH_2)_n SR^{1a}$, $(CH_2)_n OR^{1a}$, $O(CH_2)_j OR^{1a}$, $(CH_2)_n NR^{1b}R^{1c}$, $(CH_2)_n COR^{1e}$, $(CH_2)_n CONR^{1b}R^{1c}$, $(CH_2)_n NR^{1b}COR^{1e}$, $(CH_2)_n CONR^{1b}(OR^{1a})$, $(CH_2)_n CO_2R^{1a}$, $O(CH_2)_n CO_2R^{1a}$, $(CH_2)_n NR^{1b}CO_2R^{1a}$, $(CH)_n SO_2NR^{1b}R^{1c}$, $(CH_2)_n NR^{1b}SO_2R^{1e}$, $(CH_2)_n SOR^{1e}$, $(CH_2)_n SO_2R^{1e}$, oxo, $(CH_2)_n CN$, $N_3$, $NO_2$, and -$L^2$-W, where n is 0, 1, 2, 3, 4, 5, or 6 and j is 1, 2, 3, 4, 5, or 6;

$L^2$ is selected from the group consisting of —$O(CH_2)_b$—, —SO—, —$SO_2$—, —CO—, —$NR^{1d}$—, —$CONR^{1d}(CH_2)_b$—, —$NR^{1d}CO$—, —$NR^{1d}SO_2$—, —$SO_2NR^{1d}$—, a bond, and —$(CH_2)_e$— where b is 0, 1, 2, 3, 4, or 5 and e is 1, 2, 3, 4, or 5;

W is selected from the group consisting of aryl, heteroaryl, cycloalkyl, and heterocyclyl each optionally substituted with 1 to 3 $R^2$;

$R^2$ is independently selected from the group consisting of halo, $C_{1-8}$alkyl, $C_{2-8}$alkenyl, halo$C_{1-8}$alkyl, $(CH_2)_m SR^{2a}$, $(CH_2)_m OR^{2a}$, $O(CH_2)_k OR^{2a}$, $(CH_2)_m NR^{2b}R^{2c}$, $(CH_2)_m COR^{2e}$, $(CH_2)_m CONR^{2b}R^{2c}$, $(CH_2)_m NR^{2b}COR^{2e}$, $(CH_2)_m CONR^{2b}(OR^{2a})$, $(CH_2)_m CO_2R^{2a}$, $O(CH_2)_m CO_2R^{2a}$, $(CH_2)_m NR^{2b}CO_2R^{2a}$, $(CH)_m SO_2NR^{2b}R^{2c}$, $(CH_2)_m NR^{2b}SO_2R^{2e}$, $(CH_2)_m SOR^{2e}$, $(CH_2)_m SO_2R^{2e}$, oxo, $(CH_2)_m CN$, $N_3$, and $NO_2$, where m is 0, 1, 2, 3, 4, 5, or 6 and k is 1, 2, 3, 4, 5, or 6;

$R^{1a}$, $R^{1b}$, $R^{1c}$, $R^{1d}$, $R^{2a}$, $R^{2b}$, and $R^{2c}$ are independently selected from the group consisting of H, $C_{2-8}$alkenyl, and halo$C_{1-8}$alkyl;

$R^{1e}$ and $R^{2e}$ are independently selected from the group consisting of $C_{1-8}$alkyl, $C_{2-8}$alkenyl, and halo$C_{1-8}$alkyl;

$Y^1$ is

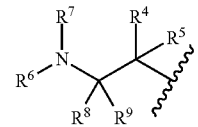

or $(CH_2)_v(Y^2)$, wherein v is 0, 1, 2, or 3;

$Y^2$ is selected from the group consisting of $CH_2CH_3$, $(CH_2)_3NH_2$, cycloalkyl, heterocyclyl, aryl, and heteroaryl, wherein the cycloalkyl, heterocyclyl, aryl, and heteroaryl are optionally substituted with 1 to 3 $R^{10}$;

$R^4$ is selected from the group consisting of H, halo, $C_{1-8}$alkyl, $C_{2-8}$alkenyl, halo$C_{1-8}$alkyl, $(CH_2)_p SR^{4a}$, $(CH_2)_p SOR^{4a}$, $(CH_2)_p SO_2R^{4a}$, $(CH_2)_p OR^{4a}$, $(CH_2)_p NR^{4b}R^{4c}$, $(CH_2)_f CONR^{4b}R^{4c}$, $(CH_2)_p NR^{4b}COR^{4d}$, $(CH_2)_f CO_2R^{4a}$, $(CH_2)_p NR^{4b}CO_2R^{4a}$, $(CH_2)_f$cycloalkyl, $(CH_2)_p(O)$cycloalkyl, $(CH_2)_p(S)$cycloalkyl, $(CH)_p SO_2NR^{4b}R^{4c}$, $(CH_2)_p NH$cycloalkyl, $(CH_2)_f CN$, $(CH_2)_f$(aryl), $(CH_2)_f$(heteroaryl), $(CH_2)_f$(aryl)(heteroaryl), $(CH_2)_f$(heterocyclyl), $(CH_2)_p(O)(CH_2)_f$(aryl), (CH$_2$)$_p$(O)(CH$_2$)$_f$(heteroaryl), (CH$_2$)$_p$(O)(CH$_2$)$_f$C$_{3-8}$cycloalkyl, and (CH$_2$)$_p$(O)(CH$_2$)$_f$(heterocyclyl), where the aryl, heteroaryl, cycloalkyl, and heterocyclyl are each optionally substituted with 1 to 3 R$^{11a}$, f is 0, 1, 2, 3, 4, 5, or 6, and p is 1, 2, 3, 4, 5, or 6; or R$^4$ and R$^5$ together form =O or a 3 to 8 membered carbocyclic or heterocyclic ring optionally substituted with 1 to 3 R$^{11a}$;

R$^5$ is selected from the group consisting of H and C$_{1-8}$alkyl; or R$^5$ is joined to the adjacent nitrogen atom to form a 4 to 6 membered heterocyclic ring optionally substituted with 1 to 3 R$^{11a}$;

R$^6$ is selected from the group consisting of H, C$_{1-8}$alkyl, OH, O(C$_{1-8}$alkyl), CO$_2$R$^{6a}$, CO(NR$^{6a}$R$^{6b}$), and C$_{3-8}$cycloalkyl; or R$^6$ together with R$^7$ and the atoms to which they are attached to form a heterocyclyl ring optionally substituted with 1 to 3 R$^{11b}$;

R$^7$ is selected from the group consisting of H, C$_{1-8}$alkyl, and cycloalkyl;

R$^8$ is selected from the group consisting of H, C$_{1-8}$alkyl, (CH$_2$)$_u$NR$^{8b}$R$^{8c}$, (CH$_2$)$_g$CONR$^{8b}$R$^{8c}$, (CH$_2$)$_g$CO(CH$_2$)$_u$NR$^{8b}$R$^{8c}$, (CH$_2$)$_g$CO$_2$R$^{8a}$, (CH$_2$)$_u$OR$^{8a}$, CH(C$_{1-8}$alkyl)OR$^{8a}$, (CH$_2$)$_g$cycloalkyl, (CH$_2$)$_g$heterocyclyl, (CH$_2$)$_g$aryl, (CH$_2$)$_g$heteroaryl, and (CH$_2$)$_u$(O)(aryl), where the aryl, cycloalkyl, heteroaryl, and heterocyclyl are each optionally substituted with 1 to 3 R$^{11c}$, g is 0, 1, 2, 3, 4, 5, or 6 and u is 1, 2, 3, 4, 5, or 6; or R$^8$ together with R$^9$ and the atoms to which they are attached to form =O, =S, or a cycloalkyl or heterocyclyl ring optionally substituted with R$^{11c}$.

R$^9$ is H or C$_{1-8}$alkyl;

R$^{10}$ is independently selected from the group consisting of halo, C$_{1-8}$alkyl, C$_{2-8}$alkenyl, haloC$_{1-8}$alkyl, (CH$_2$)$_q$SR$^{10a}$, (CH$_2$)$_q$OR$^{10a}$, (CH$_2$)$_q$NR$^{10b}$R$^{10c}$, (CH$_2$)$_q$COR$^{10d}$, (CH$_2$)$_q$CONR$^{10c}$R$^{10c}$, (CH$_2$)$_q$NR$^{10b}$COR$^{10d}$, (CH$_2$)$_q$CONR$^{10b}$(OR$^{10a}$), (CH$_2$)$_q$CO$_2$R$^{10a}$, O(CH$_2$)$_q$CO$_2$R$^{10a}$, (CH$_2$)$_q$NR$^{10b}$CO$_2$R$^{10a}$, (CH)$_q$SO$_2$NR$^{10b}$R$^{10c}$ (CH$_2$)$_q$NR$^{10b}$SO$_2$R$^{10d}$, (CH$_2$)$_q$SOR$^{10d}$, (CH$_2$)$_q$SO$_2$R$^{10d}$, oxo, (CH$_2$)$_q$CN, N$_3$, N=CH$_2$, NO$_2$, C(O) heterocyclyl, aryl, heteroaryl, cycloalkyl, and heterocyclyl, where the aryl, cycloalkyl, heteroaryl, and heterocyclyl are each optionally substituted with 1 to 3 R$^{11d}$ and q is 0, 1, 2, 3, 4, 5, or 6;

R$^{11a}$, R$^{11b}$, R$^{11c}$, and R$^{11d}$ are independently selected from the group consisting of halo, C$_{1-8}$alkyl, haloC$_{1-8}$alkyl, OH, C$_{1-8}$alkoxy, haloC$_{1-8}$alkoxy, C(O)C$_{1-8}$alkyl, CO$_2$C$_{1-8}$alkyl, and SO$_2$C$_{1-8}$alkyl;

R$^{4a}$, R$^{4b}$, R$^{4c}$, R$^{6a}$, R$^{6b}$, R$^{8a}$, R$^{8b}$, R$^{8c}$, R$^{10a}$, R$^{10b}$, and R$^{10c}$ are independently selected from the group consisting of H, C$_{1-8}$alkyl, C$_{2-8}$alkenyl, and haloC$_{1-8}$alkyl;

R$^{4d}$ and R$^{10d}$ are independently selected from the group consisting of C$_{1-8}$alkyl, C$_{2-8}$alkenyl, and haloC$_{1-8}$alkyl; and the wavy line indicates the point of attachment to the rest of the molecule.

In one group of embodiments, provided is a compound of Formula (Ia)

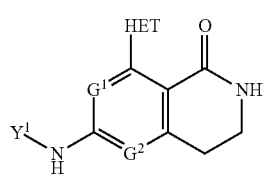

(Ia)

or a tautomer or a pharmaceutically acceptable salt thereof wherein HET is heteoraryl optionally substituted with 1 to 3 R$^1$.

In one group of embodiments, Z$^1$ or HET is selected from the group consisting of

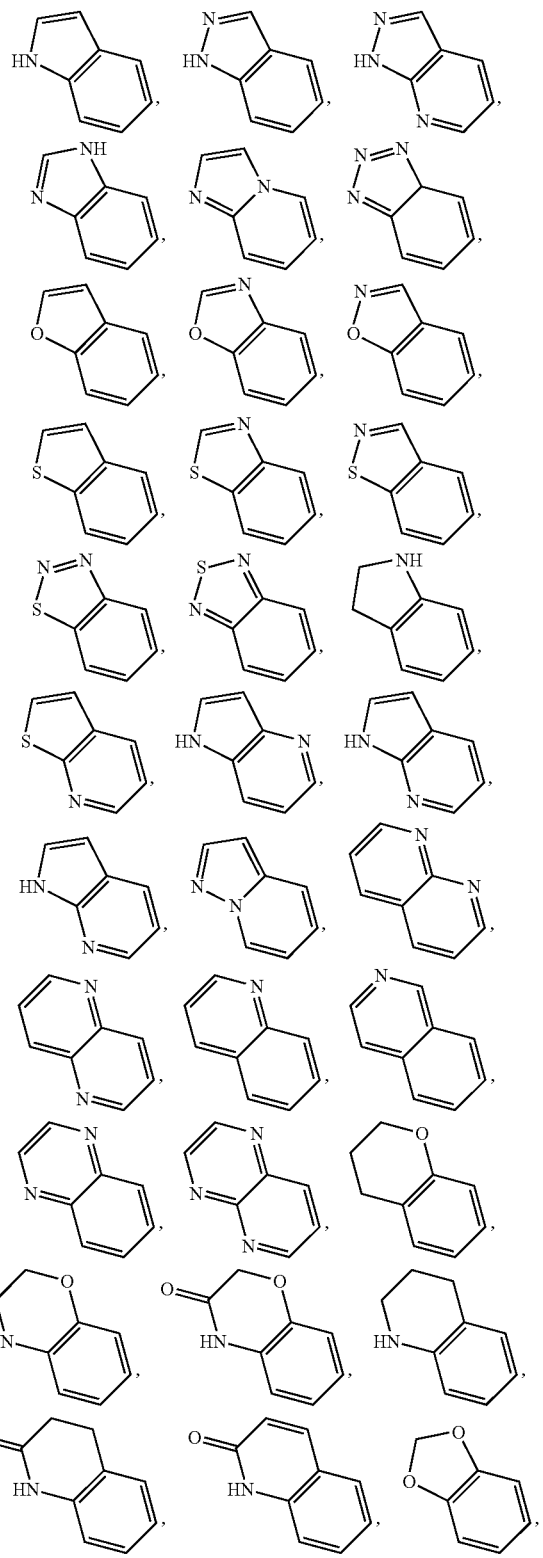

-continued
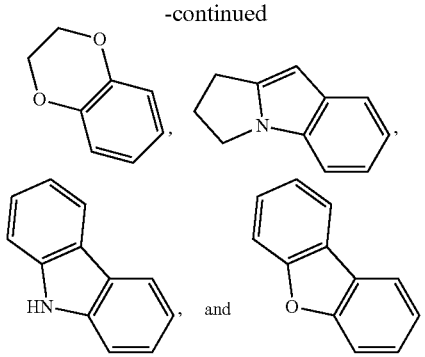
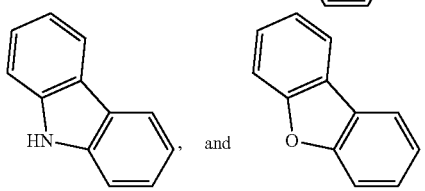
where the point of attachment to the rest of the molecule is at a carbon ring atom.
In one group of embodiments, $Z^1$ or HET is selected from the group consisting of
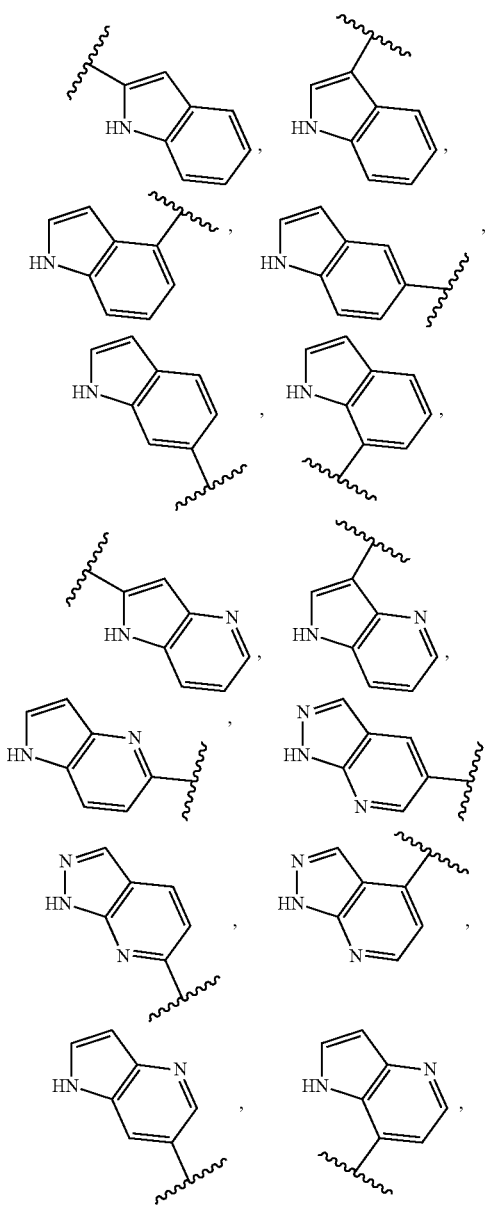
-continued
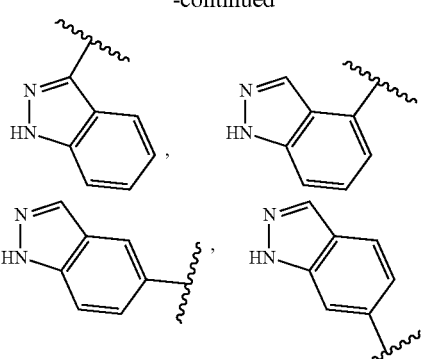
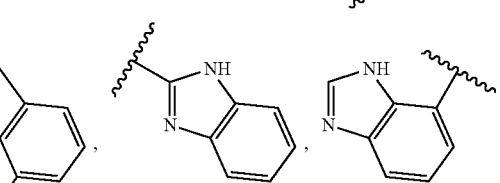
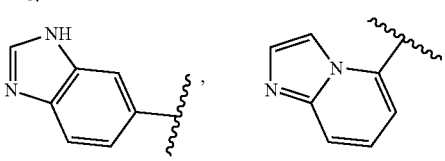
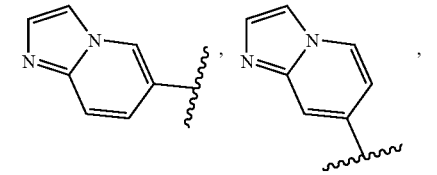
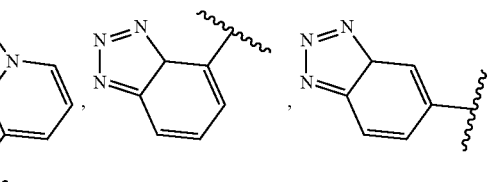
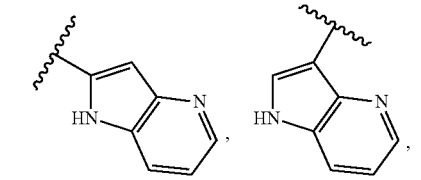
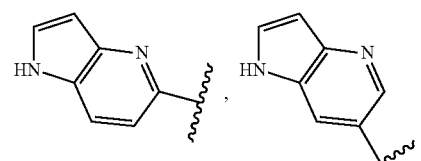
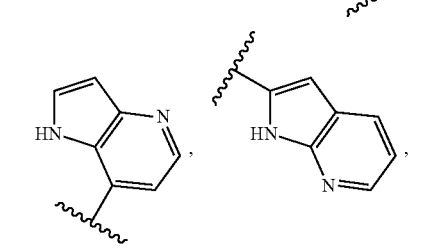

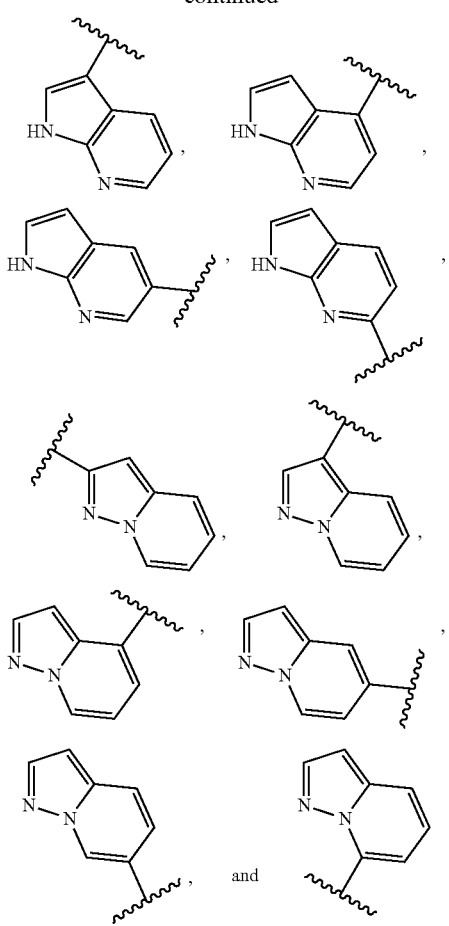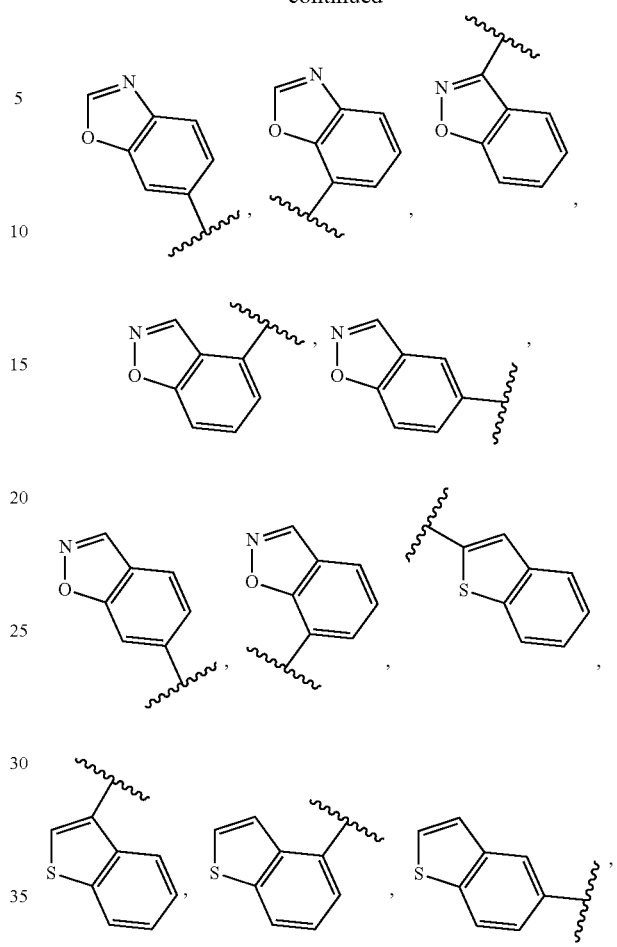
where the wavy line indicates the point of attachment to the rest of the molecule.
In one group of embodiments, $Z^1$ or HET is selected from the group consisting of
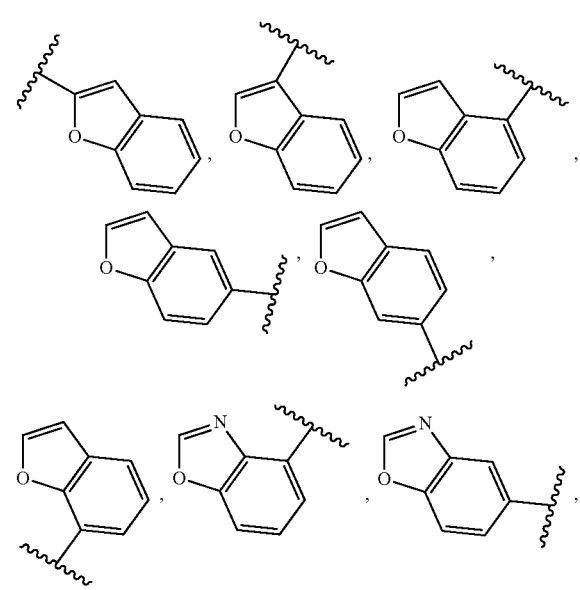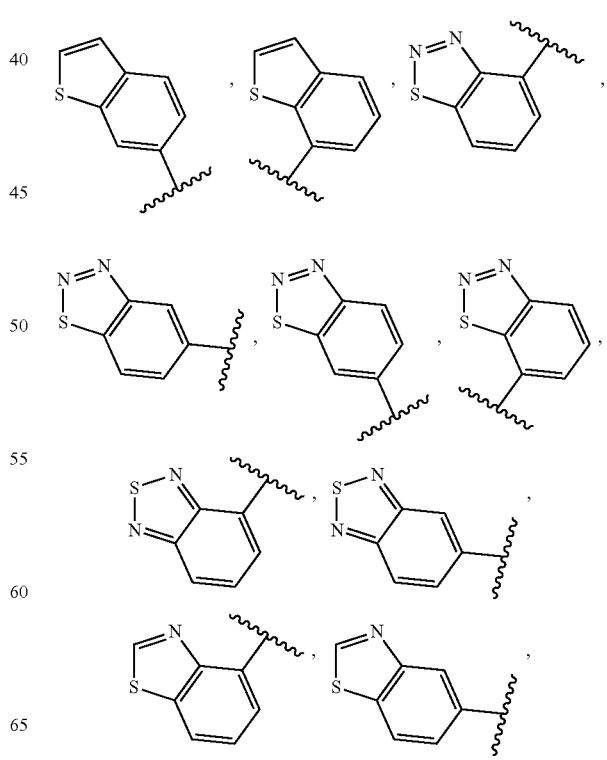

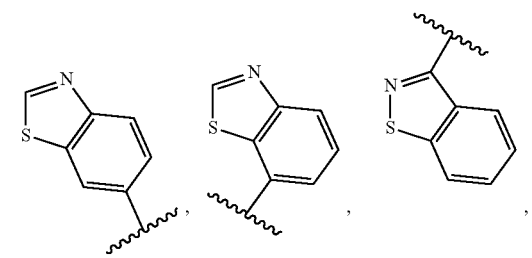
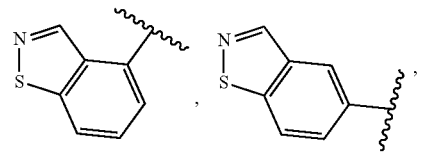
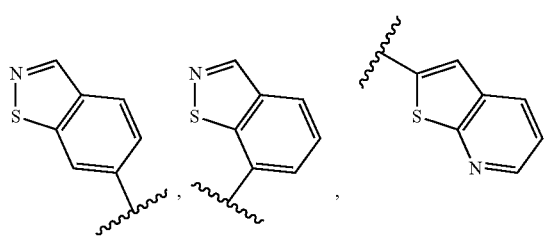
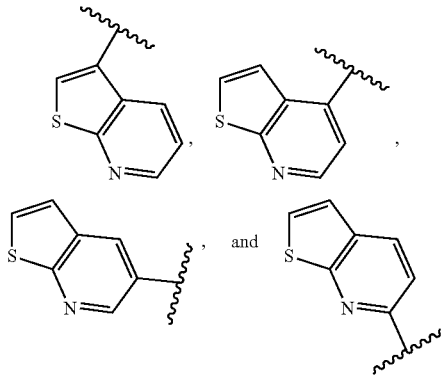
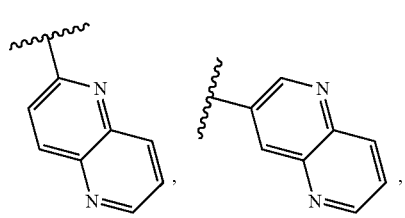
where the wavy line indicates the point of attachment to the rest of the molecule and wherein $Z^1$ or HET is optionally substituted with 1 to 3 $R^1$.
In one group of embodiments, $Z^1$ or HET is selected from the group consisting of
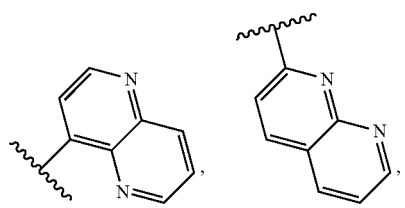
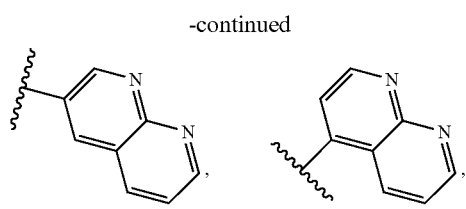
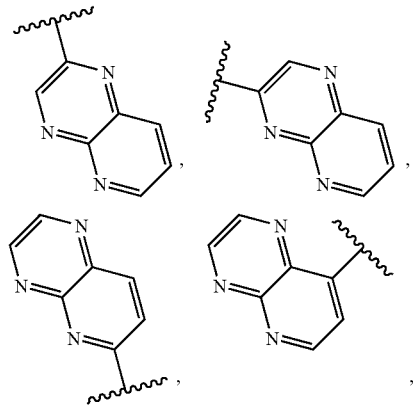
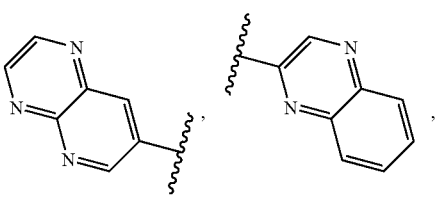
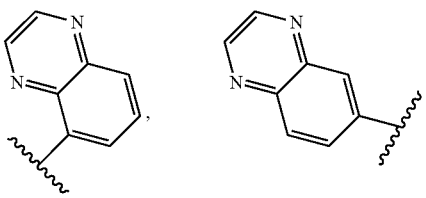
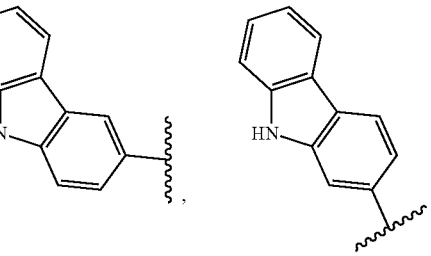
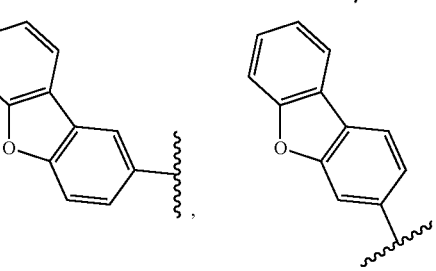
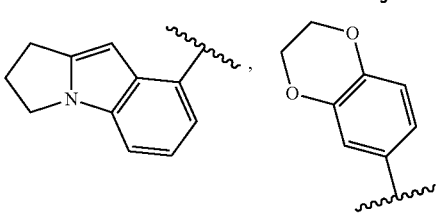

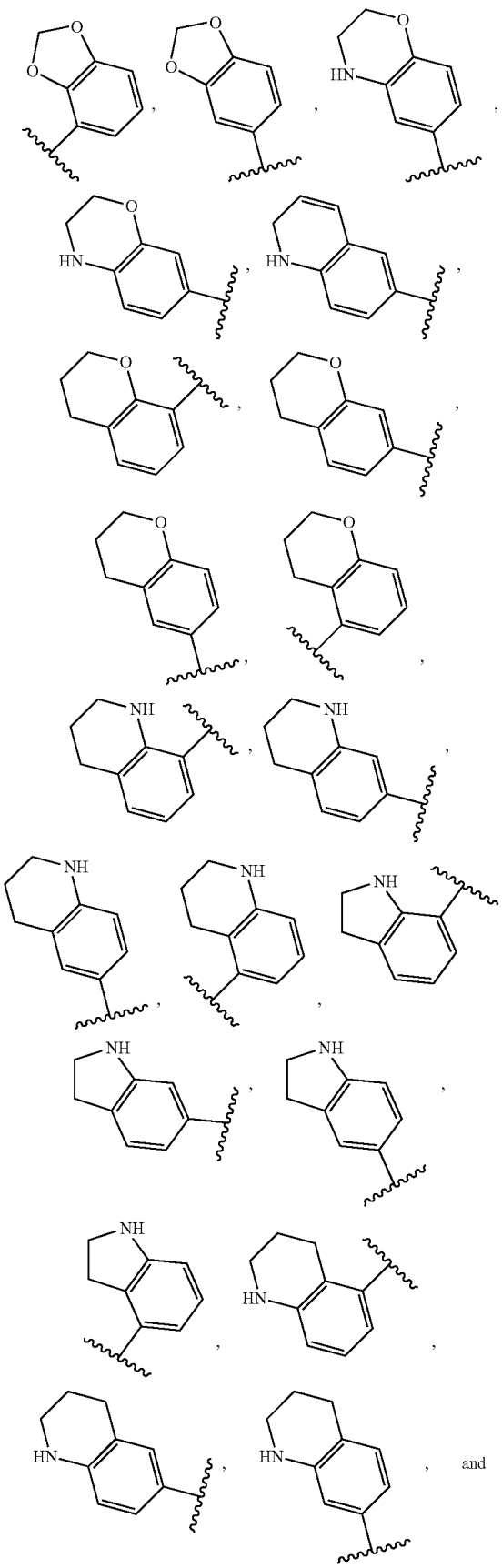, and

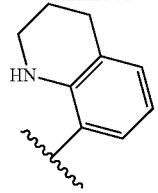

where the wavy line indicates the point of attachment to the rest of the molecule and wherein $Z^1$ or HET is optionally substituted with 1 to 3 $R^1$.

In one group of embodiments, $Z^1$ or HET is selected from the group consisting of

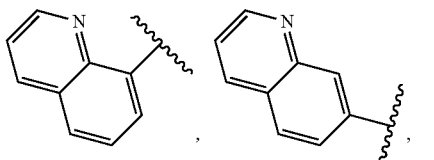

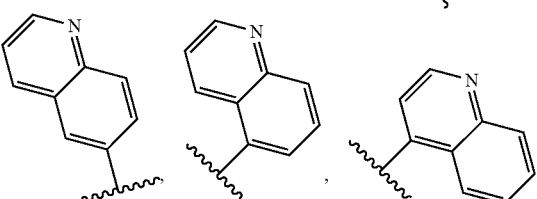

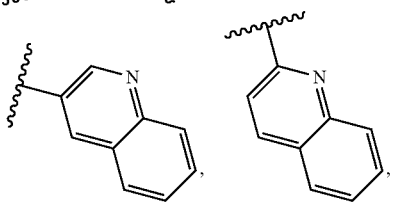

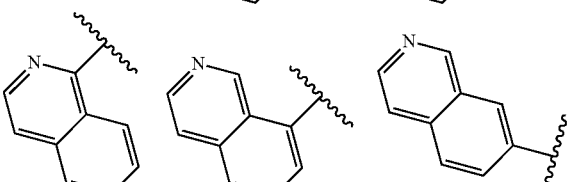

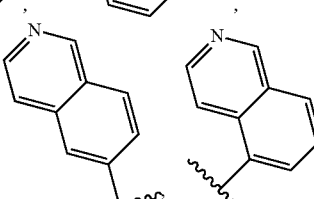

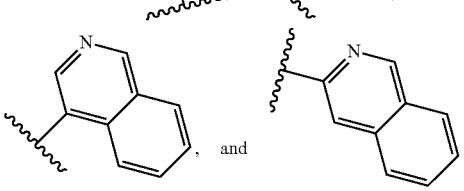, and where the wavy line indicates the point of attachment to the rest of the molecule and wherein $Z^1$ or HET is optionally substituted with 1 to 3 $R^1$.

In one group of embodiments, $Z^1$ or HET is selected from the group consisting of

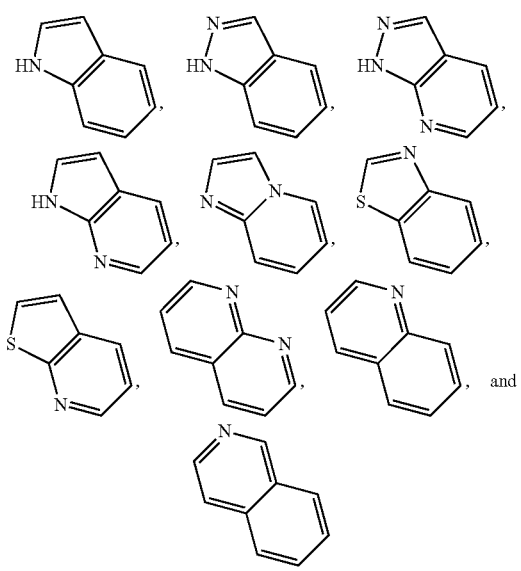

where the point of attachment to the rest of the molecule is at a carbon ring atom and wherein $Z^1$ or HET is optionally substituted with 1 to 3 $R^1$.

In one group of embodiments, $Z^1$ or HET is selected from the group consisting of

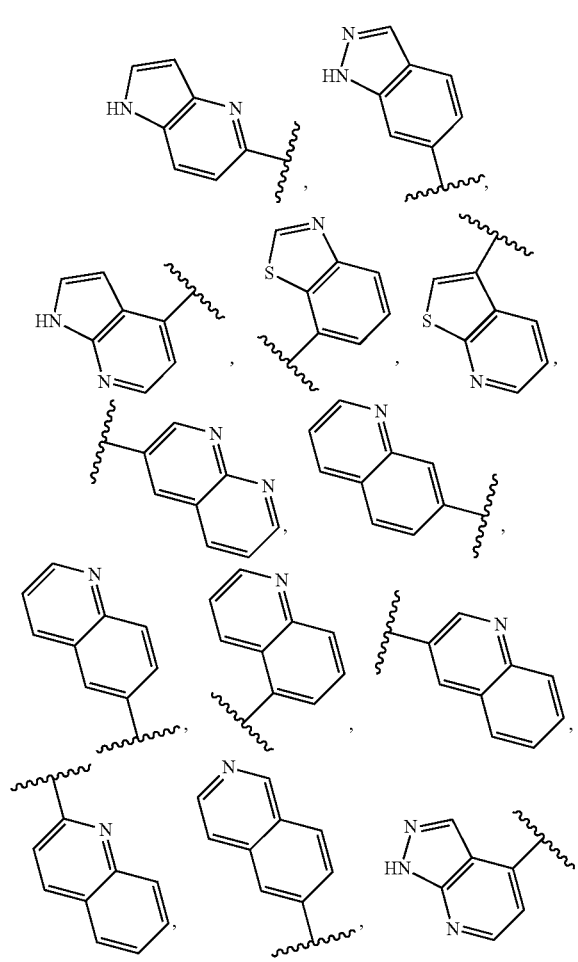

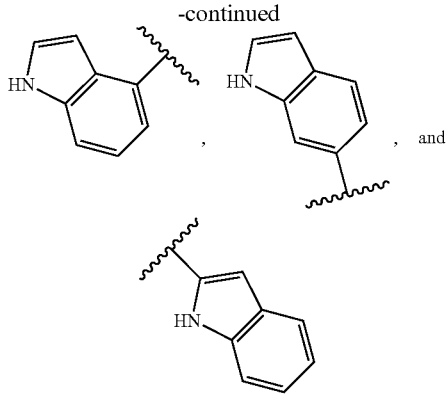

-continued where the wavy line indicates the point of attachment to the rest of the molecule and wherein $Z^1$ or HET is optionally substituted with 1 to 3 $R^1$.

In one group of embodiments, $Z^1$ or HET is a six-membered heteroaryl ring optionally substituted with 1 to 3 $R^1$.

In one group of embodiments, $Z^1$ or HET is selected from the group consisting of

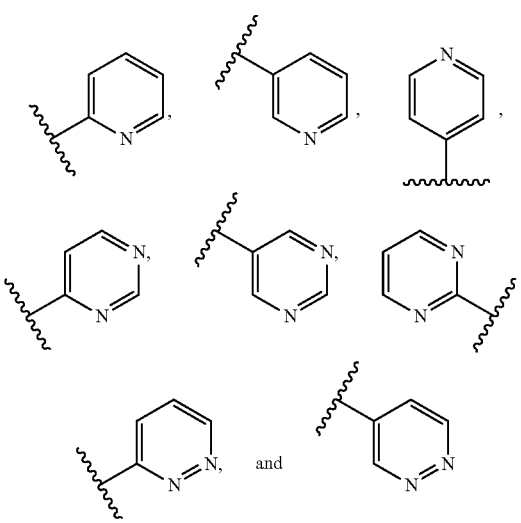

where the wavy line indicates the point of attachment to the rest of the molecule and wherein $Z^1$ or HET is optionally substituted with 1 to 3 $R^1$.

In one group of embodiments, $Z^1$ or HET is a six-membered heteroaryl ring optionally substituted with 1 to 3 $R^1$.

In one group of embodiments, $Z^1$ or HET is selected from the group consisting of

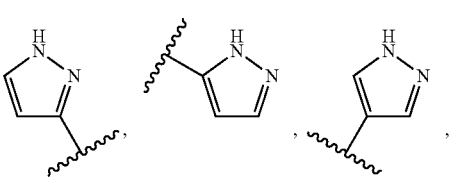

27
-continued
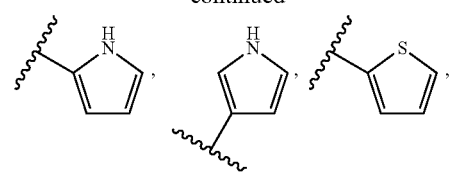
28
-continued
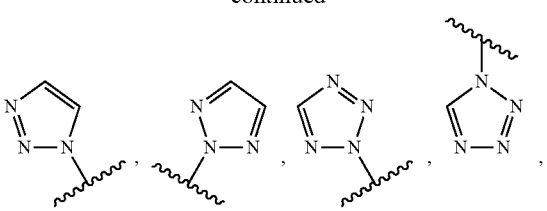
and wherein $Z^1$ or HET is optionally substituted with 1 to 3 $R^1$.
In one group of embodiments, provided is a compound of Formula (Ib)
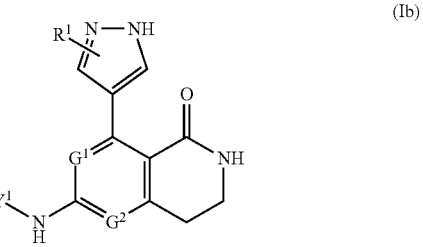
(Ib)
or a tautomer or a pharmaceutically acceptable salt thereof.
In one group of embodiments, at least one $R^1$ is $C_{1-3}$ alkyl.
In one group of embodiments, provided is a compound of Formula (II)

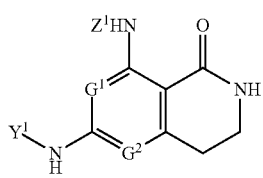 (II)

or a tautomer or a pharmaceutically acceptable salt thereof.

In one group of embodiments, $Z^1$ is selected from the group consisting of:

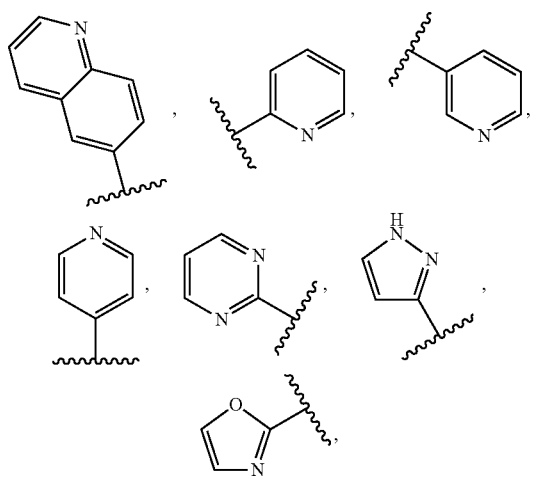

and phenyl;

and wherein $Z^1$ is optionally substituted with 1 to 3 $R^1$.

In one group of embodiments, $Z^1$ is phenyl substituted with 1 to 5 $R^1$.

In one group of embodiments, at least one of $R^1$ is selected from the group consisting of halo, $C_{1-8}$alkyl, cyano, and halo$C_{1-8}$alkoxy.

In one group of embodiments, $Z^1$ is selected from the group consisting of

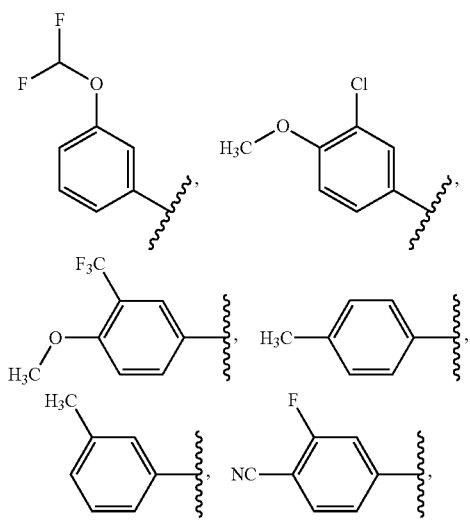

where the wavy line indicates the point of attachment to the rest of the molecule.

In one group of embodiments, $Z^1$ is a five-membered heteroaryl ring optionally substituted with 1 to 3 $R^1$. In some embodiments, the five-membered heteroaryl ring contains one to two ring heteroatoms independently selected from N, O, or S, or three to four ring nitrogen atoms.

In one group of embodiments, $Z^1$ is selected from the group consisting of

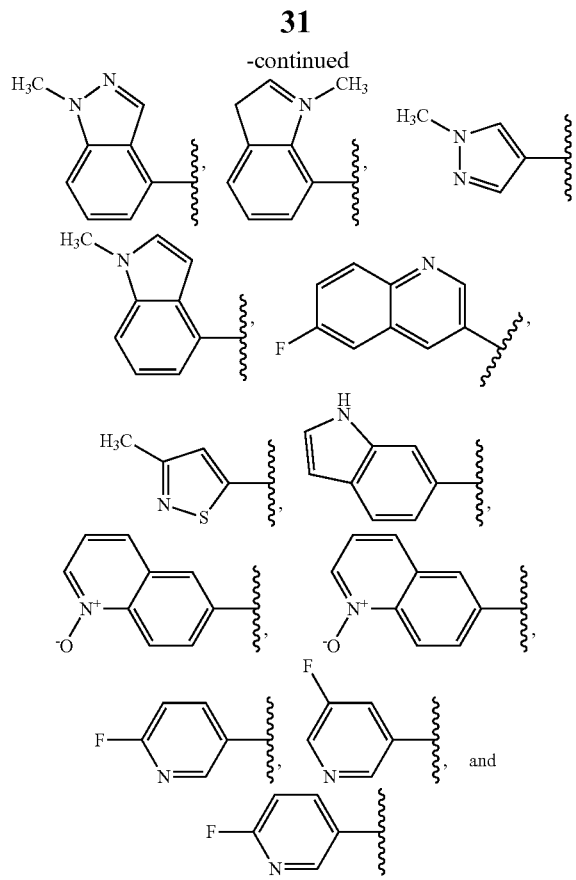

where the wavy line indicates the point of attachment to the rest of the molecule.

In one group of embodiments, at least one $R^1$ is -$L^2$-W.

In one group of embodiments, -$L^2$-W is —CO—NR$^a$R$^b$ where $R^a$ and $R^b$ together form a four to six membered ring optionally substituted with 1 to 3 groups independently selected from halo, $C_{1-8}$alkyl, and halo$C_{1-8}$alkyl.

In one group of embodiments, provided is a compound of Formula (IIa)

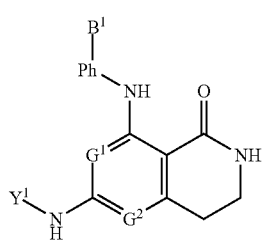

(IIa)

or a tautomer or a pharmaceutically acceptable salt thereof wherein
Ph is phenylene optionally substituted with 1 to 3 $R^1$;
$B^1$ is selected from the group consisting of CO—NR$^a$R$^b$, phenyl, heteroaryl, and heterocyclyl, wherein the phenyl, heteroaryl, and heterocyclyl are each optionally substituted with 1 to 3 $R^2$, and $R^a$ and $R^b$ together form a four to six membered heterocyclic ring optionally substituted with one to three groups independently selected from halo, $C_{1-8}$alkyl, and halo$C_{1-8}$alkyl.

In one group of embodiments is a compound of Formula (IIb)

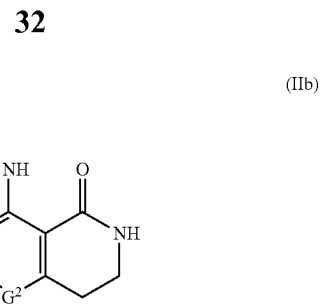

(IIb)

or a tautomer or a pharmaceutically acceptable salt thereof wherein

HET is a monocyclic or bicyclic heteroaryl ring optionally substituted with 1 to 3 $R^1$;

$B^1$ is selected from the group consisting of CO—NR$^a$R$^b$, phenyl, heteroaryl, and heterocyclyl, wherein the phenyl, heteroaryl, and heterocyclyl are each optionally substituted with 1 to 3 $R^2$, and $R^a$ and $R^b$ together form a four to six membered heterocyclic ring optionally substituted with one to three groups independently selected from halo, $C_{1-8}$alkyl, and halo$C_{1-8}$alkyl.

In one group of embodiments, $B^1$ is heteroaryl or heterocyclyl, each optionally substituted with 1 to 3 $R^2$.

In one group of embodiments, $B^1$ is substituted with 1 to 3 $R^2$.

In one group of embodiments, $B^1$ is selected from the group consisting of

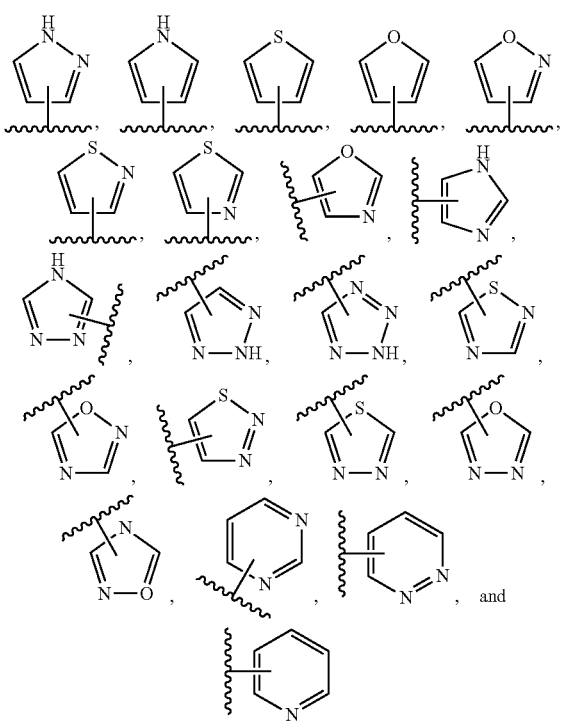

where the wavy line indicates the point of attachment to the rest of the molecule and wherein $B^1$ is optionally substituted with 1 to 3 $R^2$.

In one group of embodiments, $B^1$ is selected from the group consisting of

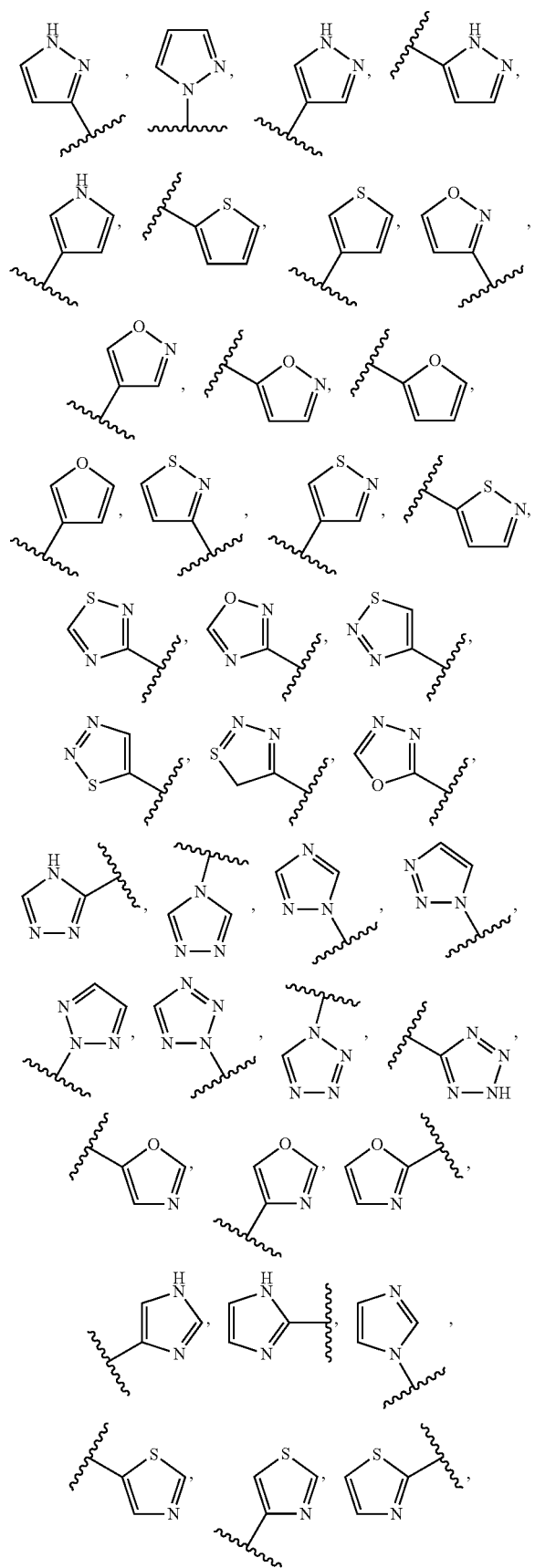

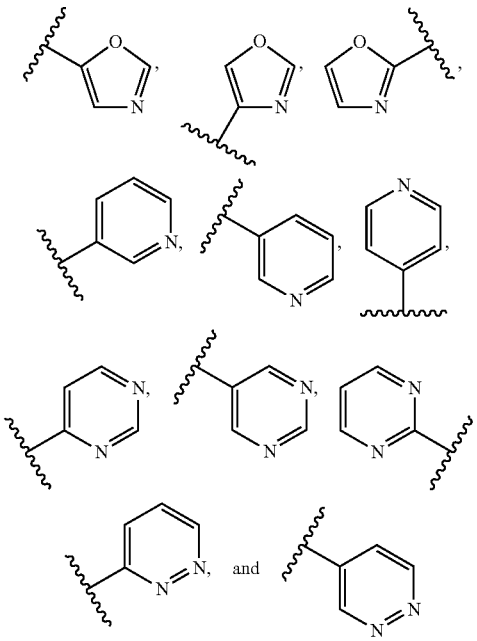

where the wavy line indicates the point of attachment to the rest of the molecule and wherein $B^1$ is optionally substituted with 1 to 3 $R^2$.

In one group of embodiments, $B^1$ is selected from the group consisting of

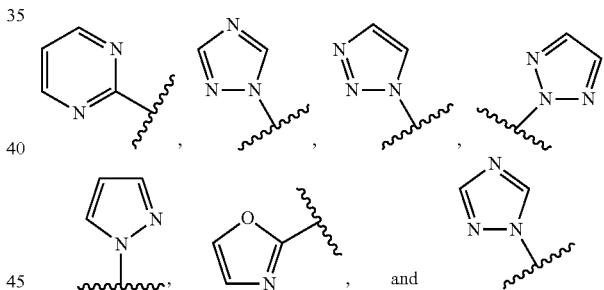

and wherein $B^1$ is optionally substituted with 1 to 3 $R^2$.

In one group of embodiments, $B^1$ is selected from the group consisting of

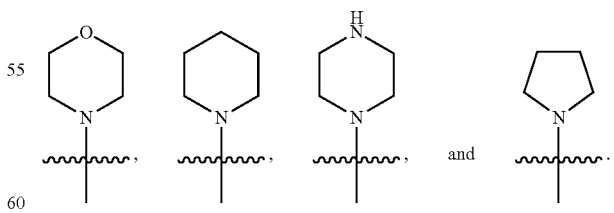

and wherein $B^1$ is optionally substituted with 1 to 3 $R^2$, where the wavy line indicates the point of attachment to the rest of the molecule.

In one group of embodiments, $B^1$-Ph- is selected from the group consisting of

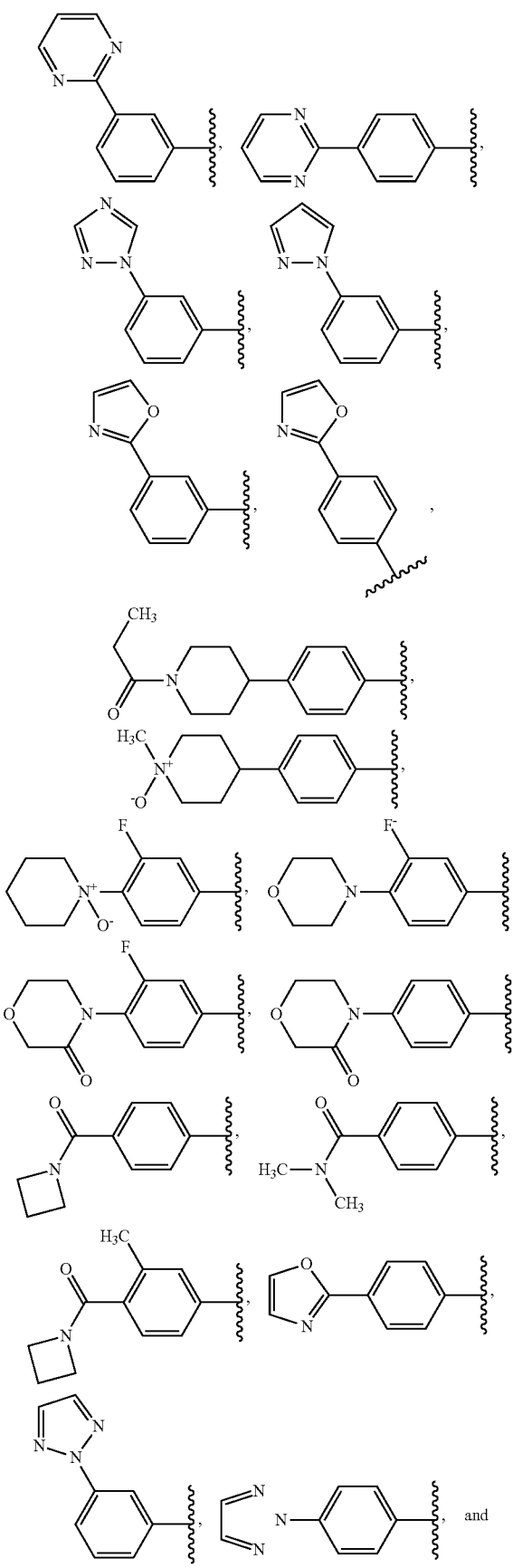

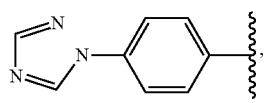

where the wavy line indicates the point of attachment to the rest of the molecule.

In one group of embodiments is a compound or a tautomer or a pharmaceutically acceptable salt thereof wherein B¹-HET- is selected from the group consisting of

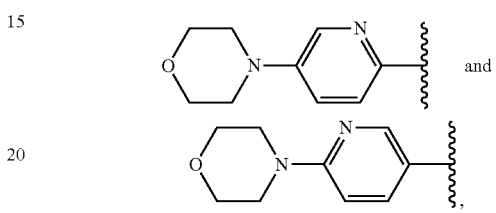

where the wavy line indicates the point of attachment to the rest of the molecule.

In one group of embodiments is a compound or a tautomer or a pharmaceutically acceptable salt thereof wherein HET is selected from the group consisting of:

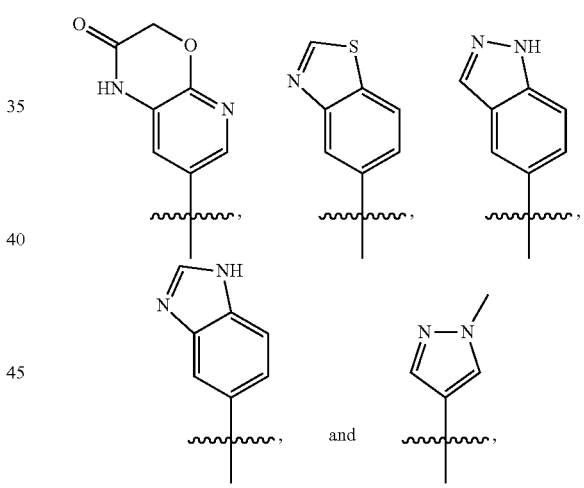

where the wavy line indicates the point of attachment to the rest of the molecule.

In one group of embodiments, Y¹ is

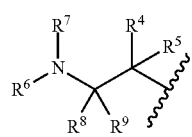

where the wavy line indicates the point of attachment to the rest of the molecule.

In one group of embodiments, Y¹ is selected from the group consisting of

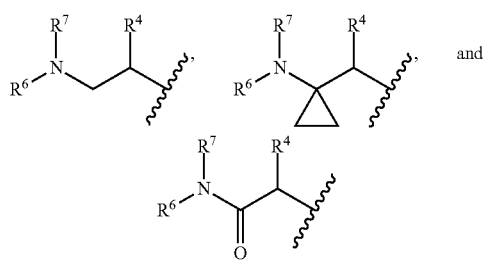

and where the wavy line indicates the point of attachment to the rest of the molecule.

In one group of embodiments, $R^4$ is selected from the group consisting of H, $C_{1-8}$ alkyl, halo$C_{1-8}$alkyl, cycloalkyl, (cycloalkyl)$C_{1-4}$alkyl, (hydroxyl)$C_{1-4}$alkyl, ($C_{1-4}$alkoxy)$C_{1-4}$alkyl, (halo$C_{1-4}$alkoxy)$C_{1-4}$alkyl, $(CH_2)_pNR^{4b}R^{4c}$, $(CH)_pSO_2NR^{4b}R^{4c}$, $(CH_2)_pSOR^{4a}$, $(CH_2)_pSO_2R^{4a}$, $(CH_2)_fCONR^{4b}R^{4c}$, $(CH_2)_pNR^{4d}COR^{4d}$, phenyl, heteroaryl, (phenyl)$C_{1-8}$alkyl, and (heteroaryl)$C_{1-8}$alkyl wherein the phenyl and heteroaryl are optionally substituted with 1 to 3 groups independently selected from halo, $C_{1-4}$alkyl, halo$C_{1-4}$alkyl, $C_{1-4}$alkoxy, and halo$C_{1-4}$alkoxy.

In one group of embodiments, $R^4$ is selected from the group consisting of H, methyl, ethyl, propyl, isopropyl, isobutyl, hydroxymethyl, pyridyl, and phenyl, wherein the pyridyl and phenyl are optionally substituted with 1 to 3 groups independently selected from halo, $C_{1-4}$alkyl, halo $C_{1-4}$alkyl, $C_{1-4}$alkoxy, and halo$C_{1-4}$alkoxy.

In one group of embodiments, $R^4$ is selected from the group consisting of

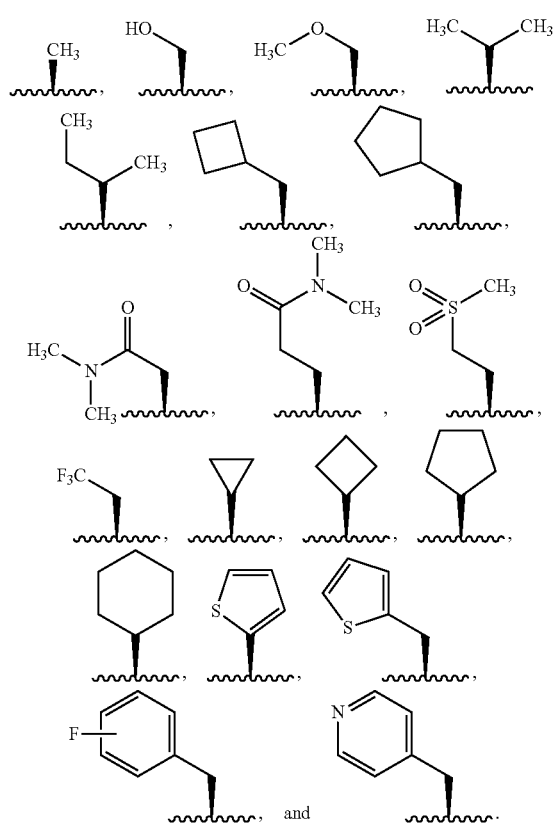

In one group of embodiments, $Y^1$ is selected from the group consisting of

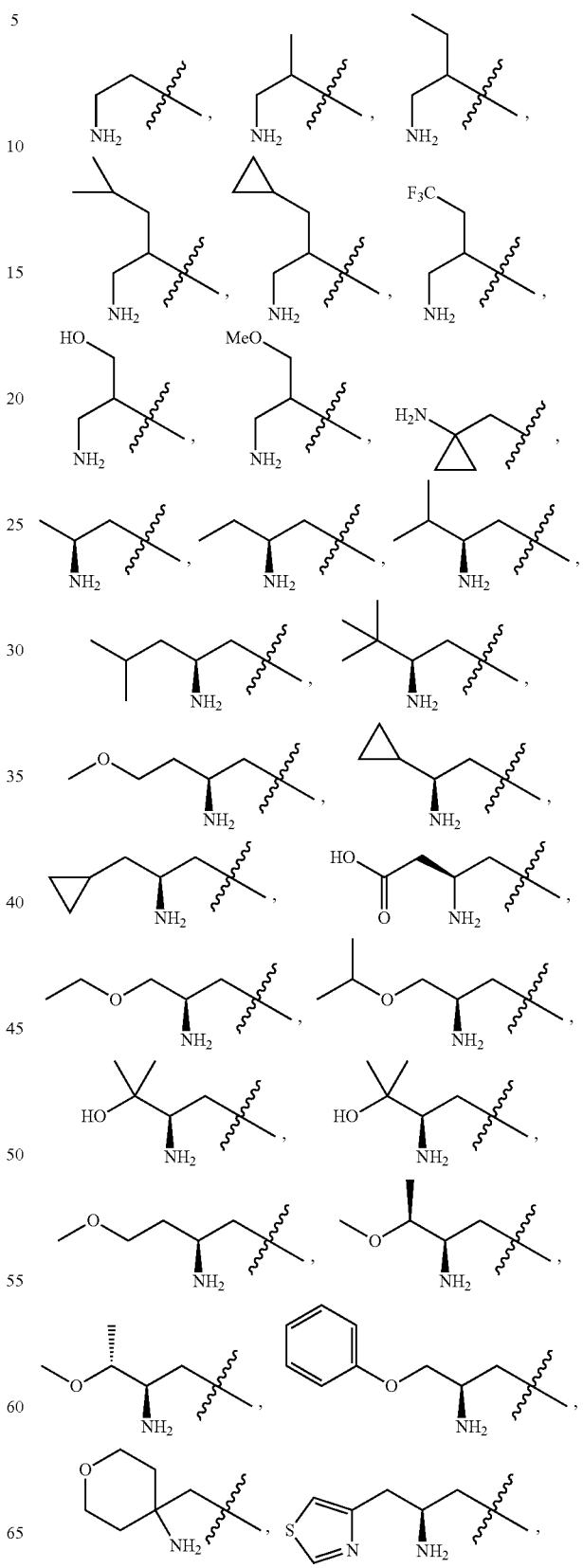

-continued

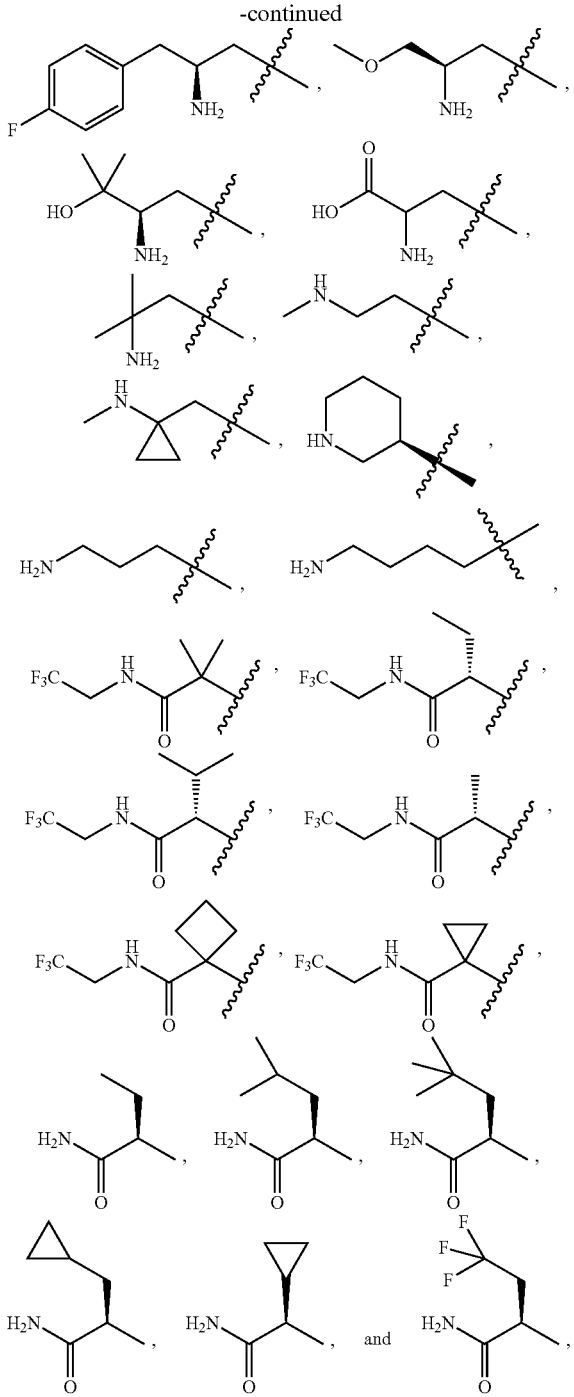

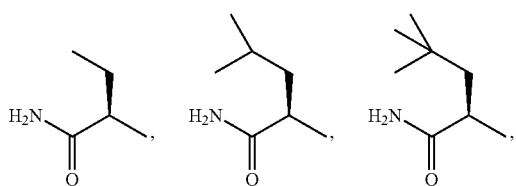

where the wavy line indicates the point of attachment to the rest of the molecule.

In one group of embodiments, Y¹ is selected from

-continued

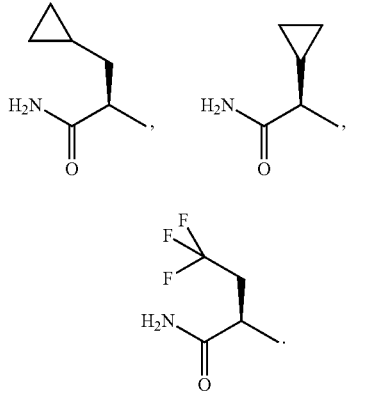

In one group of embodiments is a compound or a tautomer or a pharmaceutically acceptable salt thereof, wherein Y¹ is

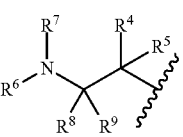

and
R⁵ is joined to the adjacent nitrogen atom to form a 4 to 6 membered heterocyclic ring optionally substituted with 1 to 3 $R^{11a}$, where the wavy line indicates the point of attachment to the rest of the molecule.

In one group of embodiments is a compound wherein Y¹ is

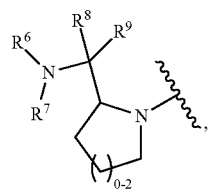

where the wavy line indicates the point of attachment to the rest of the molecule.

In one group of embodiments is a compound wherein Y¹ is

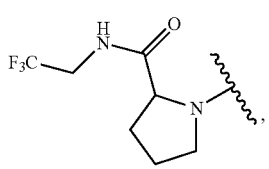 [SMILES: *N1CCCC1C(=O)NCC(F)(F)F]

where the wavy line indicates the point of attachment to the rest of the molecule.

In one group of embodiments, $Y^1$ is $(CH_2)_v(Y^2)$ wherein v is 0 and $Y^2$ is cycloalkyl or heterocycloalkyl each optionally substituted with 1 to 3 $R^{10}$. In one group of such embodiments, $Y^2$ is tetrahydropyranyl, cyclopropyl, cyclobutyl, cyclopentyl or cyclohexyl, each optionally substituted with 1 to 3 $R^{10}$.

In one group of embodiments, $Y^1$ is

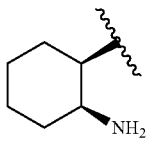 [SMILES: *[C@@H]1CCCC[C@@H]1N]

optionally substituted with 1 to 2 halo and where the wavy line indicates the point of attachment to the rest of the molecule.

In one group of embodiments, $Y^1$ is selected from the group consisting of

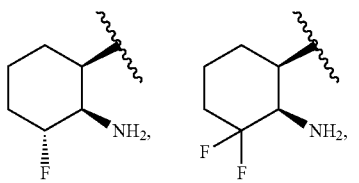

where the wavy line indicates the point of attachment to the rest of the molecule.

In one group of embodiments, $Y^1$ is selected from the group consisting of

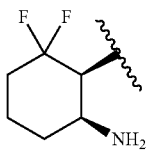

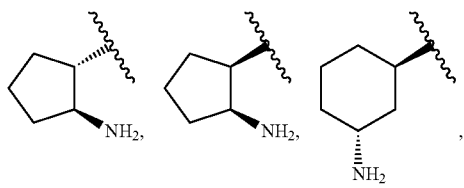

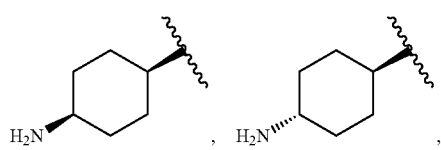

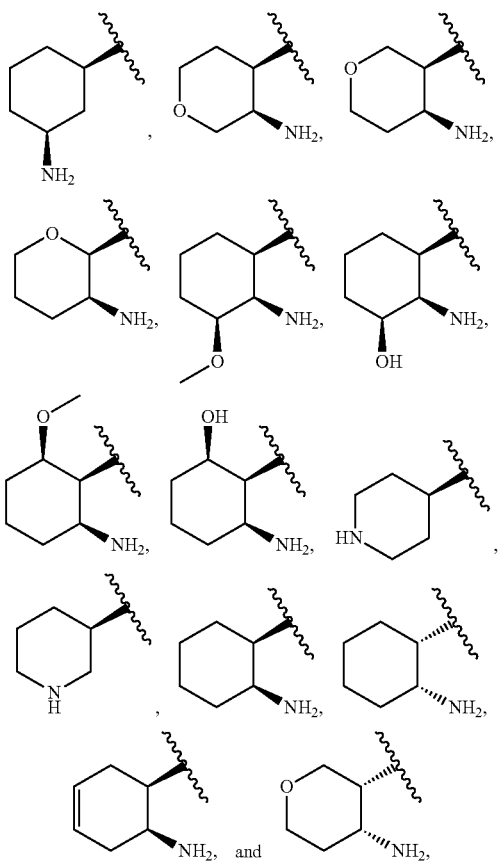

where the wavy line indicates the point of attachment to the rest of the molecule.

In one group of embodiments, $Y^1$ is selected from the group consisting of

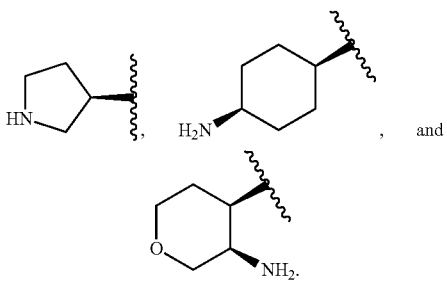

In one group of embodiments, $G^1$ is N and $G^2$ is C—X wherein X is H. In one group of embodiments, $G^1$ is N and $G^2$ is C—X wherein X is halo.

In one group of embodiments, X is fluoro.

In one group of embodiments, for any compound described above, $G^1$ and $G^2$ are both N.

In one group of embodiments, for any compound described above, $G^1$ and $G^2$ are both C—X and X is H.

In one group of embodiments, the compound is a compound in Table 1.

TABLE 1

Structures of Kinase Inhibitors

| EXAMPLE NO. | STRUCTURE | NAME |
| --- | --- | --- |
| 1. | 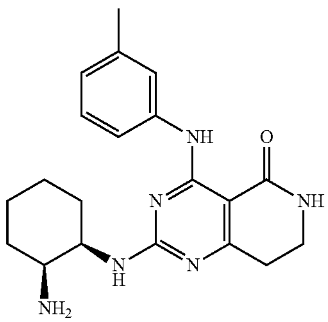 [SMILES: Cc1cccc(Nc2nc(N[C@@H]3CCCC[C@@H]3N)nc3c2C(=O)NCC3)c1] | 2-(((1R,2S)-2-aminocyclohexyl)amino)-4-(m-tolylamino)-7,8-dihydropyrido[4,3-d]pyrimidin-5(6H)-one |
| 2. | 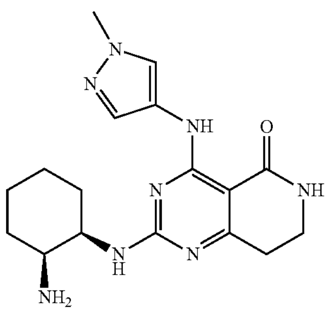 [SMILES: Cn1cc(Nc2nc(N[C@@H]3CCCC[C@@H]3N)nc3c2C(=O)NCC3)cn1] | 2-(((1R,2S)-2-aminocyclohexyl)amino)-4-((1-methyl-1H-pyrazol-4-yl)amino)-7,8-dihydropyrido[4,3-d]pyrimidin-5(6H)-one |
| 3. | 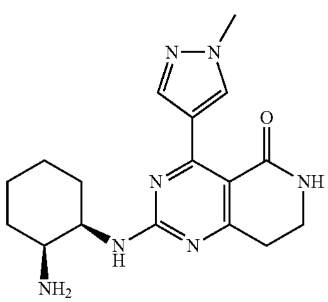 [SMILES: Cn1cc(-c2nc(N[C@@H]3CCCC[C@@H]3N)nc3c2C(=O)NCC3)cn1] | 2-(((1R,2S)-2-aminocyclohexyl)amino)-4-(1-methyl-1H-pyrazol-4-yl)-7,8-dihydropyrido[4,3-d]pyrimidin-5(6H)-one |
| 4. | 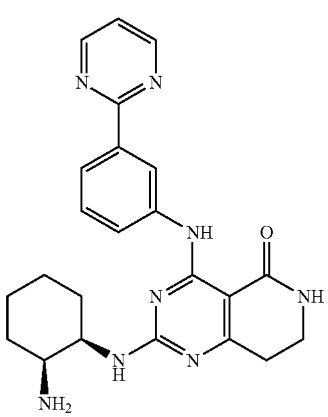 [SMILES: N[C@H]1CCCC[C@H]1Nc1nc2c(c(Nc3cccc(-c4ncccn4)c3)n1)C(=O)NCC2] | 2-(((1R,2S)-2-aminocyclohexyl)amino)-4-((3-(pyrimidin-2-yl)phenyl)amino)-7,8-dihydropyrido[4,3-d]pyrimidin-5(6H)-one |

TABLE 1-continued

Structures of Kinase Inhibitors

| EXAMPLE NO. | STRUCTURE | NAME |
|---|---|---|
| 5. | 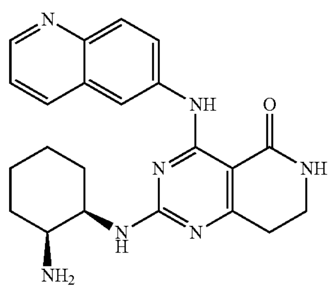 [SMILES: N[C@H]1CCCC[C@H]1Nc1nc2c(c(Nc3ccc4ncccc4c3)n1)C(=O)NCC2] | 2-(((1R,2S)-2-aminocyclohexyl)amino)-4-(quinolin-6-ylamino)-7,8-dihydropyrido[4,3-d]pyrimidin-5(6H)-one |
| 6. | 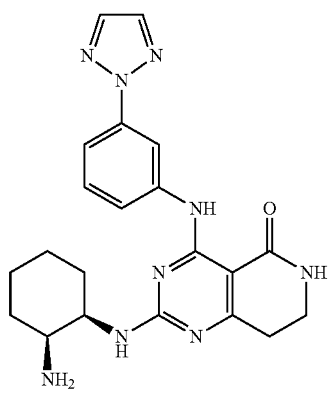 [SMILES: N[C@H]1CCCC[C@H]1Nc1nc2c(c(Nc3cccc(-n4nccn4)c3)n1)C(=O)NCC2] | 4-((3-(2H-1,2,3-triazol-2-yl)phenyl)amino)-2-(((1R,2S)-2-aminocyclohexyl)amino)-7,8-dihydropyrido[4,3-d]pyrimidin-5(6H)-one |
| 7. | 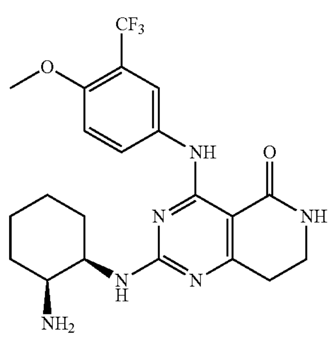 [SMILES: COc1ccc(Nc2nc(N[C@@H]3CCCC[C@@H]3N)nc3c2C(=O)NCC3)cc1C(F)(F)F] | 2-(((1R,2S)-2-aminocyclohexyl)amino)-4-((4-methoxy-3-(trifluoromethyl)phenyl)amino)-7,8-dihydropyrido[4,3-d]pyrimidin-5(6H)-one |
| 8. | 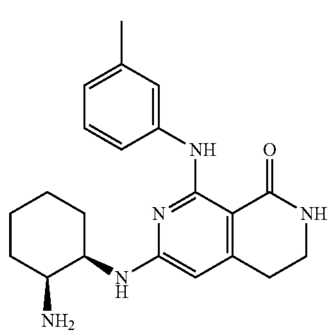 [SMILES: Cc1cccc(Nc2nc(N[C@@H]3CCCC[C@@H]3N)cc3c2C(=O)NCC3)c1] | 6-(((1R,2S)-2-aminocyclohexyl)amino)-8-(m-tolylamino)-3,4-dihydro-2,7-naphthyridin-1(2H)-one |

TABLE 1-continued

Structures of Kinase Inhibitors

| EXAMPLE NO. | STRUCTURE | NAME |
|---|---|---|
| 9. | 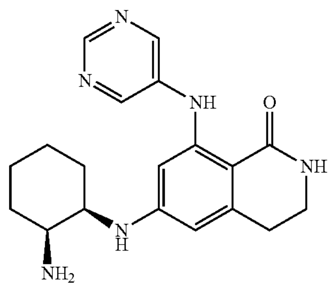 | 6-(((1R,2S)-2-aminocyclohexyl)amino)-8-(pyrimidin-5-ylamino)-3,4-dihydroisoquinolin-1(2H)-one |
| 10. | 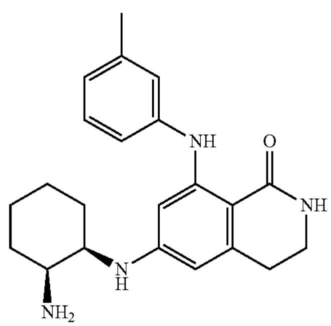 [SMILES: Cc1cccc(Nc2cc(N[C@@H]3CCCC[C@@H]3N)cc3c2C(=O)NCC3)c1] | 6-(((1R,2S)-2-aminocyclohexyl)amino)-8-(m-tolylamino)-3,4-dihydroisoquinolin-1(2H)-one |
| 11. | 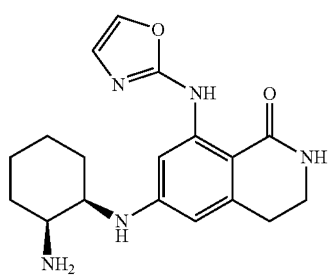 [SMILES: N[C@H]1CCCC[C@H]1Nc1cc2c(c(Nc3ncco3)c1)C(=O)NCC2] | 6-(((1R,2S)-2-aminocyclohexyl)amino)-8-(oxazol-2-ylamino)-3,4-dihydroisoquinolin-1(2H)-one |
| 12. | 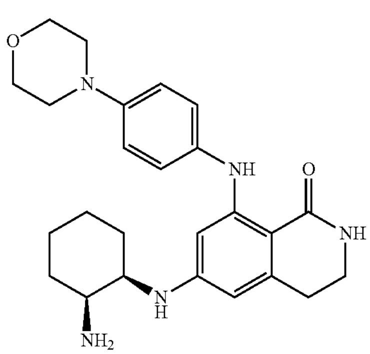 [SMILES: N[C@H]1CCCC[C@H]1Nc1cc2c(c(Nc3ccc(N4CCOCC4)cc3)c1)C(=O)NCC2] | 6-(((1R,2S)-2-aminocyclohexyl)amino)-8-((4-morpholinophenyl)amino)-3,4-dihydroisoquinolin-1(2H)-one |

TABLE 1-continued

Structures of Kinase Inhibitors

| EXAMPLE NO. | STRUCTURE | NAME |
|---|---|---|
| 13. | 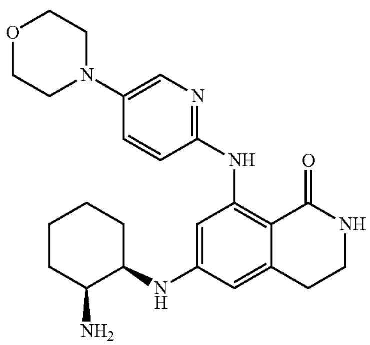 [SMILES: N[C@H]1CCCC[C@H]1Nc1cc2c(c(Nc3ccc(N4CCOCC4)cn3)c1)C(=O)NCC2] | 6-(((1R,2S)-2-aminocyclohexyl)amino)-8-((5-morpholinopyridin-2-yl)amino)-3,4-dihydroisoquinolin-1(2H)-one |
| 14. | 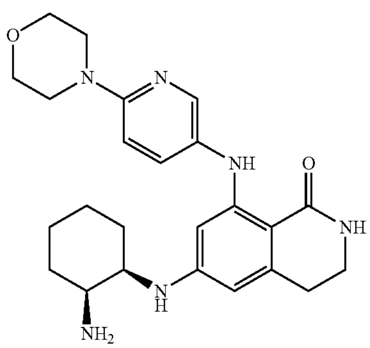 | 6-(((1R,2S)-2-aminocyclohexyl)amino)-8-((6-morpholinopyridin-3-yl)amino)-3,4-dihydroisoquinolin-1(2H)-one |
| 15. | 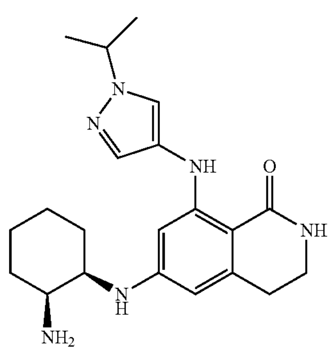 [SMILES: CC(C)n1cc(Nc2cc(N[C@@H]3CCCC[C@@H]3N)cc3c2C(=O)NCC3)cn1] | 6-(((1R,2S)-2-aminocyclohexyl)amino)-8-((1-isopropyl-1H-pyrazol-4-yl)amino)-3,4-dihydroisoquinolin-1(2H)-one |
| 16. | 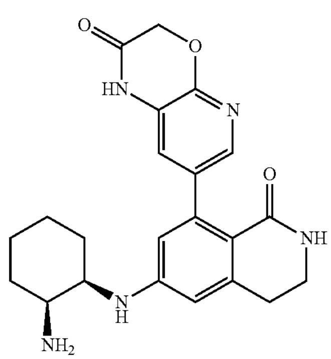 [SMILES: N[C@H]1CCCC[C@H]1Nc1cc2c(c(-c3cnc4c(c3)NC(=O)CO4)c1)C(=O)NCC2] | 7-(6-(((1R,2S)-2-aminocyclohexyl)amino)-1-oxo-1,2,3,4-tetrahydroisoquinolin-8-yl)-1H-pyrido[2,3-b][1,4]oxazin-2(3H)-one |

TABLE 1-continued

Structures of Kinase Inhibitors

| EXAMPLE NO. | STRUCTURE | NAME |
|---|---|---|
| 17. | 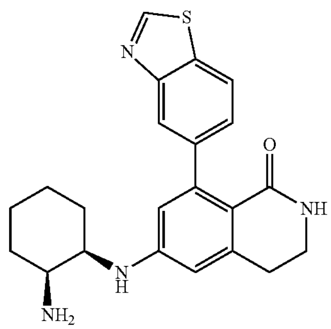 [SMILES: N[C@H]1CCCC[C@H]1Nc1cc2c(c(-c3ccc4scnc4c3)c1)C(=O)NCC2] | 6-(((1R,2S)-2-aminocyclohexyl)amino)-8-(benzo[d]thiazol-5-yl)-3,4-dihydroisoquinolin-1(2H)-one |
| 18. | 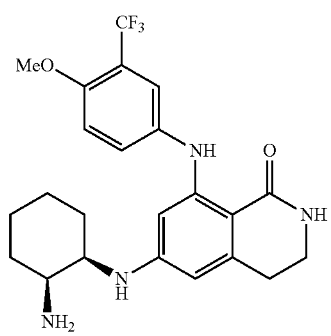 | 6-(((1R,2S)-2-aminocyclohexyl)amino)-8-((4-methoxy-3-(trifluoromethyl)phenyl)amino)-3,4-dihydroisoquinolin-1(2H)-one |
| 19. | 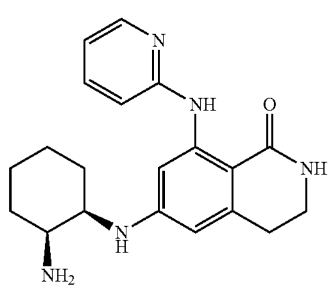 [SMILES: N[C@H]1CCCC[C@H]1Nc1cc2c(c(Nc3ccccn3)c1)C(=O)NCC2] | 6-(((1R,2S)-2-aminocyclohexyl)amino)-8-(pyridin-2-ylamino)-3,4-dihydroisoquinolin-1(2H)-one |
| 20. | 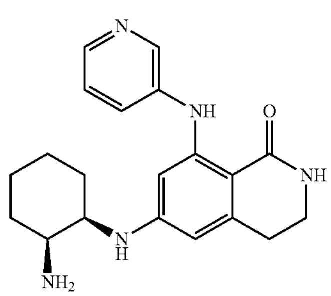 [SMILES: N[C@H]1CCCC[C@H]1Nc1cc2c(c(Nc3cccnc3)c1)C(=O)NCC2] | 6-(((1R,2S)-2-aminocyclohexyl)amino)-8-(pyridin-3-ylamino)-3,4-dihydroisoquinolin-1(2H)-one |

TABLE 1-continued

Structures of Kinase Inhibitors

| EXAMPLE NO. | STRUCTURE | NAME |
|---|---|---|
| 21. | 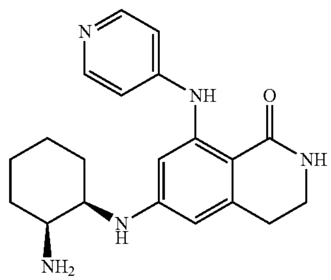 [SMILES: N[C@H]1CCCC[C@H]1Nc1cc2c(c(Nc3ccncc3)c1)C(=O)NCC2] | 6-(((1R,2S)-2-aminocyclohexyl)amino)-8-(pyridin-4-ylamino)-3,4-dihydroisoquinolin-1(2H)-one |
| 22. | 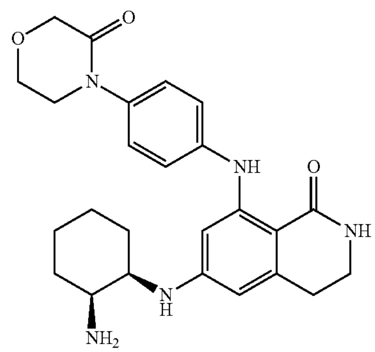 [SMILES: N[C@H]1CCCC[C@H]1Nc1cc2c(c(Nc3ccc(N4CCOCC4=O)cc3)c1)C(=O)NCC2] | 4-(4-((6-(((1R,2S)-2-aminocyclohexyl)amino)-1-oxo-1,2,3,4-tetrahydroisoquinolin-8-yl)amino)phenyl)morpholin-3-one |
| 23. | 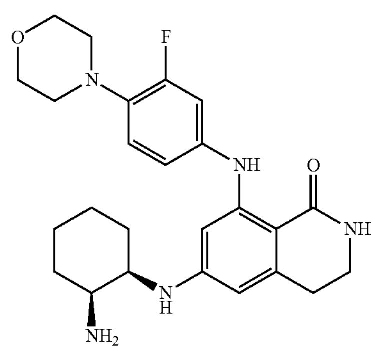 [SMILES: N[C@H]1CCCC[C@H]1Nc1cc2c(c(Nc3ccc(N4CCOCC4)c(F)c3)c1)C(=O)NCC2] | 6-(((1R,2S)-2-aminocyclohexyl)amino)-8-((3-fluoro-4-morpholinophenyl)amino)-3,4-dihydroisoquinolin-1(2H)-one |
| 24. | 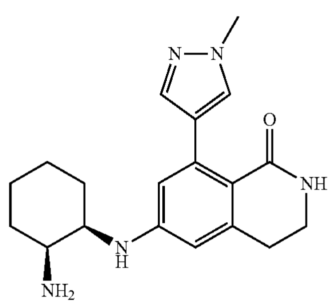 [SMILES: Cn1cc(-c2cc(N[C@@H]3CCCC[C@@H]3N)cc3c2C(=O)NCC3)cn1] | 6-(((1R,2S)-2-aminocyclohexyl)amino)-8-(1-methyl-1H-pyrazol-4-yl)-3,4-dihydroisoquinolin-1(2H)-one |

TABLE 1-continued

Structures of Kinase Inhibitors

| EXAMPLE NO. | STRUCTURE | NAME |
|---|---|---|
| 25. | 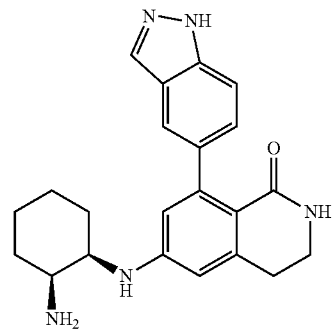 [SMILES: N[C@H]1CCCC[C@H]1Nc1cc2c(c(-c3ccc4[nH]ncc4c3)c1)C(=O)NCC2] | 6-(((1R,2S)-2-aminocyclohexyl)amino)-8-(1H-indazol-5-yl)-3,4-dihydroisoquinolin-1(2H)-one |
| 26. | 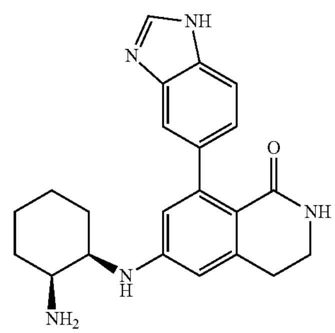 [SMILES: N[C@H]1CCCC[C@H]1Nc1cc2c(c(-c3ccc4[nH]cnc4c3)c1)C(=O)NCC2] | 6-(((1R,2S)-2-aminocyclohexyl)amino)-8-(1H-benzo[d]imidazol-5-yl)-3,4-dihydroisoquinolin-1(2H)-one |
| 27. | 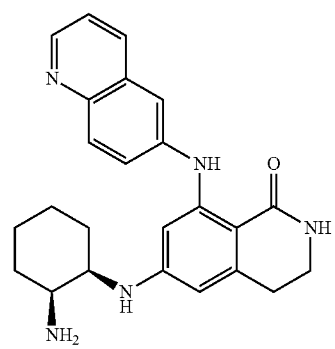 [SMILES: N[C@H]1CCCC[C@H]1Nc1cc2c(c(Nc3ccc4ncccc4c3)c1)C(=O)NCC2] | 6-(((1R,2S)-2-aminocyclohexyl)amino)-8-(quinolin-6-ylamino)-3,4-dihydroisoquinolin-1(2H)-one |
| 28. | 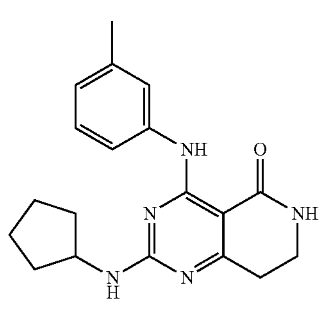 [SMILES: Cc1cccc(Nc2nc(NC3CCCC3)nc3c2C(=O)NCC3)c1] | 2-(cyclopentylamino)-4-(m-tolylamino)-7,8-dihydropyrido[4,3-d]pyrimidin-5(6H)-one |

TABLE 1-continued

Structures of Kinase Inhibitors

| EXAMPLE NO. | STRUCTURE | NAME |
|---|---|---|
| 29. | 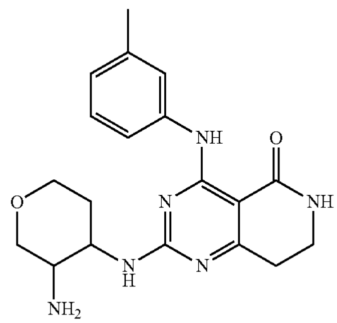 [SMILES: Cc1cccc(Nc2nc(NC3CCOCC3N)nc3c2C(=O)NCC3)c1] | 2-((3-aminotetrahydro-2H-pyran-4-yl)amino)-4-(m-tolylamino)-7,8-dihydropyrido[4,3-d]pyrimidin-5(6H)-one |
| 30. | 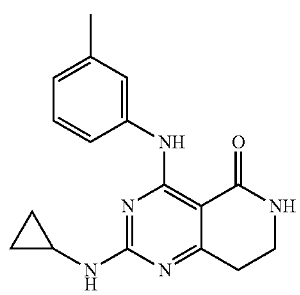 [SMILES: Cc1cccc(Nc2nc(NC3CC3)nc3c2C(=O)NCC3)c1] | 2-(cyclopropylamino)-4-(m-tolylamino)-7,8-dihydropyrido[4,3-d]pyrimidin-5(6H)-one |
| 31. | 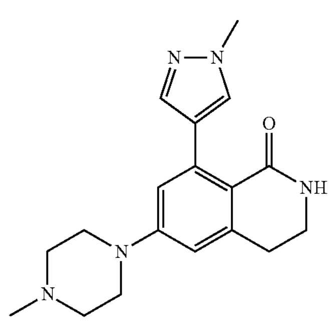 [SMILES: CN1CCN(c2cc3c(c(-c4cnn(C)c4)c2)C(=O)NCC3)CC1] | 8-(1-methyl-1H-pyrazol-4-yl)-6-(4-methylpiperazin-1-yl)-3,4-dihydroisoquinolin-1(2H)-one |
| 32. | 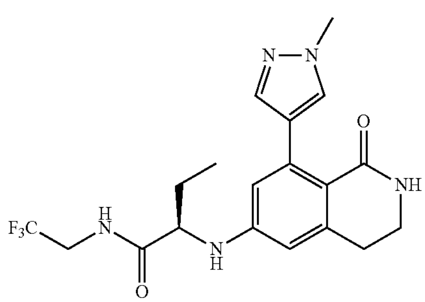 [SMILES: CC[C@@H](Nc1cc2c(c(-c3cnn(C)c3)c1)C(=O)NCC2)C(=O)NCC(F)(F)F] | (R)-2-(8-(1-methyl-1H-pyrazol-4-yl)-1-oxo-1,2,3,4-tetrahydroisoquinolin-6-ylamino)-N-(2,2,2-trifluoroethyl)butanamide |

TABLE 1-continued

Structures of Kinase Inhibitors

| EXAMPLE NO. | STRUCTURE | NAME |
|---|---|---|
| 33. | 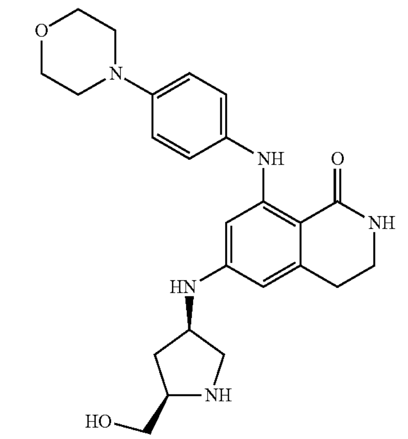 [SMILES: O=C1NCCc2cc(N[C@H]3CN[C@@H](CO)C3)cc(Nc3ccc(N4CCOCC4)cc3)c21] | 6-((3R,5R)-5-(hydroxymethyl)pyrrolidin-3-ylamino)-8-(4-morpholinophenylamino)-3,4-dihydroisoquinolin-1(2H)-one |

In one group of embodiments, the compounds, tautomers thereof, or salts thereof provided herein are in purified forms.

In one group of embodiments, provided is a pharmaceutical composition comprising a compound of any of the above embodiments or a tautomer or pharmaceutically acceptable salt thereof.

The compounds of the present invention may be prepared by known organic synthesis techniques, including the methods described in more detail in the Examples. By way of example, in one group of embodiments, compounds of formula (I) wherein $G^1$ and $G^2$ are both C—X are prepared as described in Scheme 1 below.

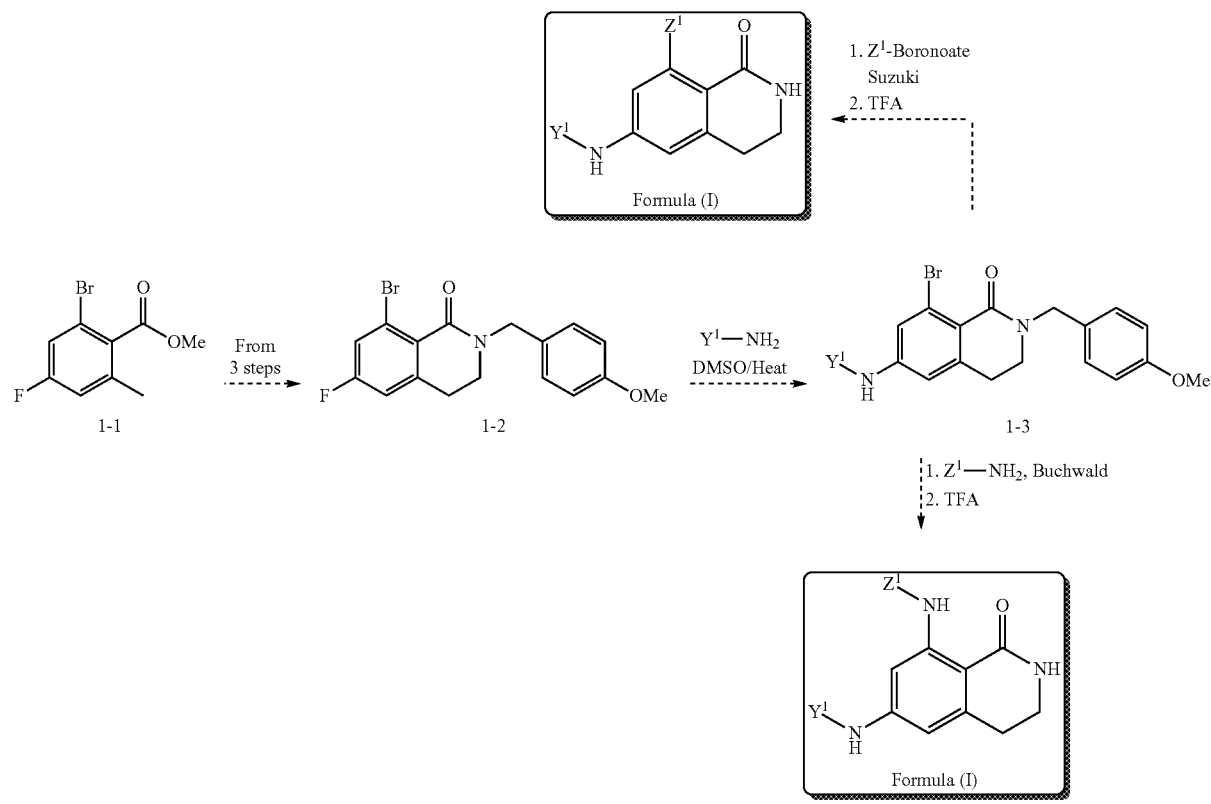

Figure 2:
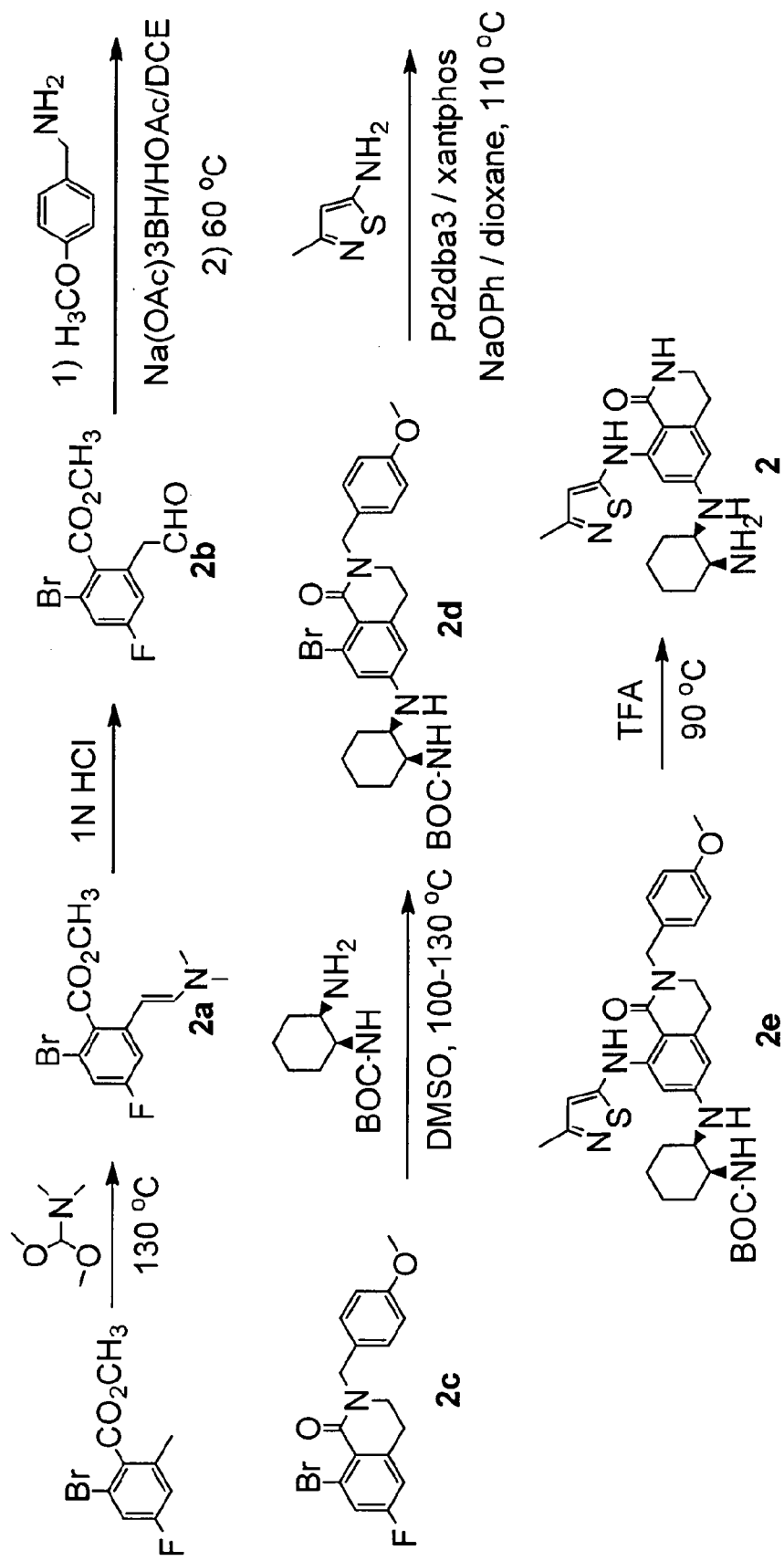
FIG. 2 shows a synthetic route for the preparation of 6-(((1R,2S)-2-aminocyclohexyl)amino)-8-((3-methylisothiazol-5-yl)amino)-3,4-dihydroisoquinolin-1(2H)-one (2).

Starting with compound 1-1, a three step procedure provides the protected compound 1-2 as described in the Examples section and FIG. 1 and FIG. 2. Fluoride displacement provides compound 1-3. Compound 1-3 is converted to compounds of formula (I) using either a Suzukin coupling with a suitable boronoate, or a Buchwald coupling using a suitable amine. Other coupling procedures may also be used and are contemplated within the scope of embodiments presented herein.

By way of example, in one group of embodiments, compounds of formula (I) wherein $G^1$ and $G^2$ are both N are prepared as described in Scheme 2 below.

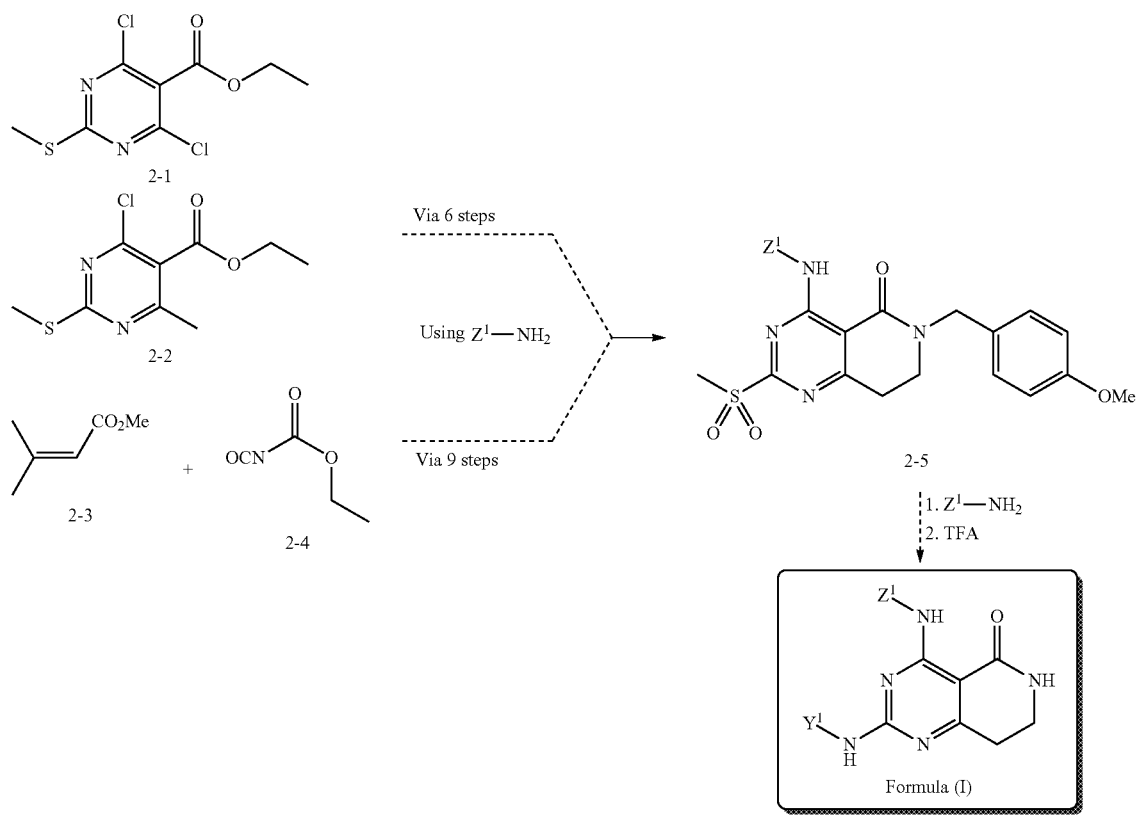

Starting with either compound 2-1 (See FIG. 5 and FIG. 7), or 2-2 (See FIG. 6 or FIG. 8) or a mixture of compounds 2-3 and 2-4 (See FIG. 4), a sequence of steps described in the examples section provides an intermediate of structure 2-5. Compound 2-5 is then converted to compounds of formula (I) using a Buchwald coupling procedure. Other coupling procedures known in the art are also contemplated within the scope of embodiments presented herein.

In one group of embodiments, provided is an intermediate compound used in the preparation of the compounds disclosed herein.

In one group of embodiments, provided are methods for preparing the compounds disclosed herein.

In one group of embodiments, certain of the compounds disclosed herein may generally be utilized as the free base. Alternatively, certain of the compounds may be used in the form of acid addition salts.

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

Utility

The compounds disclosed herein have utility over a wide range of therapeutic applications, and may be used to treat a variety of conditions, mediated at least in part by JAK or Syk kinase. For example, such conditions include, but are not limited to, those associated with cardiovascular disease, inflammatory disease, autoimmune disease, or a cell proliferative disorder.

Cardiovascular diseases are include but are not limited to restenosis, thrombosis, immune thrombocytopenic purpura, heparin induced thrombocytopenia, dilated cardiomyopathy, sickle cell disease, atherosclerosis, myocardial infarction, vascular inflammation, unstable angina, and acute coronary syndromes.

Inflammatory diseases include but are not limited to allergy, asthma, rheumatoid arthritis, B Cell mediated diseases, Non-Hodgkin's Lymphoma, anti-phospholipid syndrome, lupus, psoriasis, multiple sclerosis, and end stage renal disease.

Autoimmune disease include but are not limited to hemolytic anemia, immune thrombocytopenic purpura, multiple sclerosis, Sjogren's syndrome, diabetes, rheumatoid arthritis, lupus, and psoriasis.

Cell proliferative disorders include but are not limited to leukemia, a lymphoma, myeloproliferative disorders, hematological malignancies, and chronic idiopathic myelofibrosis.

In one group of embodiments, provided is a method for inhibiting the JAK or Syk activity of a blood sample comprising contacting said sample with a compound or a pharmaceutically acceptable salt thereof as disclosed herein.

Compositions and Methods of Administration

Depending on the intended mode of administration, the pharmaceutical compositions may be in the form of solid, semi-solid or liquid dosage forms, preferably in unit dosage form suitable for single administration of a precise dosage. In addition to an effective amount of the active compound(s), the compositions may contain suitable pharmaceutically-acceptable excipients, including adjuvants which facilitate processing of the active compounds into preparations which can be used pharmaceutically.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

The term "administering" refers to administration by any route, including parenteral and transmucosal (e.g., buccal, sublingual, palatal, gingival, nasal, vaginal, rectal, or transdermal).

For oral administration, the composition will generally take the form of a tablet or capsule, or it may be an aqueous or nonaqueous solution, suspension, or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral formulation include preservatives, suspending agents, thickening agents, and the like.

Injectable formulations can be prepared in conventional forms, either as liquid solutions or suspensions, solid forms suitable for solubilization or suspension in liquid prior to injection, or as emulsions or liposomal formulations. The sterile injectable formulation may also be a sterile injectable solution or a suspension in a nontoxic parenterally acceptable diluent or solvent. Among the acceptable vehicles and solvents that may be employed are water, Ringer's solution, and isotonic sodium chloride solution. In addition, sterile, fixed oils, fatty esters or polyols are conventionally employed as solvents or suspending media.

The pharmaceutical compositions of this invention may also be formulated in lyophilized form for parenteral administration. Lyophilized formulations may be reconstituted by addition of water or other aqueous medium and then further diluted with a suitable diluent prior to use. The liquid formulation is generally a buffered, isotonic, aqueous solution. Examples of suitable diluents are isotonic saline solution, 5% dextrose in water, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of the indicated disease.

The pharmaceutical composition may additionally contain one or more other pharmacologically active agents in addition to a compound of this invention.

Dosage forms containing effective amounts of the modulators are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

EXAMPLES

The following examples are offered to illustrate, but not to limit, the claimed invention.

Preparative Examples

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Compounds of Formula I can be synthesized by a variety of methods, including the route outlined in FIG. 1. In general, the methods include formation of the fused bicyclic 10-membered core and attachment of substituents to the core. As shown in FIG. 1, for example, enamine 1a can be derived from a suitable starting material (such as an o-toluate derivative) and converted to aldehyde 1b. Reductive amination of aldehyde 1b with a protected amine, followed by amide bond formation, provides the bicycle 1c for further elaboration. Nucleophilic addition of a functionalized amine $NH_2-Y^1$ and cross-coupling of an aromatic species $Z^1$-L-A can be conducted in any order to form the protected product 1e. Global deprotection affords the desired product.

Figure 3:
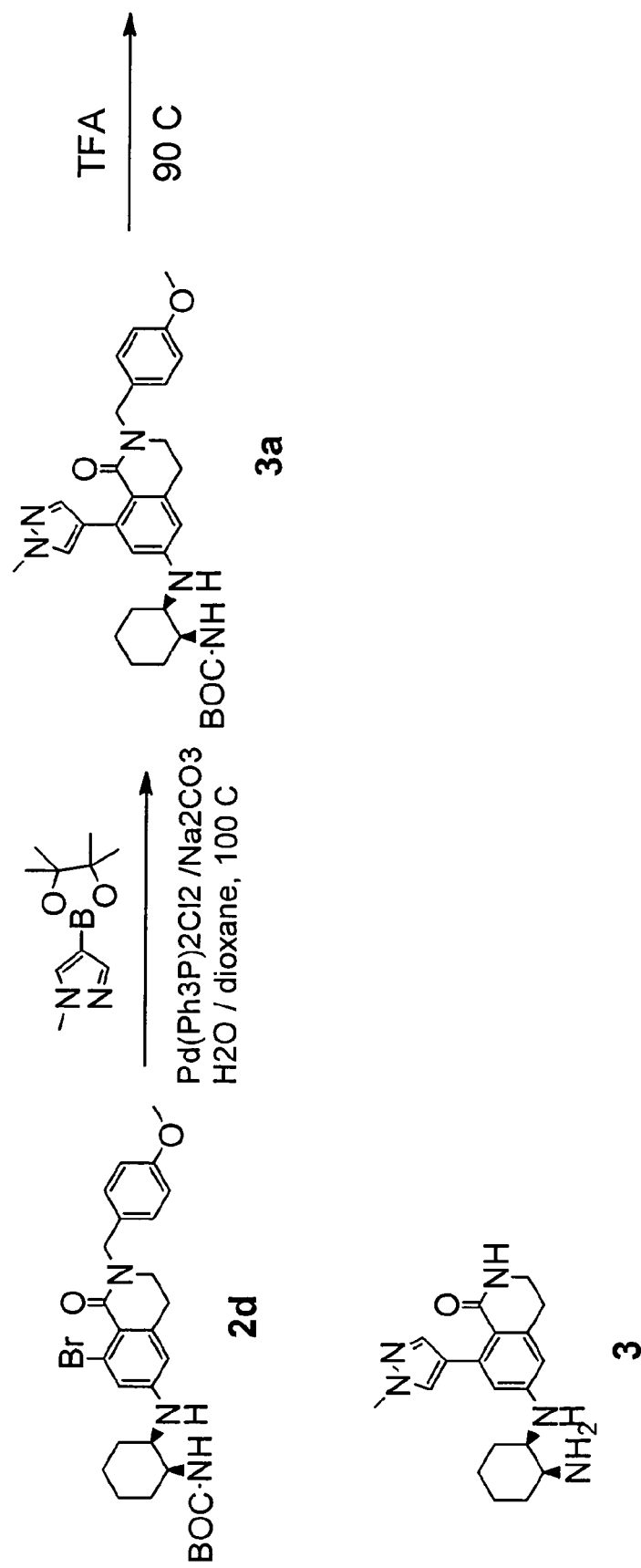
FIG. 3 shows a synthetic route for the preparation of 6-(((1R,2S)-2-aminocyclohexyl)amino)-8-(1-methyl-1H-pyrazol-4-yl)-3,4-dihydroisoquinolin-1(2H)-one (3).

FIG. 2 and FIG. 3 show the synthesis of heterocycles 2 and 3 from common precursors. In particular, methyl (2-bromo-3-fluoro-5-methyl)benzoate is converted to aldehyde 2b via enamine 2a. The reductive amination/condensation sequence is conducted with p-methoxybenzylamine to provide bicycle 2c, which is subsequently converted to Boc-protected diaminocylcohexane derivative 2d. This common intermediate can be further elaborated via Buchwald-Hartwig coupling, as shown in FIG. 2, or via Suzuki coupling, as shown in FIG. 3, to provide compounds 2 and 3, respectively.

Example 1

2-((1R,2S)-2-aminocyclohexylamino)-4-(m-tolylamino)-7,8-dihydropyrido[4,3-d]pyrimidin-5(6H)-one

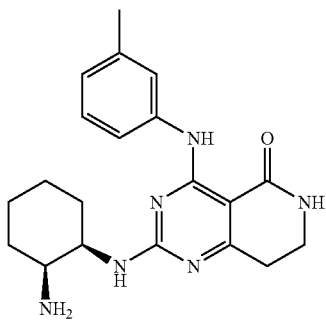 [SMILES: Cc1cccc(Nc2nc(N[C@@H]3CCCC[C@@H]3N)nc3c2C(=O)NCC3)c1]

Figure 4:
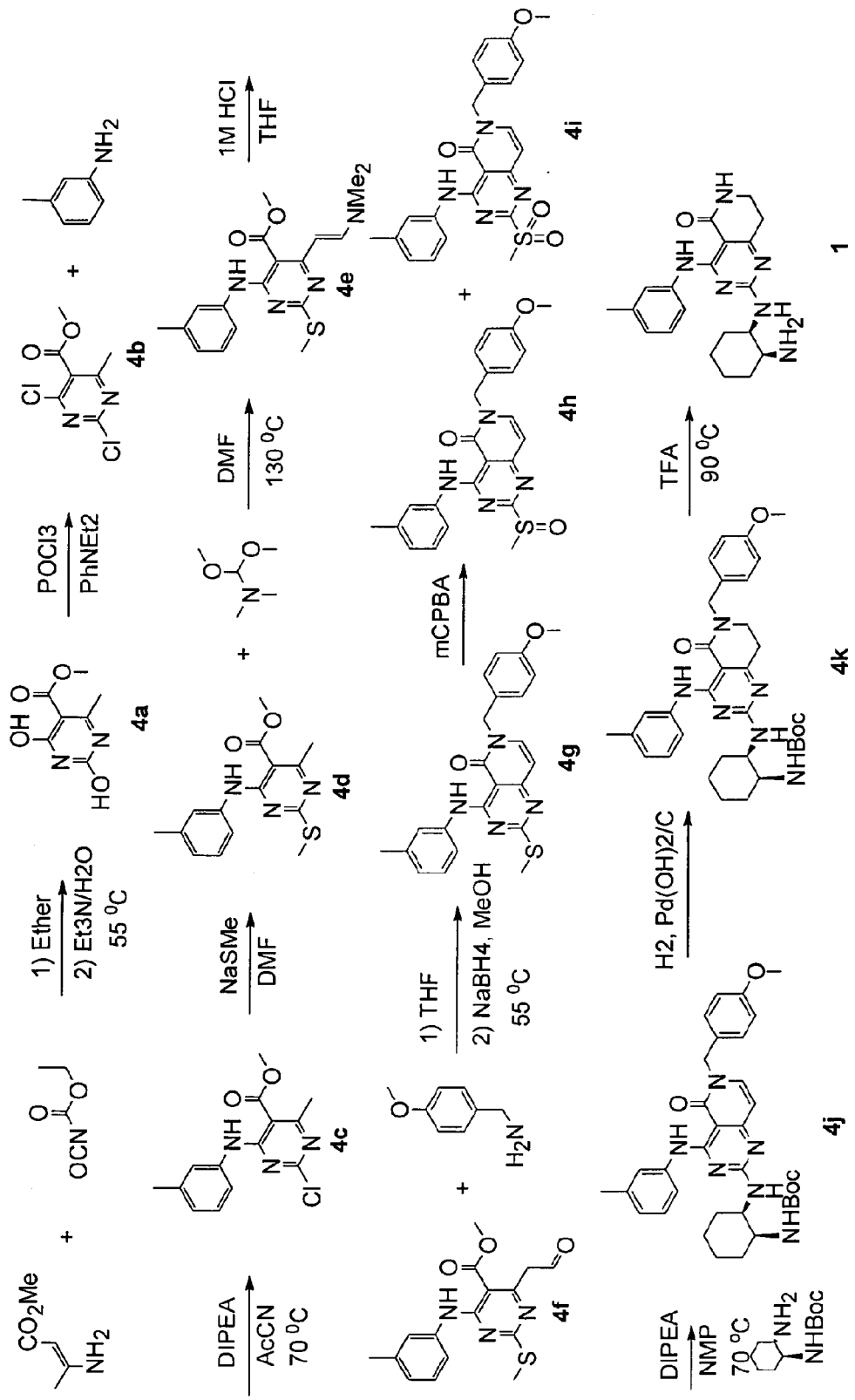
FIG. 4 shows a synthetic route for the preparation of 2-((1R,2S)-2-aminocyclohexylamino)-4-(m-tolylamino)-7,8-dihydropyrido[4,3-d]pyrimidin-5(6H)-one (1).

The title compound 1 was synthesized as shown in FIG. 4.

Methyl 2,4-dihydroxy-6-methylpyrimidine-5-carboxylate (4a)

To a suspension of (E)-methyl 3-aminobut-2-enoate (1.8 g, 15.64 mmol) in diethyl ether (9 mL) at 0° C. was added ethyl carbonisocyanatidate (2 g, 15.64 mmol) in ether (2 mL) under argon. The resulting pale yellow suspension was stirred for 4 h and the solid was collected by filtration to give corresponding intermediate (1.15 g), which was dissolved in 25% aqueous Et3N (8 ml), and was heated at 55° C. for 15 h, solvent was removed by rotavap, and the residue was acidified with AcOH, the resulting precipitate was collected by filtration to give 4a (700 mg).

Methyl 2,4-dichloro-6-methylpyrimidine-5-carboxylate (4b)

To a mixture of methyl 2,4-dihydroxy-6-methylpyrimidine-5-carboxylate (700 mg, 3.80 mmol) in POCl3 (7 mL) was added N,N-diethylaniline (1 ml, 5.71 mmol), after heated at 95° C. for 3 h, the mixture was concentrated to remove most of the POCl3, the remaining solution was poured over to ice water and Sat. NaHCO3, the aqueous layer was extracted with EtOAc, organic layer was separated, dried and concentrated to give crude oil, which was purified by column chromatography (Hexanes/EtOAc=4:1) to give 4b (680 mg).

Methyl 2-chloro-4-methyl-6-(m-tolylamino)pyrimidine-5-carboxylate (4c)

To a solution of methyl 2,4-dichloro-6-methylpyrimidine-5-carboxylate (300 mg, 1.36 mmol) in AcCN (3 ml) was added m-toluidine (161 mg, 1.50 mmol) and DIPEA (0.484 mL, 2.72 mmol). After heated at 70° C. for 1 h, the mixture was cooled and concentrated to dryness, then it was diluted with water, the resulting precipitated was collected by filtration to give (480 mg).

Methyl 4-methyl-2-(methylthio)-6-(m-tolylamino)pyrimidine-5-carboxylate (4d)

To a solution of methyl 2-chloro-4-methyl-6-(m-tolylamino)pyrimidine-5-carboxylate (408 mg, 1.40 mmol) in DMF (3 mL) was added NaSMe (108 mg, 1.54 mmol). The solution was stirred at room temperature for 15 h, and heated at 65° C. for 2 h. The mixture was quenched with water and extracted with EtOAc, organic layer was combined, washed with Sat. NaHCO3, brine, dried and concentrated to give crude oil, which was purified by column chromatography to give 4d (250 mg).

(E)-Methyl 4-(2-(dimethylamino)vinyl)-2-(methylthio)-6-(m-tolylamino)pyrimidine-5-carboxylate (4e)

To a solution of methyl 4-methyl-2-(methylthio)-6-(m-tolylamino)pyrimidine-5-carboxylate (250 mg, 0.825 mmol) in DMF (1.5 mL) was added 1,1-dimethoxy-N,N-dimethylmethanamine (0.22 mL, 1.65 mmol). The mixture was heated at 130° C. for 2 h, poured into water, the aqueous layer was extracted with EtOAc. Organic layer was combined, washed with Sat. NaHCO3, brine, dried and concentrated to give 4e (260 mg).

Methyl 2-(methylthio)-4-(2-oxoethyl)-6-(m-tolylamino)pyrimidine-5-carboxylate (4f)

To a solution of (E)-methyl 4-(2-(dimethylamino)vinyl)-2-(methylthio)-6-(m-tolylamino)pyrimidine-5-carboxylate (100 mg, 0.28 mmol) in THF (1 mL) was added 1N HCl (1 mL). After stirring at ambient temperature for 1 h, it was diluted with EtOAc, organic layer was washed with brine, dried and concentrated to give as 4f crude oil.

6-(4-Methoxybenzyl)-2-(methylthio)-4-(m-tolylamino)pyrido[4,3-d]pyrimidin-5(6H)-one (4g)

To a solution of methyl 2-(methylthio)-4-(2-oxoethyl)-6-(m-tolylamino)pyrimidine-5-carboxylate (160 mg, 0.48 mmol) in DCM (2 mL) was added NaOAc, and the mixture was stirred at room temperature for 15, and concentrated to dryness. The residue was dissolved in THF (2 mL) and MeOH (2 mL), NaBH4 (a spatula tip) was added. After heating at 50° C. for 1 h, the mixture was cooled and concentrated, the residue was diluted with EtOAc, organic layer was washed with brine, dried and concentrated to give crude residue, which was purified by column chromatography to give 4g (84 mg).

6-(4-Methoxybenzyl)-2-(methylsulfinyl)-4-(m-tolylamino)pyrido[4,3-d]pyrimidin-5(6H)-one (4h)/6-(4-methoxybenzyl)-2-(methylsulfonyl)-4-(m-tolylamino)pyrido[4,3-d]pyrimidin-5(6H)-one (4i)

To a solution of 6-(4-methoxybenzyl)-2-(methylthio)-4-(m-tolylamino)pyrido[4,3-d]pyrimidin-5(6H)-one (84 mg, 0.20 mmol) in NMP (1 mL) was added mCPBA (58 mg, 0.22 mmol). After stirring at room temperature for 30 min, it was diluted with EtOAc, organic layer was washed with Sat. NaHCO3, brine, dried and concentrated to give a mixture of corresponding sulfoxide 4i and sulfone 4h (77 mg).

Tert-butyl (1S,2R)-2-(6-(4-methoxybenzyl)-5-oxo-4-(m-tolylamino)-5,6-dihydropyrido[4,3-d]pyrimidin-2-ylamino)cyclohexylcarbamate (4j)

To a solution of the above mentioned mixture of sulfoxide and sulfone in NMP (1 mL) was added tert-butyl (1S,2R)-2-aminocyclohexylcarbamate (44 mg, 0.2 mmol) and DIPEA (0.07 mL, 0.40 mmol). After heated at 70° C. for 3 h, the mixture was cooled and diluted with EtOAc, organic layer was washed with Sat. NaHCO3, brine, dried and concentrated to give 4j as crude product (50 mg).

Tert-butyl (1S,2R)-2-(6-(4-methoxybenzyl)-5-oxo-4-(m-tolylamino)-5,6,7,8-tetrahydropyrido[4,3-d]pyrimidin-2-ylamino)cyclohexylcarbamate (4k)

To a solution of tert-butyl (1S,2R)-2-(6-(4-methoxybenzyl)-5-oxo-4-(m-tolylamino)-5,6-dihydropyrido[4,3-d]pyrimidin-2-ylamino)cyclohexylcarbamate (50 mg) in EtOH (2 mL) and Dioxane (1.5 mL) was added Pd(OH)2/C (50 mg), then it was charged with H2 (1 atm), and stirred at room temperature for 2 days. Pd(OH)2/C was filtered off, and the filtrate was concentrated to give 4k.

2-((1R,2S)-2-aminocyclohexylamino)-4-(m-tolylamino)-7,8-dihydropyrido[4,3-d]pyrimidin-5(6H)-one (1)

A solution of the above mentioned crude product in TFA (0.5 mL) was heated at 100° C. for 3 h, cooled and concentrated to give crude oil, which was purified by preparative HPLC to give 1. MS found for $C_{19}H_{23}N_9O_2$ as $(M+H)^+$ 367.3, UV: $\lambda$=244.0, 292.6.

Example 2

Preparation of 2-(((1R,2S)-2-aminocyclohexyl)amino)-4-(m-tolylamino)-7,8-dihydropyrido[4,3-d]pyrimidin-5(6H)-one (Compound 1, alternate procedure)

In an alternate procedure, compound 1 was prepared according to the synthetic scheme illustrated below:

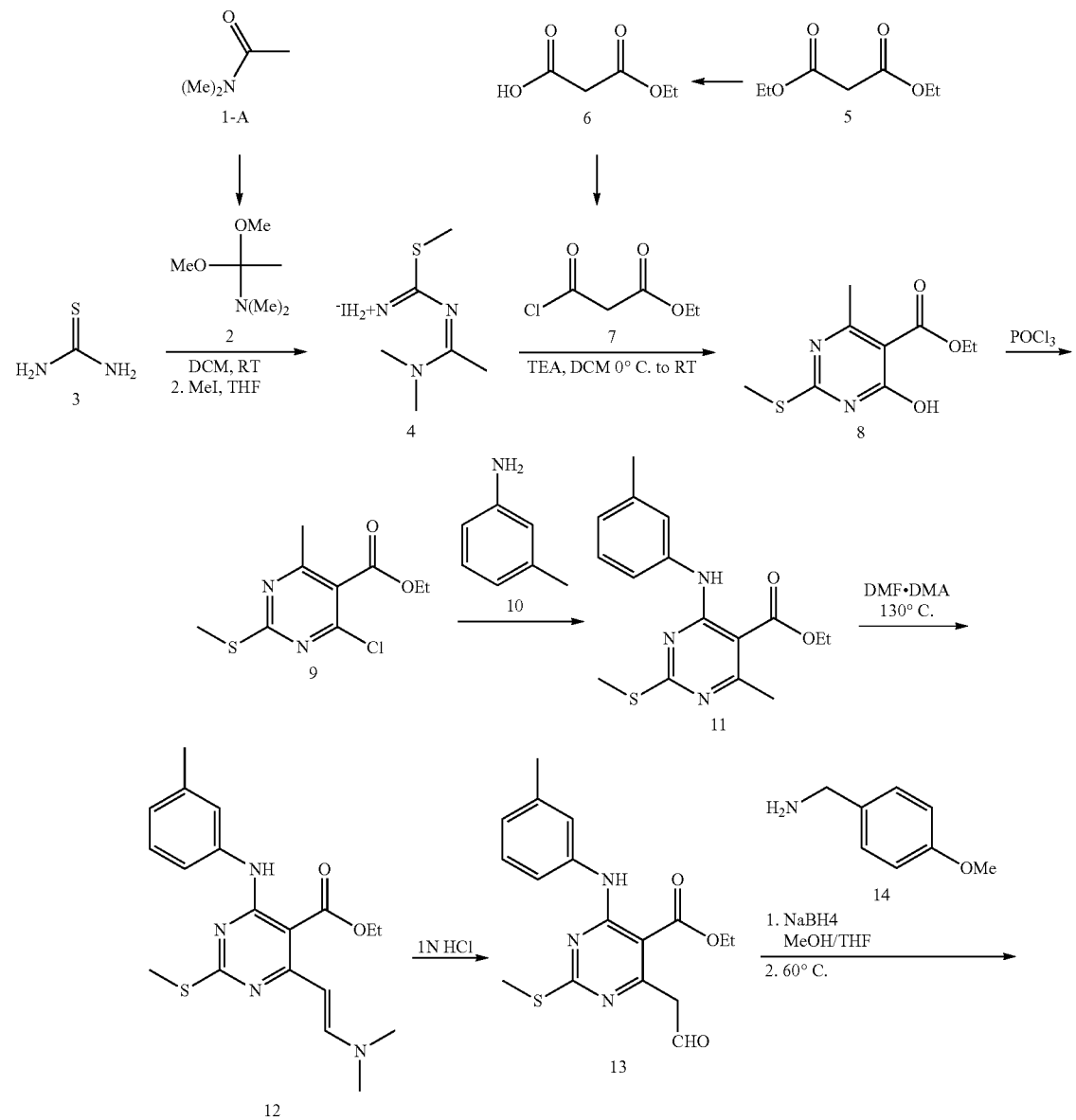

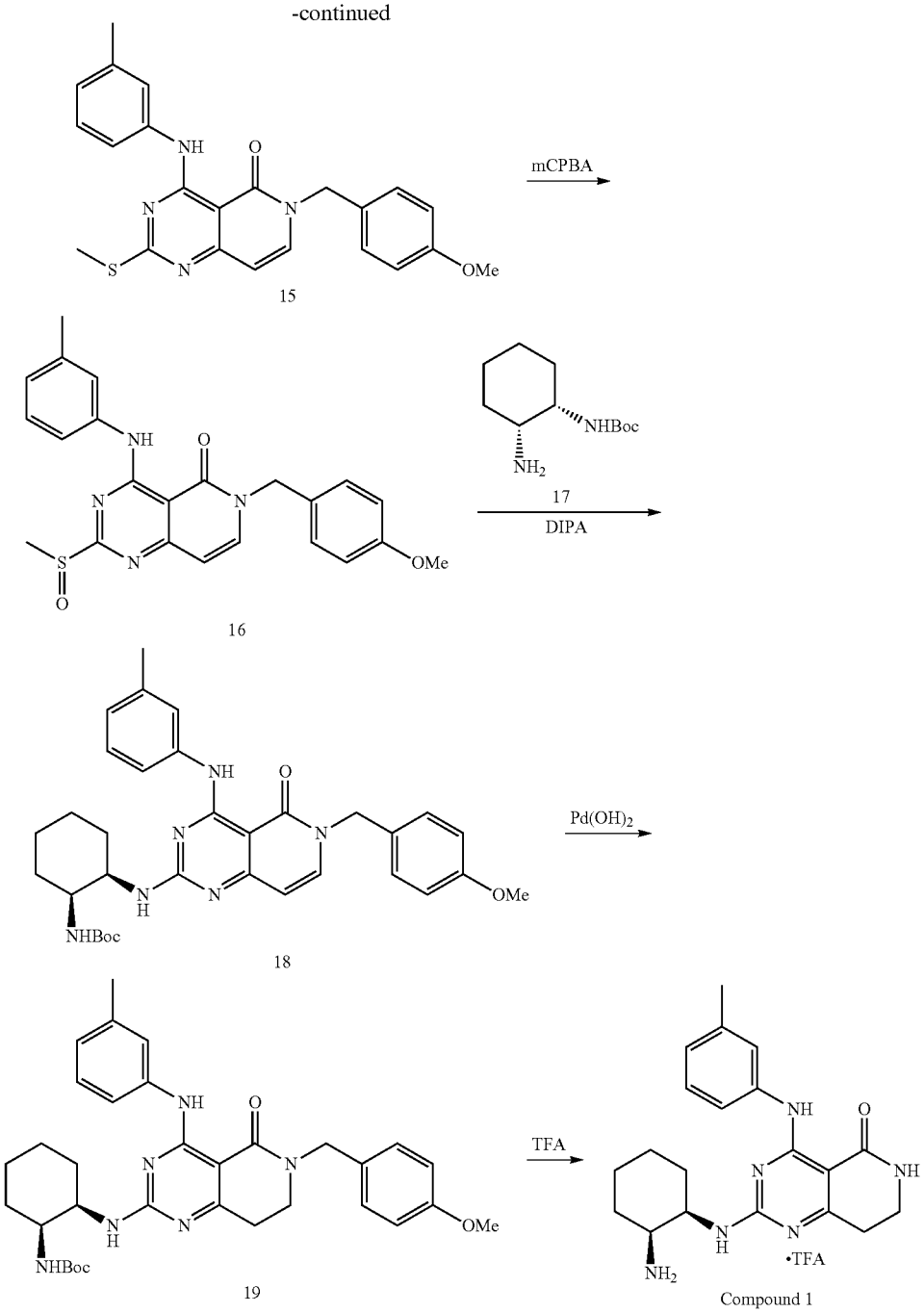

9 in the scheme above was synthesized according to the protocol described in WO 2011/053861 [PCT/US2010/054853].

Synthesis of 11:

To a solution of Ethyl 4-chloro-6-methyl-2-(methylthio) pyrimidine-5-carboxylate 9 (6 g, 0.244 mol) in NMP (30 mL) was added m-Toluidine 10 (3.93 g, 0.03673 mol), N-ethyl diisopropyl amine (12.6 mL, 0.07346 mol) and heated to 60° C. for 3 h. After completion of the reaction added water and extracted with ethyl acetate. The organic layer was separated and dried over anhydrous $Na_2SO_4$ and evaporated to obtain crude residue, which was washed with hexane to get 11 as a off white solid (5 g, 64.4% Yield).

$^1$HNMR (500 MHz, $CDCl_3$) δ ppm: 10.61 (s, 1H), 7.58-7.22 (m, 3H), 6.97 (d, 1H), 4.41 (q, 2H), 2.68 (s, 3H), 2.58 (s, 3H), 2.38 (s, 3H), 1.42 (t, 3H); Mass (m/z): 318.4 (M+H)

Synthesis of 12:

To a solution of ethyl 4-methyl-2-(methylthio)-6-(m-tolylamino) pyrimidine-5-carboxylate 11 (1 g, 3.15 mmol) in DMF (6 mL) was added 1,1-dimethoxy-N, N-dimethylmethanamine (0.83 mL, 6.30 mmol). The mixture was heated to 130° C. for 2 h, poured into water, the aqueous layer was extracted with Ethylacetate. The organic layer was washed with Sat.$NaHCO_3$, brine, dried over $Na_2SO_4$ and evaporated to get 12 as a brown solid (1.1 g, 94% Yield). Mass (m/z): 373.3 (M+H)

Synthesis of 13:

To solution of (E)-ethyl 4-(2-(dimethylamino)vinyl)-2-(methylthio)-6-(m-tolylamino)pyrimidine-5-carboxylate 12 (1.1 g, 2.956 mmol) in THF (8 mL) was added 1N HCl (8 mL) and stirred at ambient temperature for 1 h. After completion of the reaction, the reaction mixture was diluted with ethyl acetate, the organic layer was washed with brine, dried and evaporated to get crude 13 as a brown oily product (1 g). Mass (m/z): 346.4 (M+H).

Synthesis of 15:

To a mixture of ethyl 2-(methylthio)-4-(2-oxoethyl)-6-(m-tolylamino)pyrimidine-5-carboxylate 13 (1 g, 2.89 mmol) and 14 (0.5 mL, 3.47 mmol) in DCM (10 mL) was added NaOAc (180 mg, 2.195 mmol) and the mixture was stirred at room temperature for 15 h and concentrated to dryness. The residue was further dissolved in THF (8 mL), MeOH (8 mL) and NaBH$_4$ (340 mg, 8.947 mmol) was added. After heating at 50° C. for 1 h, the mixture was cooled to room temperature and concentrated to obtain solid residue, diluted with ethyl acetate and washed with brine, dried and concentrated to obtain crude product, which was purified by column chromatography to get 15 as a yellow solid (900 mg, 74% Yield). $^1$HNMR (500 MHz, CDCl$_3$) δ ppm: 11.91 (s, 1H), 7.68 (m, 2H), 7.38 (d, 1H), 7.25 (m, 3H), 6.98 (d, 1H), 6.91 (m, 2H), 6.41 (d, 1H), 5.10 (s, 2H), 3.80 (s, 3H), 2.61 (s, 3H), 2.38 (s, 3H); Mass (m/z): 419.3 (M+H)

Synthesis of 16:

To a solution of 6-(4-methoxybenzyl)-2-(methylthio)-N-m-tolyl-5,6-dihydropyrido[4,3-d]pyrimidin-4-amine 15 (1 g, 2.38 mmol) in DCM (10 mL) was added mCPBA (0.753 g, 2.86 mmol) at room temperature and stirred for 30 min. After completion of the reaction, the reaction mixture was diluted with DCM and washed with saturated NaHCO$_3$ solution and brine. The separated organic layer was dried over anhydrous Na$_2$SO$_4$ and concentrated to obtain 16 as a brown solid (900 mg, 90% Yield). Mass (m/z): 435.3 and 451.3 (M+H).

Synthesis of 18:

To a solution of 6-(4-methoxybenzyl)-2-(methylsulfinyl)-N-m-tolyl-5,6-dihydropyrido[4,3-d]pyrimidin-4-amine 16 (400 mg, 0.919 mmol) in NMP (5 mL) was added tert-butyl (1S,2R)-2-aminocyclohexylcarbamate, compound 17 (164 mg, 1.10 mmol)) followed by N-ethyl diisopropyl amine (0.31 ml, 1.83 mmol) and heated to 70° C. for 3 h. After completion of the reaction, diluted with the ethyl acetate, washed with water and saturated NaHCO$_3$. The separated organic layer was dried over anhydrous Na$_2$SO$_4$ and evaporated to obtain the crude product, which was purified by silica gel column chromatography to get 18 as a yellow solid (200 mg, 45% Yield). Mass (m/z): 484.4 (M+H)

Synthesis of 19:

To a solution of 6-(4-methoxybenzyl)-N2-((1S,2R)-2-methylcyclohexyl)-N4-m-tolyl-5,6-dihydropyrido[4,3-d]pyrimidine-2,4-diamine 18 (100 mg, 0.000207 mol) in a mixture of EtOH (4 mL) and 1,4-Dioxane (3 mL) was added Pd(OH)$_2$ and stirred under H$_2$ atm (Balloon pressure) for 48 h. After completion of the reaction, it was filtered through a celite bed and washed with ethyl acetate, concentrated under reduced pressure to obtain 19 as a brown solid (90 mg, 90% Yield). Mass (m/z): 486.4 (M+H)

Synthesis of Compound-1:

A mixture of 6-(4-methoxybenzyl)-N2-((1S,2R)-2-methylcyclohexyl)-N4-m-tolyl-5,6,7,8-tetrahydropyrido[4,3-d]pyrimidine-2,4-diamine 19 (90 mg, 0.000185 mol) and TFA (0.5 mL) was heated to 90° C. for 3 h. After completion of the reaction, the reaction mixture was evaporated under reduced pressure and the obtained crude residue was washed with isopropylether and dried to get Compound 1 as its TFA salt (60 mg, brown solid, 68% Yield). Mass (m/z): 367.3 (M+H).

Example 3

Synthesis of 2-(((1R,2S)-2-aminocyclohexyl)amino)-4-((1-methyl-1H-pyrazol-4-yl)amino)-7,8-dihydropyrido[4,3-d]pyrimidin-5(6H)-one (Compound 2)

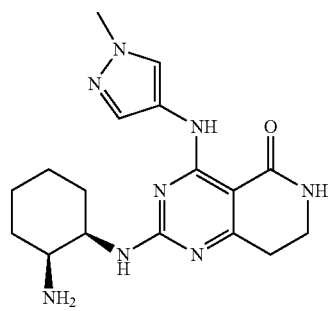 [SMILES: Cn1cc(Nc2nc(N[C@@H]3CCCC[C@@H]3N)nc3c2C(=O)NCC3)cn1]

The title compound was prepared according the scheme shown below.

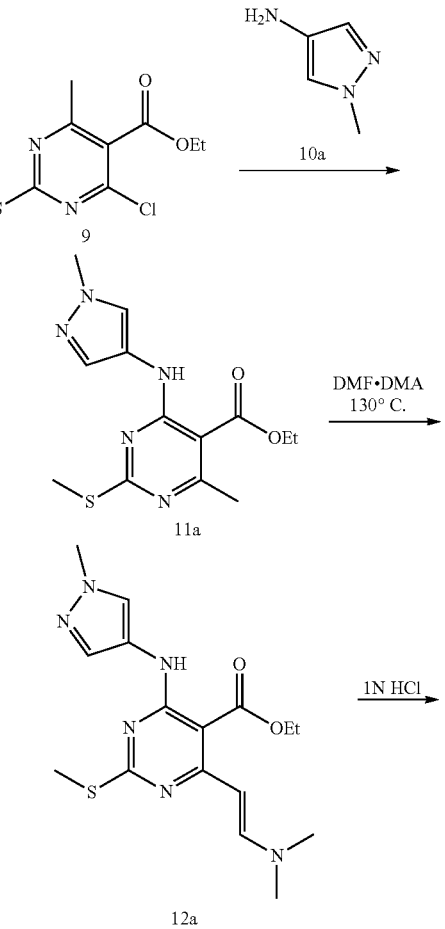

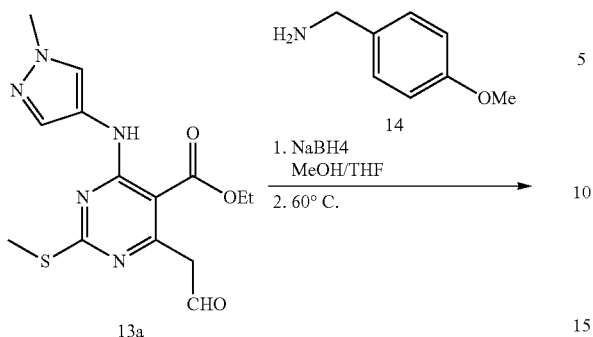

13a

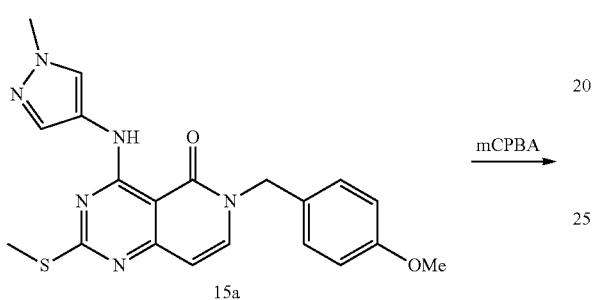

15a

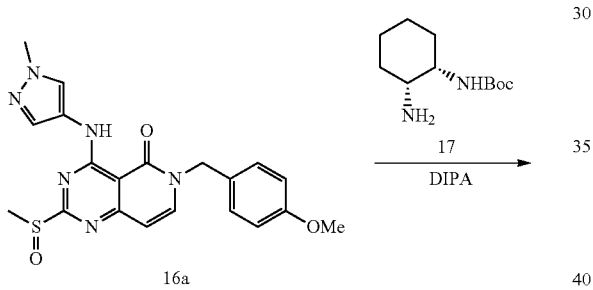

16a

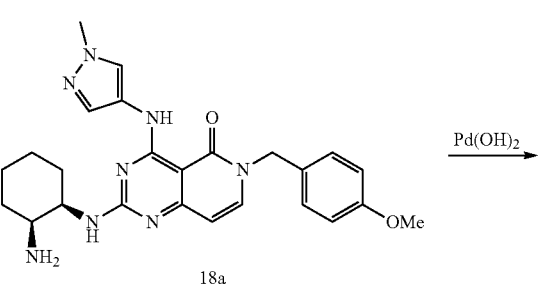

18a

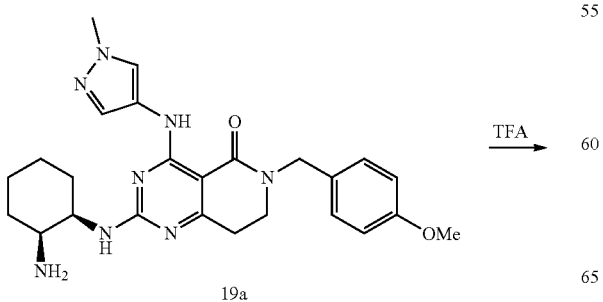

19a

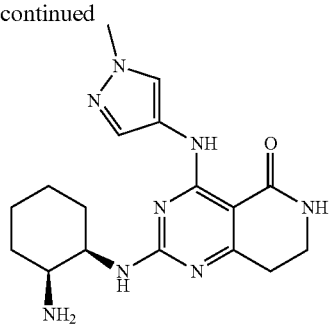

Compound-19a was prepared starting from −9 according to the experimental procedure described in Example 2. Deprotection provides the title compound.

Example 4

2-((1R,2S)-2-Aminocyclohexylamino)-4-(3-(pyrimidin-2-yl)phenylamino)-7,8-dihydropyrido[4,3-d]pyrimidin-5(6H)-one. (Compound 4)

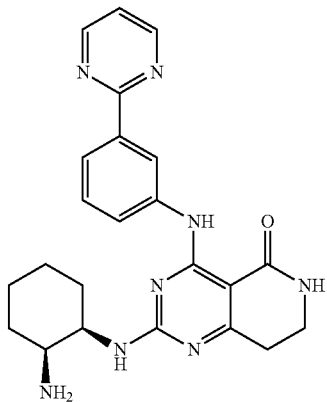 [SMILES: N[C@H]1CCCC[C@H]1Nc1nc2c(c(Nc3cccc(-c4ncccn4)c3)n1)C(=O)NCC2]

Figure 5:
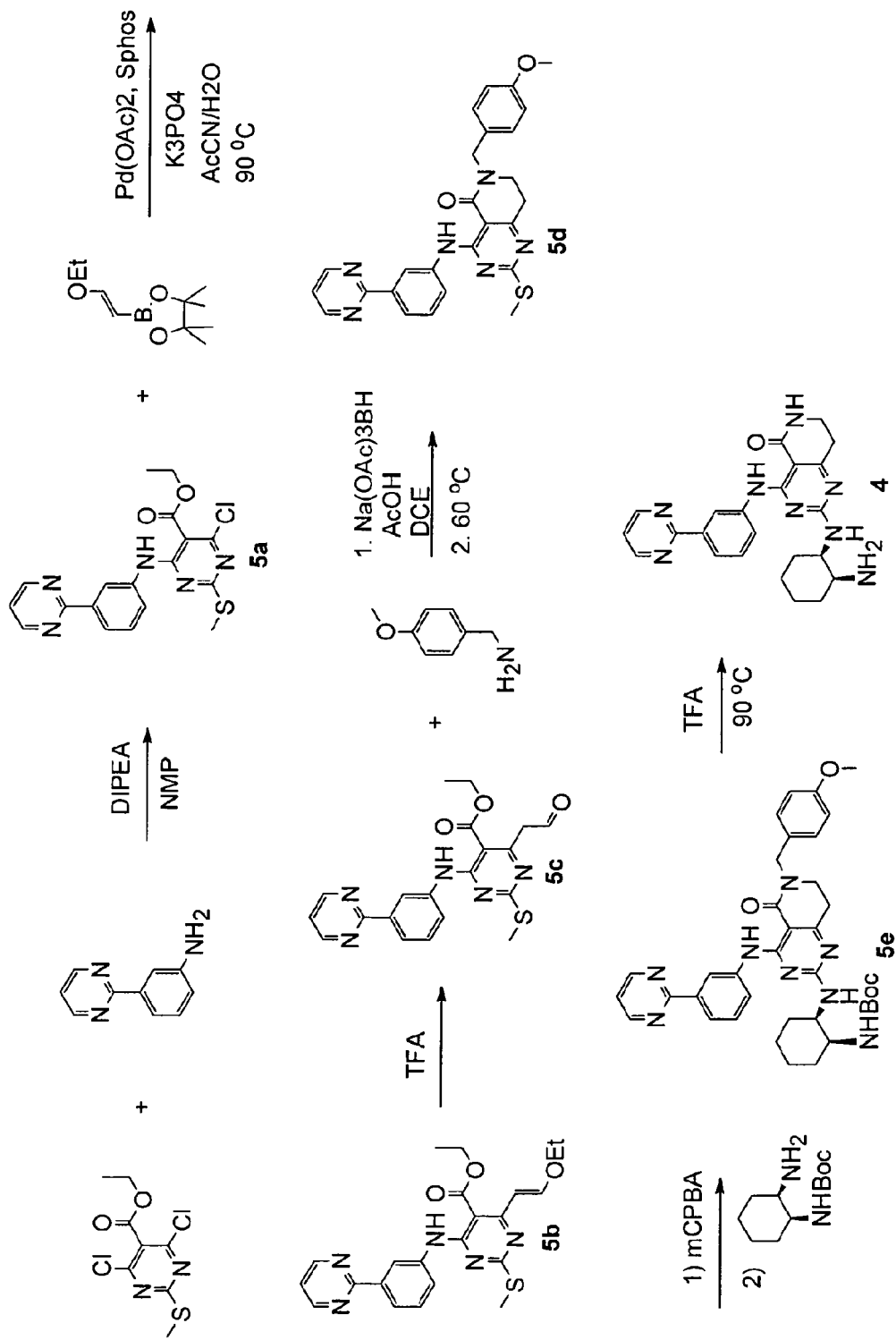
FIG. 5 shows a synthetic route for the preparation of 2-((1R,2S)-2-aminocyclohexylamino)-4-(3-(pyrimidin-2-yl)phenylamino)-7,8-dihydropyrido[4,3-d]pyrimidin-5(6H)-one (4).

The title compound 4 was synthesized as shown in FIG. 5.

Ethyl 4-chloro-2-(methylthio)-6-(3-(pyrimidin-2-yl)phenylamino)pyrimidine-5-carboxylate (5a). To a solution of ethyl 4,6-dichloro-2-(methylthio)pyrimidine-5-carboxylate (200 mg, 0.75 mmol) and 3-(pyrimidin-2-yl)aniline (140 mg, 0.825 mmol) in NMP (2 mL) was added DIPEA (0.161 mL, 0.9 mmol). After stirred at room temperature for 15 h, it was heated at 55° C. for 3 h, and it was cooled, diluted with water, aqueous layer was extracted with EtOAc, organic layer was combined, washed with brine, dried and concentrated to give 5a (200 mg).

(E)-Ethyl 4-(2-ethoxyvinyl)-2-(methylthio)-6-(3-(pyrimidin-2-yl)phenylamino)pyrimidine-5-carboxylate (5b)

To a solution of ethyl 4-chloro-2-(methylthio)-6-(3-(pyrimidin-2-yl)phenylamino)pyrimidine-5-carboxylate (200 mg, 0.5 mmol) in AcCN (4 mL) was added (E)-2-(2-ethoxyvinyl)-4,4,5,5-tetramethyl-1,3,2-dioxaborolane (200 mg, 1 mmol), Pd(OAc)2 (7 mg, 0.03 mmol) and SPhos (31 mg, 0.075 mmol), and a solution of K3PO4 (212 mg, 1 mmol) in water (1 mL). The mixture was heated at 90° C. for 15 h, cooled to room temperature, the resulting precipitate was collected by filtration to give 5b (188 mg).

Ethyl 2-(methylthio)-4-(2-oxoethyl)-6-(3-(pyrimidin-2-yl)phenylamino)pyrimidine-5-carboxylate (5c)

A solution of (E)-ethyl 4-(2-ethoxyvinyl)-2-(methylthio)-6-(3-(pyrimidin-2-yl)phenylamino)pyrimidine-5-carboxylate (188 mg) in TFA (2 mL) was stirred at room temperature for 2 h, then it was concentrated to dryness. DCM was added to dissolve the residue, and the organic layer was washed with Sat. NaHCO3, brine, dried and concentrated to give 5c (142 mg).

6-(4-methoxybenzyl)-2-(methylthio)-4-(3-(pyrimidin-2-yl)phenylamino)-7,8-dihydropyrido[4,3-d]pyrimidin-5(6H)-one (5d)

To a solution of ethyl 2-(methylthio)-4-(2-oxoethyl)-6-(3-(pyrimidin-2-yl)phenylamino)pyrimidine-5-carboxylate (142 mg, 0.35 mmol) in DCE (2.5 mL) was added PMBNH2 (55 mg, 0.40 mmol). After stirring for 30 min, it was added AcOH (38 mg) and NaB(OAc)3H (182 mg), and the mixture was further stirred at room temperature for 15 h. The mixture was then heated at 60° C. for 3 h, cooled and diluted with DCM, the organic layer was washed with Sat. NaHCO3, brine, dried and concentrated to give crude oil, which was purified by column chromatography (DCM/EtOAC=100:0 to 75:25) to give 5d (84 mg).

Tert-butyl (1S,2R)-2-(6-(4-methoxybenzyl)-5-oxo-4-(3-pyrimidin-2-yl)phenylamino)-5,6,7,8-tetrahydropyrido[4,3-d]pyrimidin-2-ylamino)cyclohexylcarbamate (5e)

To a solution of 6-(4-methoxybenzyl)-2-(methylthio)-4-(3-(pyrimidin-2-yl)phenylamino)-7,8-dihydropyrido[4,3-d]pyrimidin-5(6H)-one (84 mg, 0.174 mmol) in NMP (1.5 mL) was added mCPBA (46 mg, 0.174 mmol). After stirring at room temperature for 30 min, it was diluted with EtOAc, organic layer was washed with Sat. NaHCO3, brine, dried and concentrated to give a mixture of corresponding sulfoxide and sulfone. To a solution of this mixture of sulfoxide and sulfone in NMP (1.5 mL) was added tert-butyl (1S,2R)-2-aminocyclohexylcarbamate (44 mg, 0.2 mmol) and DIPEA (0.07 mL, 0.40 mmol). After heated at 70° C. for 3 h, the mixture was cooled and diluted with EtOAc, organic layer was washed with Sat. NaHCO3, brine, dried and concentrated to give as 5e crude product.

2-((1R,2S)-2-Aminocyclohexylamino)-4-(3-(pyrimidin-2-yl)phenylamino)-7,8-dihydropyrido[4,3-d]pyrimidin-5(6H)-one (4)

A solution of tert-butyl (1S,2R)-2-(6-(4-methoxybenzyl)-5-oxo-4-(3-(pyrimidin-2-yl)phenylamino)-5,6,7,8-tetrahydropyrido[4,3-d]pyrimidin-2-ylamino)cyclohexylcarbamate in TFA (1.5 mL) was heated at 90° C. for 3 h and 100° C. for 2 h, then it was cooled and concentrated to give crude oil, which was purified by preparative HPLC to give 4. MS found for $C_{23}H_{26}N_8O$ as $(M+H)^+$ 431.3, UV: $\lambda=253.4$.

Example 5

2-((1R,2S)-2-Aminocyclohexylamino)-4-(quinolin-6-ylamino)-7,8-dihydropyrido[4,3-d]pyrimidin-5(6H)-one. (Compound 5)

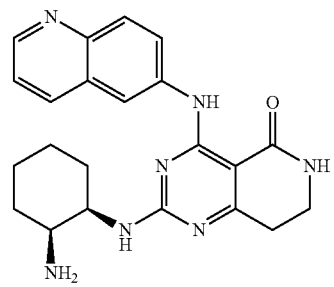 [SMILES: N[C@H]1CCCC[C@H]1Nc1nc2c(c(Nc3ccc4ncccc4c3)n1)C(=O)NCC2]

Figure 6:
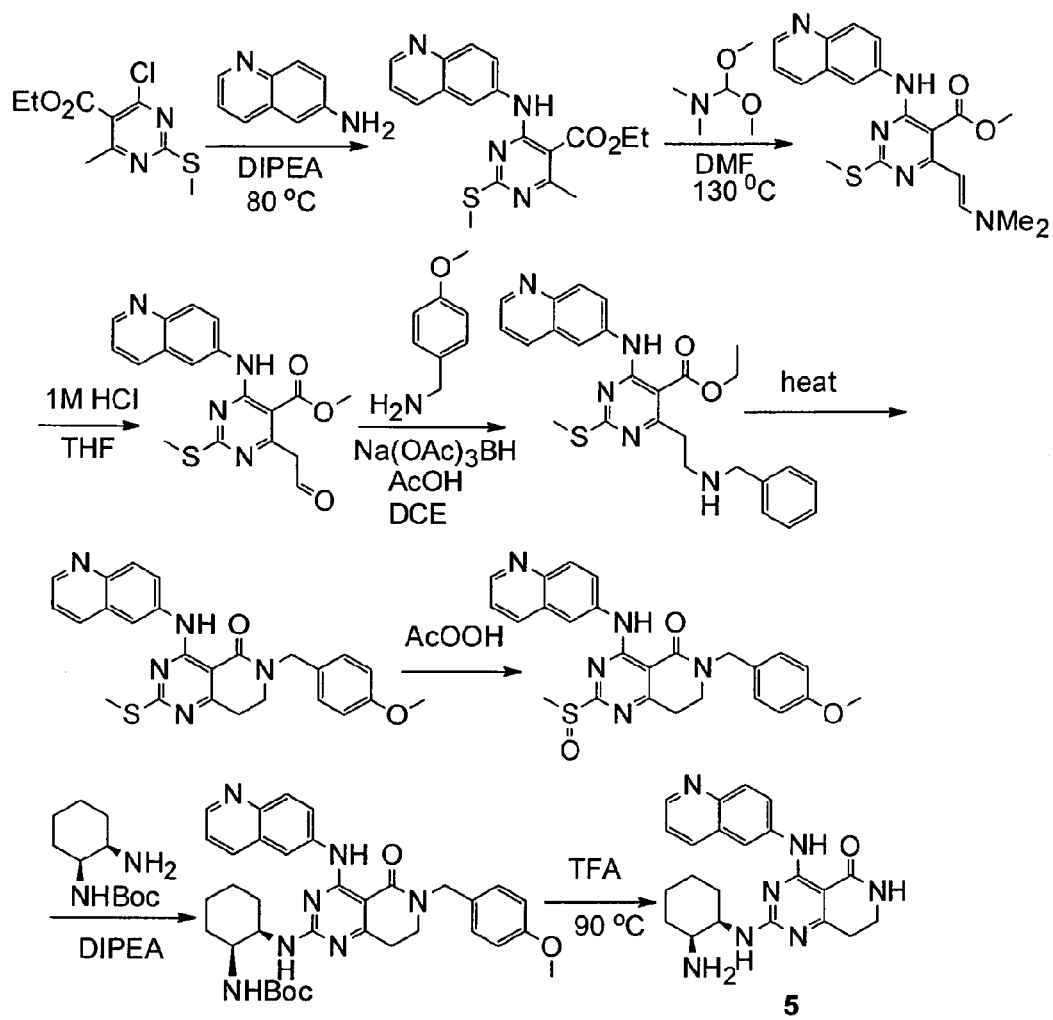
FIG. 6 shows a synthetic route for the preparation of 2-((1R,2S)-2-aminocyclohexylamino)-4-(quinolin-6-ylamino)-7,8-dihydropyrido[4,3-d]pyrimidin-5(6H)-one (5).

The title compound 5 was synthesized as shown in FIG. 6. MS found for $C_{22}H_{25}N_7O$ as $(M+H)^+$ 404.3, UV: $\lambda=215.7, 240.4, 280.7$.

Example 6

4-(3-(2H-1,2,3-Triazol-2-yl)phenylamino)-2-((1R,2S)-2-aminocyclohexylamino)-7,8-dihydropyrido[4,3-d]pyrimidin-5(6H)-one (6)

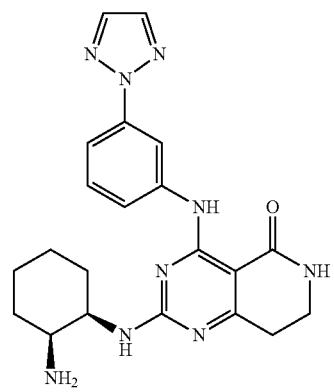 [SMILES: N[C@H]1CCCC[C@H]1Nc1nc2c(c(Nc3cccc(-n4nccn4)c3)n1)C(=O)NCC2]

Figure 7:
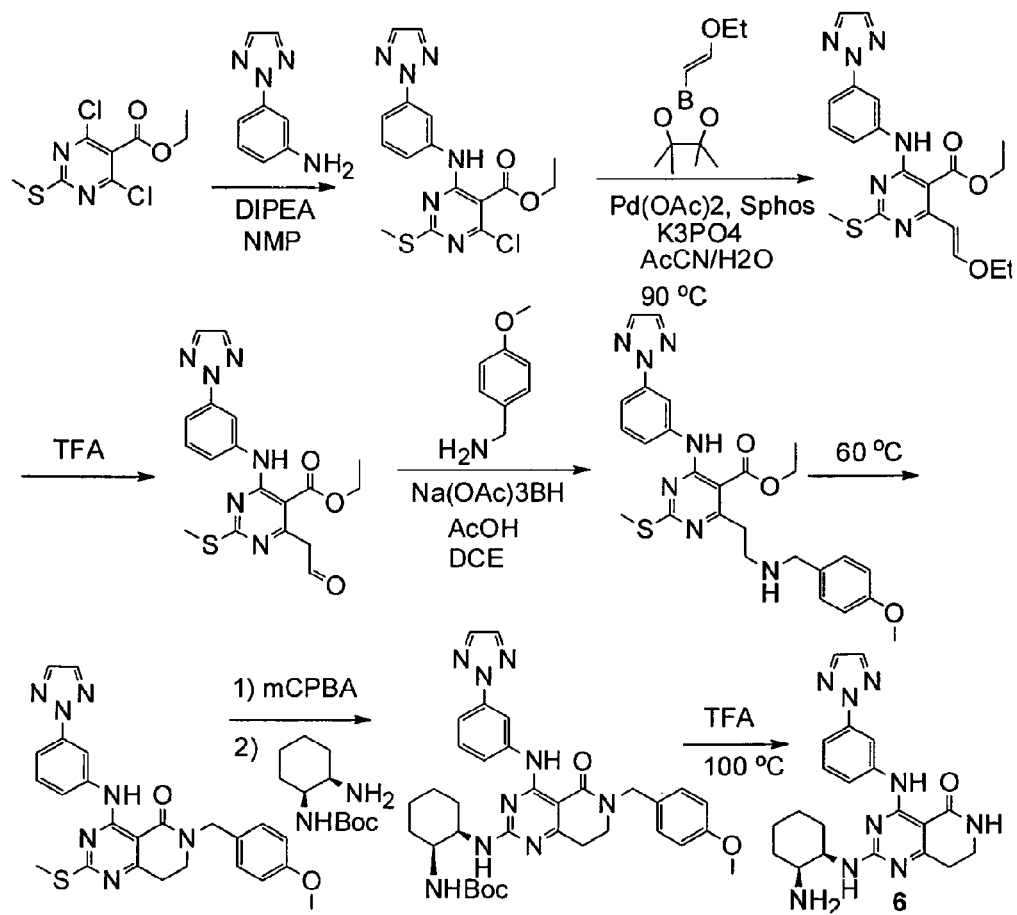
FIG. 7 shows a synthetic route for the preparation of 4-(3-(2H-1,2,3-triazol-2-yl)phenylamino)-2-((1R,2S)-2-aminocyclohexylamino)-7,8-dihydropyrido[4,3-d]pyrimidin-5(6H)-one (6).

The title compound 6 was synthesized as shown in FIG. 7. MS found for $C_{21}H_{25}N_9O$ as $(M+H)^+$ 420.3, UV: $\lambda=260.5$.

Example 7

2-((1R,2S)-2-Aminocyclohexylamino)-4-(4-methoxy-3-(trifluoromethyl)phenylamino)-7,8-dihydropyrido[4,3-d]pyrimidin-5(6H)-one (7)

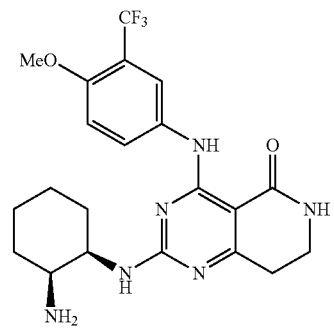 [SMILES: COc1ccc(Nc2nc(N[C@@H]3CCCC[C@@H]3N)nc3c2C(=O)NCC3)cc1C(F)(F)F]

Figure 8:
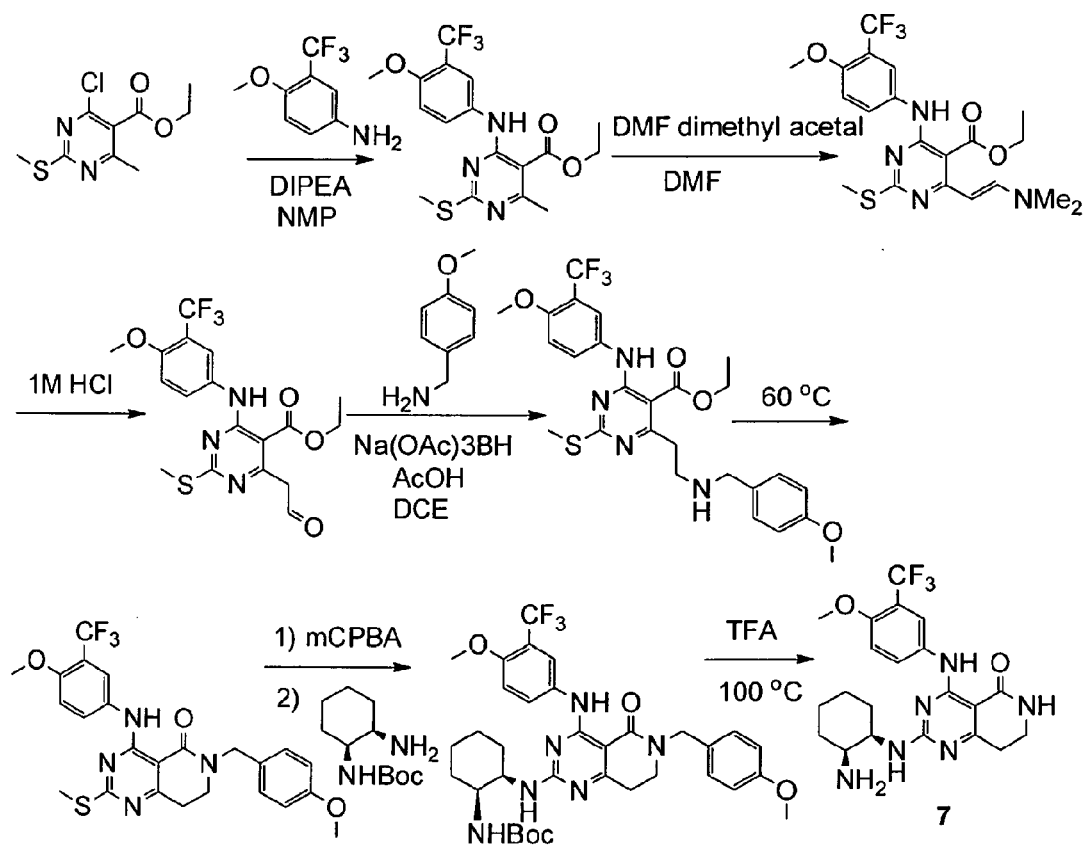
FIG. 8 shows a synthetic route for the preparation of 2-((1R,2S)-2-aminocyclohexylamino)-4-(4-methoxy-3-(trifluoromethyl)phenylamino)-7,8-dihydropyrido[4,3-d]pyrimidin-5(6H)-one (7).

The title compound 7 was synthesized as shown in FIG. 8. MS found for $C_{21}H_{25}F_3N_6O_2$ as $(M+H)^+$ 451.3, UV: λ=248.7, 292.6.

Example 8

Synthesis of 2-(cyclopentylamino)-4-(m-toly-lamino)-7,8-dihydropyrido[4,3-d]pyrimidin-5(6H)-one. (Compound 28)

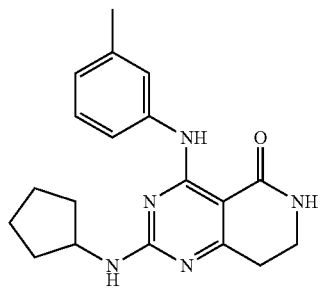 [SMILES: Cc1cccc(Nc2nc(NC3CCCC3)nc3c2C(=O)NCC3)c1]

The title compound was prepared according to the scheme shown below and using the procedure as described for example 2 where the sulfoxide/sulfone mixture was treated with cyclopentylamine.

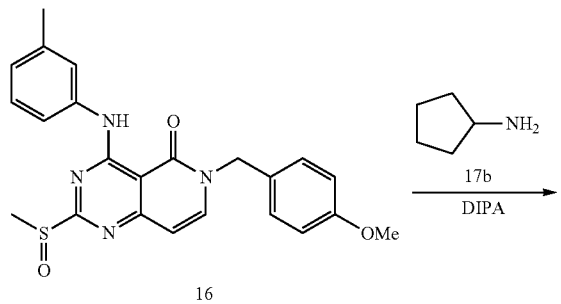
16

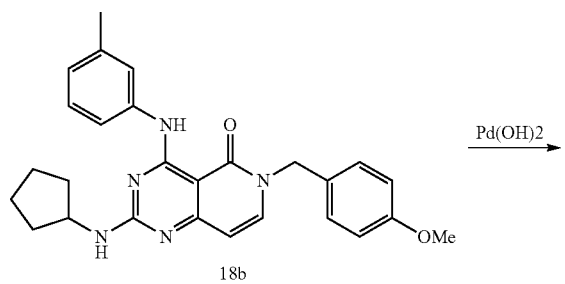
18b

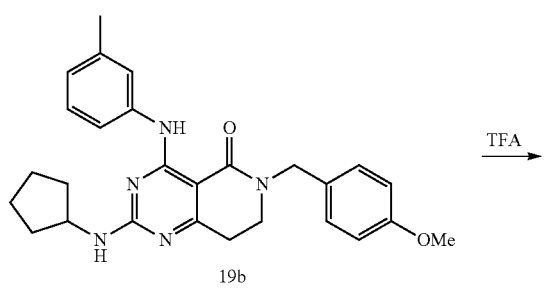
19b

-continued

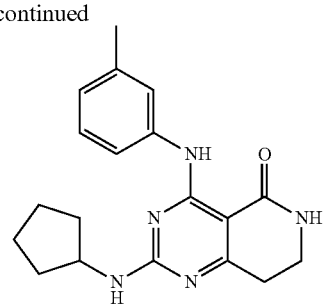

Example 9

Synthesis of 2((3-aminotetrahydro-2H-pyran-4-yl) amino)-4-(m-tolylamino)-7,8-dihydropyrido[4,3-d] pyrimidin-5(6H)-one (Compound 29)

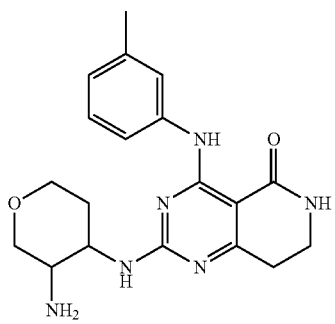 [SMILES: Cc1cccc(Nc2nc(NC3CCOCC3N)nc3c2C(=O)NCC3)c1]

The title compound was prepared according to the scheme below and using the procedure described in Example 2, where sulfoxide/sulfone was displaced with tetrahydropyran-diamine to afford the title compound. MS found 369.43 (M+H)

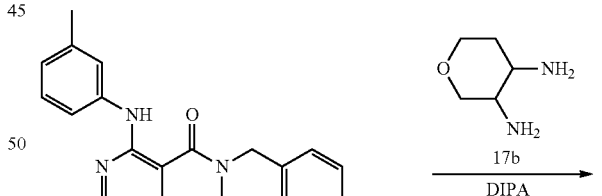
16

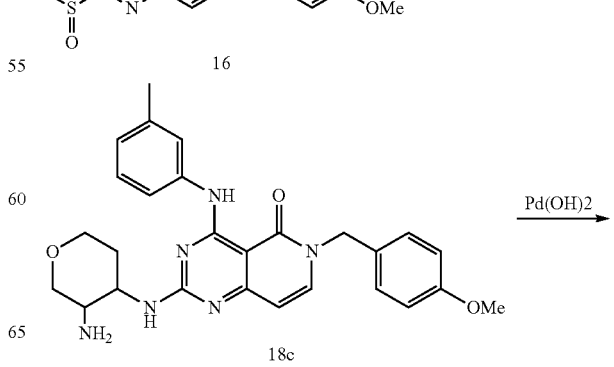
18c

-continued

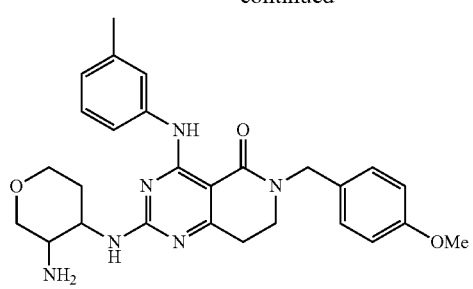

19c

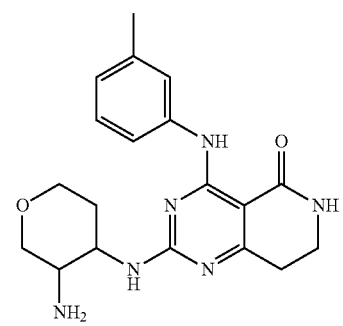

Example 10

Synthesis of 2-(cyclopropylamino)-4-(m-toly-lamino)-7,8-dihydropyrido[4,3-d]pyrimidin-5(6H)-one (Compound 30)

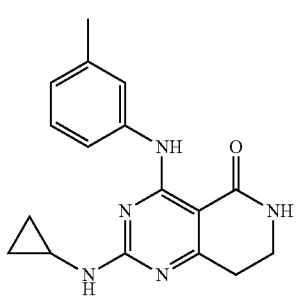 [SMILES: Cc1cccc(Nc2nc(NC3CC3)nc3c2C(=O)NCC3)c1]

The title compound was prepared according to the scheme below.

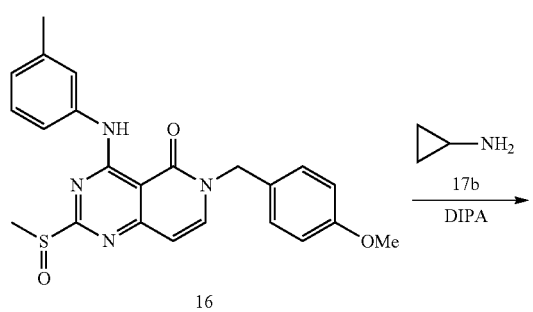

-continued

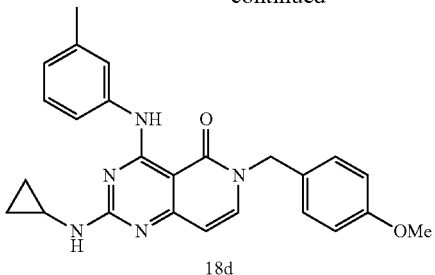

18d

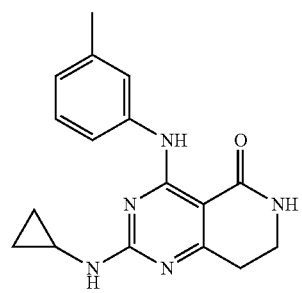

19d

The title compound was prepared using a procedure similar to the procedure of Example 2. MS found for $C_{17}H_{19}N_5O$ as $(M+H)^+$ 310.37.

Example 11

Synthesis of 2-(((1R,2S)-2-aminocyclohexyl)amino)-4-((6-morpholinopyridin-3-yl)amino)-7,8-dihydropyrido[4,3-d]pyrimidin-5(6H)-one

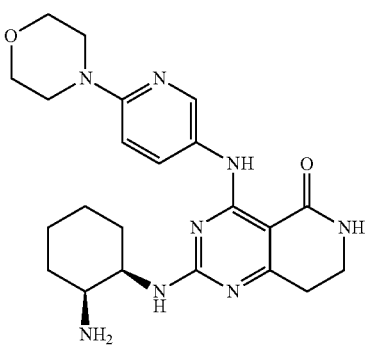 [SMILES: N[C@H]1CCCC[C@H]1Nc1nc2c(c(Nc3ccc(N4CCOCC4)nc3)n1)C(=O)NCC2]

The title compound was prepared according to the scheme below.

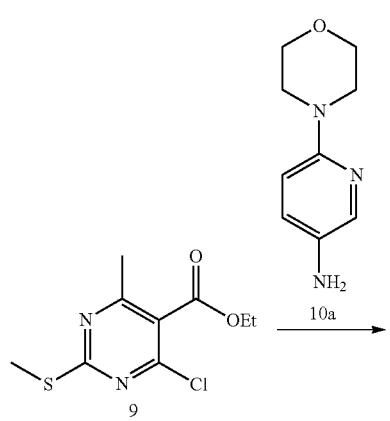
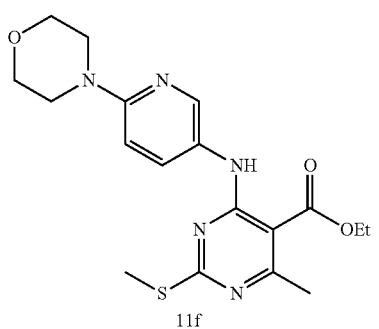
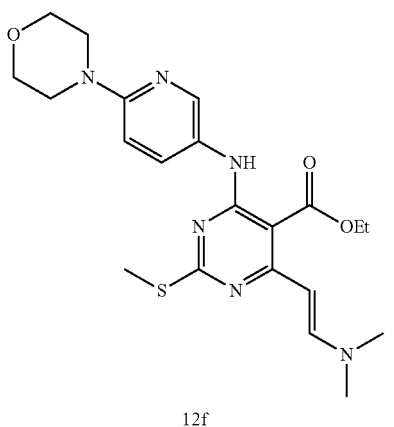
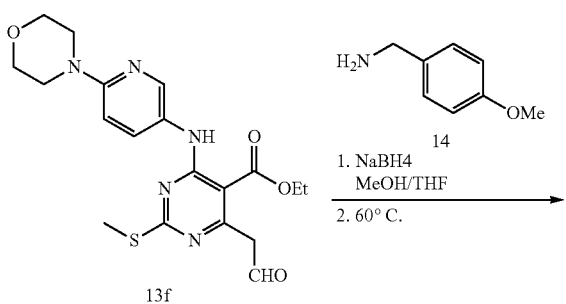
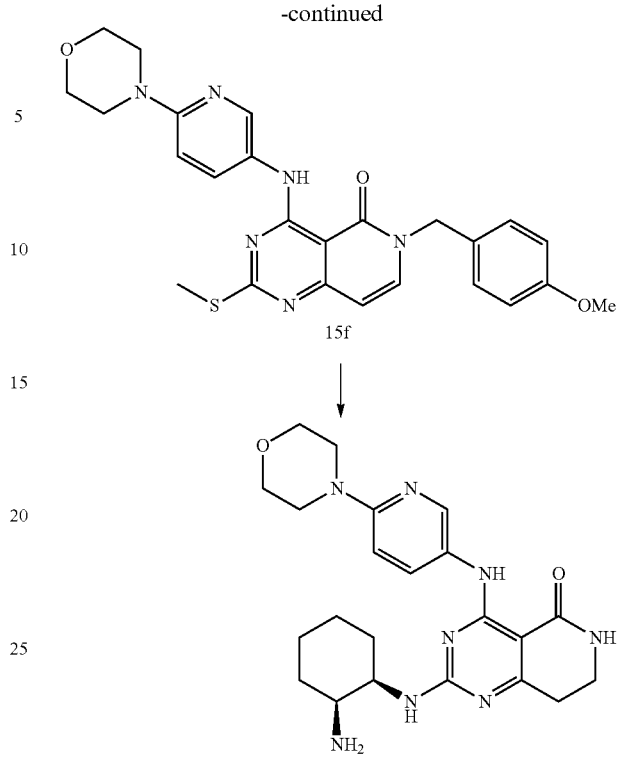

The title compound was synthesized as described for example 2 except where compound 9 is treated with 6-morpholinopyridin-3-amine and then followed by the same reaction sequence. MS found for $C_{22}H_{30}N_8O_2$ as $(M+H)^+$ 439.25.

Example 12

Synthesis of 2-(((1R,2S)-2-aminocyclohexyl)amino)-4-(4-morpholinophenyl)amino)-7,8-dihydropyrido[4,3-d]pyrimidin-5(6H)-one

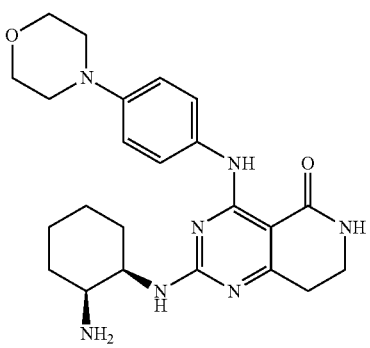

The title compound was prepared according to the scheme as described in Example 11 except where compound 9 is treated with 6-morpholinophenyl-4-amine and then followed by the same reaction sequence. MS found for $C_{23}H_{31}N_7O_2$ as $(M+H)^+$ 438.54.

One of skill in the art will appreciate that the compounds of Formula I can be made by still other methods known to one of skill in the art (see, for example, Comprehensive Organic Transformations Richard C. Larock, 1989).

Example 13

Synthesis of 6-(((1R,2S)-2-aminocyclohexyl)amino)-8-(m-tolylamino)-3,4-dihydroisoquinolin-1(2H)-one The title compound was prepared according to the scheme below.

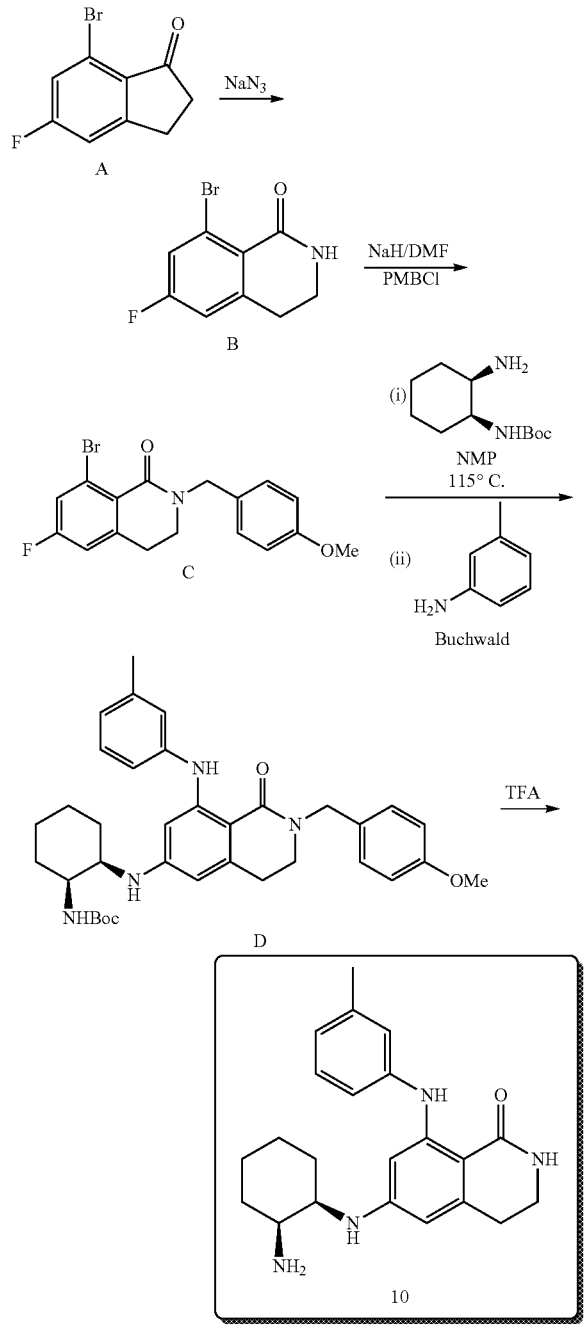

Compound 10 can also be synthesized according to the protocols described in the patents US2007/249607, US20J12/172448 & WO2010/105179A2.

Synthesis of 8-bromo-6-fluoro-3,4-dihydroisoquinolin-1(2H)-one (B)

Methanesulfonic acid (14.46 mL, 10 equiv) was added to a mixture of 7-bromo-5-fluoro-2,3-dihydro-1H-inden-1-one A (5 g, 21.93 mmol) in $CH_2Cl_2$ (40 mL) at 0° C. Sodium azide was added slowly in portions to this mixture. After the sodium azide addition was complete. The mixture was stirred for an additional 30 min, and an aqueous mixture of NaOH (20 wt %) was added until the mixture was slightly basic. The mixture was extracted with methylene chloride, and the combined organic layers were evaporated under reduced pressure. Purification of the mixture by flash column chromatography on silica gel provided the desired product B (3.25 g, 61%).

Synthesis of 8-bromo-6-fluoro-2-(4-methoxybenzyl)-3,4-dihydroisoquinolin-1(2H)-one (C)

NaH (0.74 g, 1.5 equiv) was added to a solution of the 8-bromo-6-fluoro-3,4-dihydroisoquinolin-1(2H)-one B (3 g, 12.34 mmol) in DMF (50 mL) at 0 C. The solution was stirred for 20 min, and PMBCl was added. The reaction mixture was warmed to RT and stirred for 1 h. Aqueous $NH_4Cl$ was added, the aqueous mixture was extracted with EtOAc, and the organic layer was separated. The volatile materials were evaporated under reduced pressure, and the residue was purified by flash column chromatography on silica gel to provide the desired product (3.27 g, 70%).

Synthesis of tert-butyl (1S,2R)-2-(2-(4-methoxybenzyl)-1-oxo-8-(m-tolylamino)-1,2,3,4-tetrahydroisoquinolin-6-ylamino)cyclohexylcarbamate (D)

8-bromo-6-fluoro-2-(4-methoxybenzyl)-3,4-dihydroisoquinolin-1(2H)-one C (0.7 g, 1.92 mmol), tert-butyl(1S,2R)-2-aminocyclohexylcarbamate (0.62 g, 2.91 mmol), DIPEA (0.5 mL, 2.91 mmol) and NMP (4 mL) were added to a tube. The tube was sealed and heated overnight at 115° C. After cooling, the reaction mixture was diluted with water and EtOAc. The aqueous layer was back-extracted with EtOAc (3×). The combined organic layers were then washed with $H_2O$, IN HCl (2×), saturated $NaHCO_3$, $H_2O$ and brine before drying with $Na_2SO_4$. The material was filtered and concentrated under reduced pressure to give 0.337 g of a crude oil. Purification of this material was not required. This 3,4-dihydroisoquinolin-1(2H)-one derivative (0.33 g, 0.592 mmol), m-toluidine (0.31 mL, 0.71 mmol) and $CS_2CO_3$ (0.577 g, 1.776 mmol) were added to a tube. The tube was evacuated and flushed with argon for three cycles. Toluene (3.6 mL) and NMP (2.2 mL) were then added and the mixture was degassed with argon for 30 minutes. $Pd_2(dba)_3$ (0.0011 g, 0.001184 mmol) and BINAP (0.0015 g, 0.002368 mmol) were then added, the tube was sealed and heated overnight at 100° C. After cooling, the mixture was diluted with water and EtOAc. The aqueous layer was back-extracted with EtOAc (3×). The combined organic layers were then washed with $H_2O$, IN HCl (2×), saturated $NaHCO_3$, $H_2O$ and brine before drying with $Na_2SO_4$. The material was filtered and concentrated under reduced pressure to give a crude oil. Purification of this material via flash chromatography (30 percent EtOAc/hexane) to yield in 0.27 g (24%) of compound D.

Synthesis of 6-((1R,2S)-2-aminocyclohexylamino)-8-(m-tolylamino)-3,4-dihydroisoquinolin-1(2H)-one A mixture of tert-butyl (1S,2R)-2-(2-(4-methoxybenzyl)-1-oxo-8-(m-tolylamino)-1,2,3,4-tetrahydroisoquinolin-6-ylamino)cyclohexylcarbamate D (130 mg, 0.222 mmol) and TFA (0.5 mL) was heated to 90° C. for 3 h. After completion of the reaction, the reaction mixture was evaporated under reduced pressure and the obtained crude residue was washed with isopropyl ether and dried to get Compound-10 as its TFA salt (55 mg, 68% Yield).

The following analogs were also prepared starting from compound-1 according to the experimental described for the preparation of Compound-10/Example-13.

| Compound | Structure | Name |
|---|---|---|
| 10 | 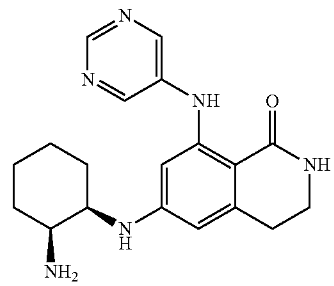 | 6-((1R,2S)-2-aminocyclohexylamino)-8-(pyrimidin-5-ylamino)-3,4-dihydroisoquinolin-1(2H)-one |
| 27 | 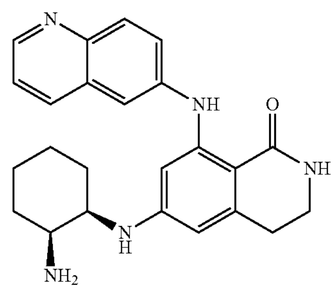 | 6-((1R,2S)-2-aminocyclohexylamino)-8-(quinolin-6-ylamino)-3,4-dihydroisoquinolin-1(2H)-one |
| 31 | 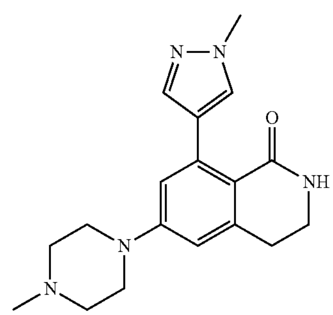 [SMILES: CN1CCN(c2cc3c(c(-c4cnn(C)c4)c2)C(=O)NCC3)CC1] | 8-(1-methyl-1H-pyrazol-4-yl)-6-(4-methylpiperazin-1-yl)-3,4-dihydroisoquinolin-1(2H)-one |
| 32 | 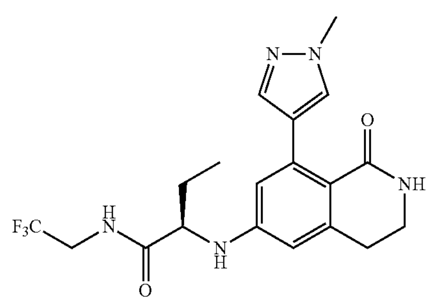 | (R)-2-(8-(1-methyl-1H-pyrazol-4-yl)-1-oxo-1,2,3,4-tetrahydroisoquinolin-6-ylamino)-N-(2,2,2-trifluoroethyl)butanamide |

-continued

| Compound | Structure | Name |
|---|---|---|
| 33 | 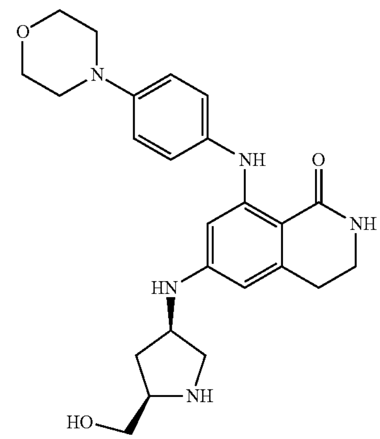 [SMILES: O=C1NCCc2cc(N[C@H]3CN[C@@H](CO)C3)cc(Nc3ccc(N4CCOCC4)cc3)c21] | 6-((3R,5R)-5-(hydroxymethyl)pyrrolidin-3-ylamino)-8-(4-morpholinophenylamino)-3,4-dihydroisoquinolin-1(2H)-one |

Example 14

Inhibition of Syk Tyrosine Phosphorylation Activity

The in vitro and in vivo human JAK/Syk activities of the inventive compounds can be determined by various procedures known in the art, such as a test for their ability to inhibit the activity of human plasma JAK/Syk. The potent affinities for human JAK/Syk inhibition exhibited by the inventive compounds can be measured by an $IC_{50}$ value (in nM). The $IC_{50}$ value is the concentration of the compound required to provide 50% inhibition of human JAK/Syk proteolytic activity. The smaller the $IC_{50}$ value, the more active (potent) is a compound for inhibiting Syk activity.

An in vitro assay for detecting and measuring inhibition activity against Syk is as follows.

SYK tyrosine phosphorylation activity is measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note—How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

Molecules are reconstituted in 30% DMSO and serially diluted 1:3 with the final dilution containing DMSO in the absence of the candidate molecule. The final DMSO concentration in the assay is 3%. Kinase assays are performed as a two part reaction. The first reaction is a kinase reaction which comprises a candidate molecule, full length active recombinant SYK enzyme (Millipore, Calif.), and biotin-DEEDYESP-OH, a biotin-labeled SYK-specific substrate. The second reaction involves termination of the kinase reaction and the simultaneous addition of the detection reagents—europium-labeled anti-phosphotyrosine reagent (Eu-W1024-PY100, Perkin Elmer, Boston, Mass.) and Streptavidin-Allophycocyanin detection reagent (SA-APC, Prozyme, CA). The kinase reaction is performed in a black U-bottom 96-well microtitre plate. The final reaction volume is 50 μL and contains a final concentration of 1 nM active SYK enzyme, 550 nM SYK-substrate, and 100 μM ATP diluted in a buffer containing 50 mM Tris pH 7.5, 5 mM $MgCl_2$, and 1 mM DTT. The reaction is allowed to proceed for 1 hour at room temperature. The quench buffer contains 100 mM Tris pH 7.5, 300 mM $NaCl_2$, 20 mM EDTA, 0.02% Brij35, and 0.5% BSA. The detection reagents are added to the reaction mixture at the following dilutions—1:500 for Eu-W1024-PY100 and 1:250 for SA-APC. The kinase reaction is terminated by the addition of 50 μL quench buffer containing the detection reagents. The detection is allowed to proceed for 1 hr at room temperature. Detection of the phosphorylated substrate in the absence and presence of inhibitors is measured in the TR-FRET instrument, Analyst HT (Molecular Probes, Sunnyvale, Calif.) and the condition for measurements are set using CriterionHost Release 2.0 (Molecular Probes, Sunnyvale, Calif.). The settings used are as follows: excitation 360 nm, emission 665—7.5 nm, beam splitter 350 nm 50/50, flash 100 pulses, delay 60 us, integration 400 us, z-height 2 mm. Inhibition of SYK-tyrosine kinase activity is calculated as the maximum response observed in the presence of inhibitor, compared to that in the absence of inhibitor. $IC_{50}$ values are derived by non-linear regression analysis.

$IC_{50}$ data for compounds of the present invention was obtained using the assay described above, as outlined in Table 2.

TABLE 2

Kinase Inhibitor $IC_{50}$ Data

| EXAMPLE NO. | $IC_{50}$ (nM)[a] |
|---|---|
| 1 | +++ |
| 4 | ++ |
| 6 | +++ |
| 7 | + |

[a]Measured $IC_{50}$ values: +++ ≤100 nM; ++ ≤250 nM; + >250 nM.

Intracellular phospho-flow cytometry can be used to test compound inhibition of Syk activity in the non-Hodgkin's lymphoma cell line Ramos. $1 \times 10^6$ cells in log phase growth were aliqoted; Syk kinase is activated by incubating cells for 10 minutes with 3 μg/ml antibody specific to the B cell receptor. Directly following, cells are fixed in 1% paraformaldehyde for 5 minutes at room temperature, washed in phosphate buffered saline, and then permeablized by incubation for 2 hours in ice cold methanol. Cells are again washed in phosphate buffered saline, then incubated for 30 minutes with antibody specific for phosphorylated Erk (Y204), which are indicators of Syk kinase activity. All antibodies used are purchased from BD Pharmingen (San Jose, Calif.). After incubation with antibodies, cells are again washed and subjected to flow cytometry.

Syk has been implicated experimentally in B cell development, proliferation, and survival. Moreover, Syk is implicated as an oncogene. Expression of constitutively active Syk in adoptively transferred bone marrow cells induces leukemia in mice, and over-activity of Syk is associated with a variety of lymphomas in humans Given the role of Syk in B cell biology, its selective inhibition may be sufficient to provide clinical benefit in B cell proliferative disorders, while reducing toxicities that may arise due to suppression of other off-target kinases.

The anti-proliferative effects of compounds on non-Hodgkin's lymphoma B cell lines SUDHL-4, SUDHL-6, and Toledo can also assessed. SUDHL-4 and SUDHL-6 require B cell receptor signaling for growth and survival, while the Toledo cell line (serving here as a negative control) does not. Cells are aliquoted into each well of a 96-well plate and incubated with increasing concentrations of compound for 72 hours, after which cell survival and proliferation is determined using the MTT assay (Chemicon International, Inc., Temecula, Calif.) following protocols supplied by the manufacturer.

Induction of apoptosis in non-Hodgkin's lymphoma B cell lines SUDHL-4, SUDHL-6, and Toledo is assessed by measuring the apoptotis marker Caspase 3. Cells were incubated with 1, 3, or 10 µM compound for 24, 48, and 72 hours. At the conclusion of each time point, cells are processed for flow cytometry analysis using the Monoclonal Rabbit Anti-Active Caspase-3 Antibody Kit and related protocols (BD Pharmingen).

Syk activity is not only required for B cell signaling, proliferation, and survival, as shown, but is also critical for cellular activation upon cross-linking of the B cell receptor. B cell activation leads to increased cell surface expression of several proteins involved in cell signaling, antigen presentation, and adhesion. Among these, CD80, CD86, and CD69 are commonly measured to determine B cell activation status. Primary mouse B cells isolated from spleen can be aliquoted and incubated with increasing concentrations of compound (0.05 to 20M) in the presence of goat anti-mouse IgD (eBiosciences, Inc., San Diego, Calif.) for 20 hours to cross-link the B cell receptor. Cells are washed and incubated for 30 minutes on ice with antibodies specific for the CD80, CD86, and CD69 B cell activation markers. B cells are identified from the pooled population by staining with the B cell marker CD45RO. All antibodies are purchased from BD Pharmingen.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound of Formula (I):

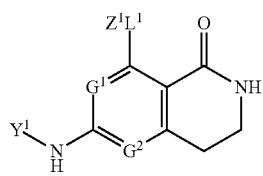

(I)

or a tautomer or a pharmaceutically acceptable salt thereof, wherein
$G^1$ is N and $G^2$ is N
$L^1$ is selected from the group consisting of a bond, NH, O, and S;
$Z^1$ is selected from the group consisting of aryl and heteroaryl, wherein the aryl and heteroaryl are optionally substituted with 1 to 5 $R^1$;
$R^1$ is independently selected from the group consisting of halo, $C_{1-8}$alkyl, $C_{2-8}$alkenyl, haloC$_{1-8}$alkyl, $(CH_2)_nSR^{1a}$, $(CH_2)_nOR^{1a}$, $O(CH_2)_nOR^{1a}$, $(CH_2)_nNR^{1b}R^{1c}$, $(CH_2)_nCOR^{1e}$, $(CH_2)_nCONR^{1b}R^{1c}$, $(CH_2)_nNR^{1b}COR^{1e}$, $(CH_2)_nCONR^{1b}(OR^{1a})$, $(CH_2)_nCO_2R^{1a}$, $O(CH_2)_nCO_2R^{1a}$, $(CH_2)_nNR^{1b}CO_2R^{1a}$, $(CH)_nSO_2NR^{1b}R^{1c}$, $(CH_2)_nNR^{1b}SO_2R^{1e}$, $(CH_2)_nSOR^{1e}$, $(CH_2)_nSO_2R^{1e}$, oxo, $(CH_2)_nCN$, $N_3$, $NO_2$, and -$L^2$-W, where n is 0, 1, 2, 3, 4, 5, or 6 and j is 1, 2, 3, 4, 5, or 6;
$L^2$ is selected from the group consisting of
—O(CH$_2$)$_b$—, —SO—, —SO$_2$—, —CO—, —NR$^{1d}$—, —CONR$^{1d}$(CH$_2$)$_b$—, —NR$^{1d}$CO—NR$^{1d}$SO$_2$—, —SO$_2$NR$^{1d}$—, a bond, and —(CH$_2$)$_e$— where b is 0, 1, 2, 3, 4, or 5 and e is 1, 2, 3, 4, or 5;
W is selected from the group consisting of aryl, heteroaryl, cycloalkyl, and heterocyclyl each optionally substituted with 1 to 3 $R^2$;
$R^2$ is independently selected from the group consisting of halo, $C_{1-8}$alkyl, $C_{2-8}$alkenyl, haloC$_{1-8}$alkyl, $(CH_2)_mSR^{2a}$, $(CH_2)_mOR^{2a}$, $O(CH_2)_kOR^{2a}$, $(CH_2)_mNR^{2b}R^{2c}$, $(CH_2)$—COR$^{2e}$, $(CH_2)_mCONR^{2b}R^{2c}$, $(CH_2)_mNR^{2b}COR^{2e}$, $(CH_2)_mCONR^{2b}(OR^{2a})$, $(CH_2)_mCO_2R^{2a}$, $O(CH_2)_mCO_2R^{2a}$, $(CH_2)_mNR^{2b}CO_2R^{2a}$, $(CH)_mSO_2NR^{2b}R^{2c}$, $(CH_2)_mNR^{2b}SO_2R^{2e}$, $(CH_2)_mSOR^{2e}$, $(CH_2)_mSO_2R^{2e}$, oxo, $(CH_2)_mCN$, $N_3$, and $NO_2$, where m is 0, 1, 2, 3, 4, 5, or 6 and k is 1, 2, 3, 4, 5, or 6;
$R^{1a}$, $R^{1b}$, $R^{1c}$, $R^{1d}$, $R^{2a}$, $R^{2b}$, and $R^{2c}$ are independently selected from the group consisting of H, $C_{1-8}$alkyl, $C_{2-8}$alkenyl, and haloC$_{1-8}$alkyl;
$R^{1e}$ and $R^{2e}$ are independently selected from the group consisting of $C_{1-8}$alkyl, $C_{2-8}$alkenyl, and haloC$_{1-8}$alkyl;
$Y_1$ is

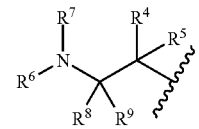

or $(CH_2)_v(Y^2)$, wherein
v is 0, 1, 2, or 3;
$Y^2$ is selected from the group consisting of $CH_2CH_3$, $(CH_2)_3NH_2$, cycloalkyl, heterocyclyl, aryl, and heteroaryl, wherein the cycloalkyl, heterocyclyl, aryl, and heteroaryl are optionally substituted with 1 to 3 $R^{10}$;
$R^4$ is selected from the group consisting of H, halo, $C_{1-8}$alkyl, $C_{2-8}$alkenyl, haloC$_{1-8}$alkyl, $(CH_2)_pSR^{4a}$, $(CH_2)_pSOR^{4a}$, $(CH_2)_pSO_2R^{4a}$, $(CH_2)_pOR^{4a}$, $(CH_2)_pNR^{4b}R^{4c}$, $(CH_2)_fCONR^{4b}R^{4c}$, $(CH_2)_pNR^{4b}COR^{4d}$, $(CH_2)_fCO_2R^{4a}$, $(CH_2)_pNR^{4b}CO_2R^{4a}$, $(CH_2)_f$cycloalkyl, $(CH_2)_p(O)$cycloalkyl, $(CH_2)_p(S)$cycloalkyl, $(CH_2)_pSO_2NR^{4b}R^{4c}$, $(CH_2)_pNH$cycloalkyl, $(CH_2)_f$CN, $(CH_2)_f$(aryl), $(CH_2)_f$(heteroaryl), $(CH_2)_f$(aryl)(heteroaryl), $(CH_2)_f$(heterocyclyl), $(CH_2)_p(O)(CH_2)_f$(aryl), $(CH_2)_p(O)(CH_2)_f$(heteroaryl), $(CH_2)_p(O)$ (CH$_2$)$_f$C$_{3-8}$cycloalkyl, and (CH$_2$)$_p$(O)(CH$_2$)$_f$ (heterocyclyl), where the aryl, heteroaryl, cycloalkyl, and heterocyclyl are each optionally substituted with 1 to 3 R$^{11a}$, f is 0, 1, 2, 3, 4, 5, or 6, and p is 1, 2, 3, 4, 5, or 6; or R$^4$ and R$^5$ together form =O or a 3 to 8 membered carbocyclic or heterocyclic ring optionally substituted with 1 to 3 R$^{11a}$;

R$^5$ is selected from the group consisting of H and C$_{1-8}$alkyl; or R$^5$ is joined to the adjacent nitrogen atom to form a 4 to 6 membered heterocyclic ring optionally substituted with 1 to 3 R$^{11a}$;

R$^6$ is selected from the group consisting of H, C$_{1-8}$alkyl, OH, O(C$_{1-8}$alkyl), CO$_2$R$^{6a}$, CO(NR$^{6a}$R$^{6b}$), and C$_{3-8}$cycloalkyl; or R$^6$ together with R$^7$ and the atoms to which they are attached to form a heterocyclyl ring optionally substituted with 1 to 3 R$^{11b}$;

R$^7$ is selected from the group consisting of H, C$_{1-8}$alkyl, and cycloalkyl;

R$^8$ is selected from the group consisting of H, C$_{1-8}$alkyl, (CH$_2$)—NR$^{8b}$R$^{8c}$, (CH$_2$)$_g$CONR$^{8b}$R$^{8c}$, (CH$_2$)$_g$CO(CH$_2$)$_u$NR$^{8b}$R$^{8c}$, (CH$_2$)$_g$CO$_2$R$^{8a}$, (CH$_2$)$_u$OR$^{8a}$, CH(C$_{1-8}$alkyl)OR$^{8a}$, (CH$_2$)$_g$cycloalkyl, (CH$_2$)$_g$heterocyclyl, (CH$_2$)$_g$aryl, (CH$_2$)$_g$heteroaryl, and (CH$_2$)$_u$(O)(aryl), where the aryl, cycloalkyl, heteroaryl, and heterocyclyl are each optionally substituted with 1 to 3 R$^{11c}$, g is 0, 1, 2, 3, 4, 5, or 6 and u is 1, 2, 3, 4, 5, or 6; or R$^8$ together with R$^9$ and the atoms to which they are attached to form =O, =S, or a cycloalkyl or heterocyclyl ring optionally substituted with R$^{11c}$;

R$^9$ is H or C$_{1-8}$alkyl;

R$^{10}$ is independently selected from the group consisting of halo, C$_{1-8}$alkyl, C$_{2-8}$alkenyl, haloC$_{1-8}$alkyl, (CH$_2$)$_q$SR$^{10a}$, (CH$_2$)$_q$OR$^{10a}$, (CH$_2$)$_q$NR$^{10b}$R$^{10a}$, (CH$_2$)$_q$COR$^{10d}$, (CH$_2$)$_q$CONR$^{10b}$R$^{10c}$, (CH$_2$)$_q$NR$^{10b}$COR$^{10d}$, (CH$_2$)$_q$CONR$^{10b}$(OR$^{10a}$), (CH$_2$)$_q$CO$_2$R$^{10a}$, O(CH$_2$)$_q$CO$_2$R$^{10a}$, (CH$_2$)$_q$NR$^{10b}$CO$_2$R$^{10a}$, (CH)$_q$SO$_2$NR$^{10b}$R$^{10a}$, (CH$_2$)$_q$NR$^{10b}$SO$_2$R$^{10d}$, (CH$_2$)$_q$SOR$^{10d}$, (CH$_2$)$_q$SO$_2$R$^{10d}$, OXO, (CH$_2$)$_q$CN, N$_3$, N=CH$_2$, NO$_2$, C(O)heterocyclyl, aryl, heteroaryl, cycloalkyl, and heterocyclyl, where the aryl, cycloalkyl, heteroaryl, and heterocyclyl are each optionally substituted with 1 to 3 R$^{11d}$ and q is 0, 1, 2, 3, 4, 5, or 6;

R$^{11a}$, R$^{11b}$, R$^{11c}$, and R$^{11d}$ are independently selected from the group consisting of halo, C$_{1-8}$alkyl, haloC$_{1-8}$alkyl, OH, C$_{1-8}$alkoxy, haloC$_{1-8}$alkoxy, C(O)C$_{1-8}$alkyl, CO$_2$C$_{1-8}$alkyl, and SO$_2$C$_{1-8}$alkyl;

R$^{4a}$, R$^{4b}$, R$^{4c}$, R$^{6a}$, R$^{6b}$, R$^{8a}$, R$^{8b}$, R$^{8c}$, R$^{10a}$, R$^{10b}$, and R$^{10c}$ are independently selected from the group consisting of H, C$_{1-8}$alkyl, C$_{2-8}$alkenyl, and haloC$_{1-8}$alkyl;

R$^{4d}$ and R$^{10d}$ are independently selected from the group consisting of C$_{1-8}$alkyl, C$_{2-8}$alkenyl, and haloC$_{1-8}$alkyl; and the wavy line indicates the point of attachment to the rest of the molecule.

2. A compound of claim 1 or a tautomer or a pharmaceutically acceptable salt thereof, wherein Z$^1$ is a five-membered heteroaryl ring optionally substituted with 1 to 3 R$^1$.

3. A compound of claim 2 or a tautomer or a pharmaceutically acceptable salt thereof, wherein Z$^1$ is selected from the group consisting of

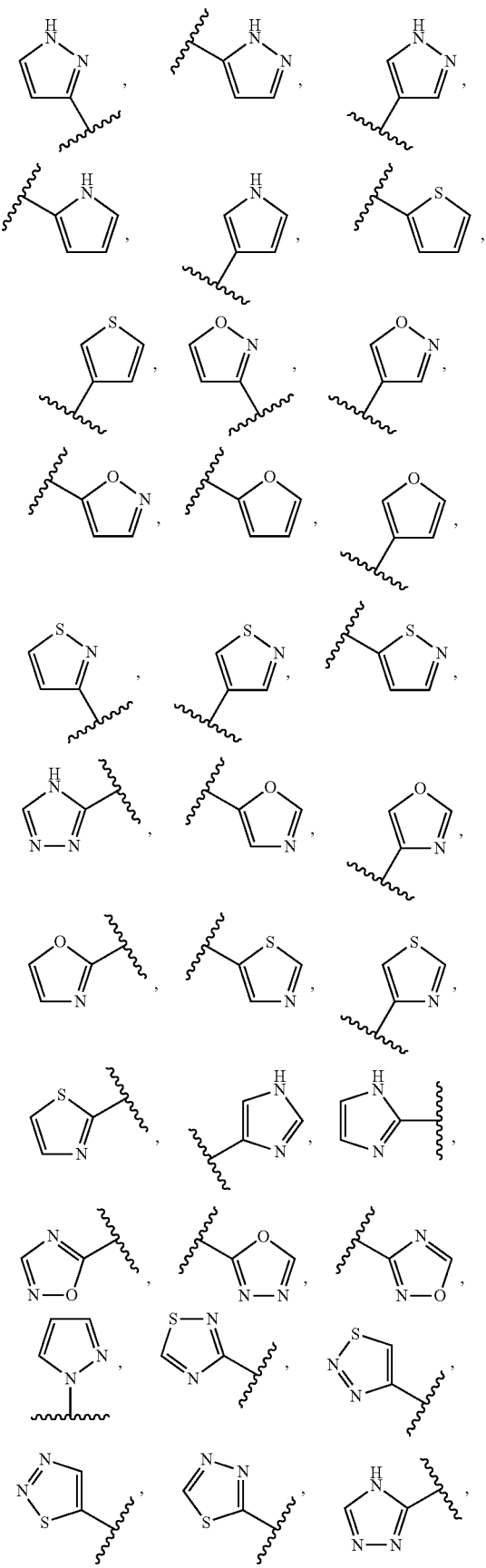

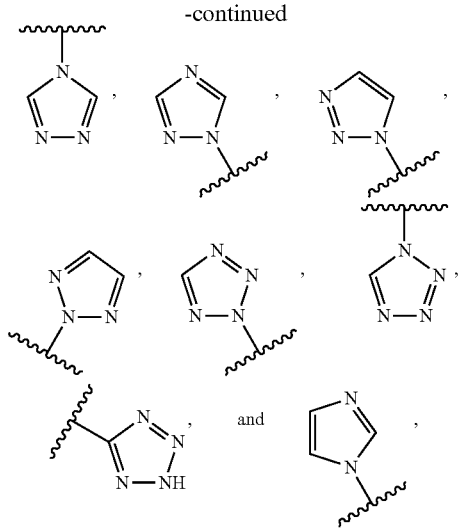

and wherein $Z^1$ is optionally substituted with 1 to 3 $R^1$.

4. A compound of claim 1, wherein at least one $R^1$ is $C_{1-3}$ alkyl.

5. A compound of claim 1 having Formula (II)

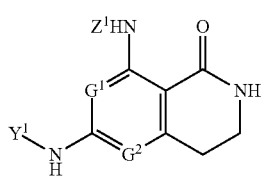

(II)

or a tautomer or a pharmaceutically acceptable salt thereof.

6. A compound of claim 5, or a tautomer or a pharmaceutically acceptable salt thereof, wherein $Z^1$ is selected from the group consisting of:

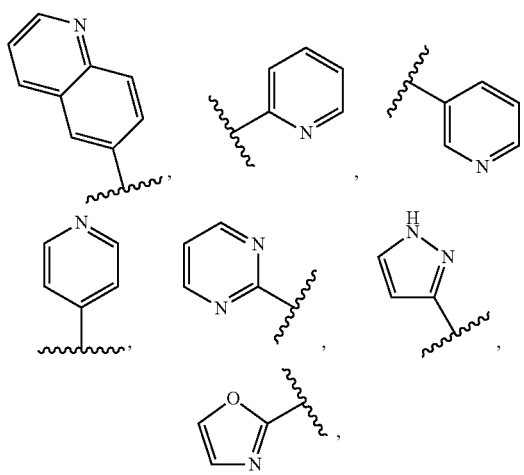

and phenyl;
and wherein $Z^1$ is optionally substituted with 1 to 3 $R^1$.

7. A compound of claim 5 or a tautomer or a pharmaceutically acceptable salt thereof wherein $Z^1$ is phenyl substituted with 1 to 5 $R^1$.

8. A compound of claim 7 or a tautomer or a pharmaceutically acceptable salt thereof wherein at least one of $R^1$ is selected from the group consisting of halo, $C_{1-8}$alkyl, cyano, and halo$C_{1-8}$alkoxy.

9. A compound of claim 5 of Formula (IIa)

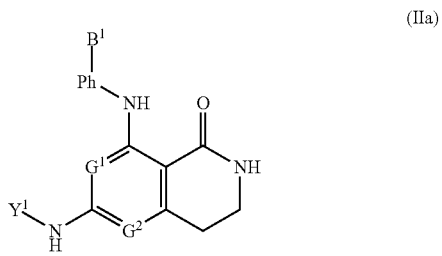

(IIa)

or a tautomer or a pharmaceutically acceptable salt thereof wherein
Ph is phenylene optionally substituted with 1 to 3 $R^1$;
$B^1$ is selected from the group consisting of CO—$NR^aR^b$, phenyl, heteroaryl, and heterocyclyl, wherein the phenyl, heteroaryl, and heterocyclyl are each optionally substituted with 1 to 3 $R^2$, and $R^a$ and $R^b$ together form a four to six membered heterocyclic ring optionally substituted with one to three groups independently selected from halo, $C_{1-8}$alkyl, and halo$C_{1-8}$alkyl.

10. A compound of claim 9 or a tautomer or a pharmaceutically acceptable salt thereof wherein $B^1$ is heteroaryl or heterocyclyl, each optionally substituted with 1 to 3 $R^2$.

11. A compound of claim 9 or a tautomer or a pharmaceutically acceptable salt thereof, wherein $B^1$ is selected from the group consisting of

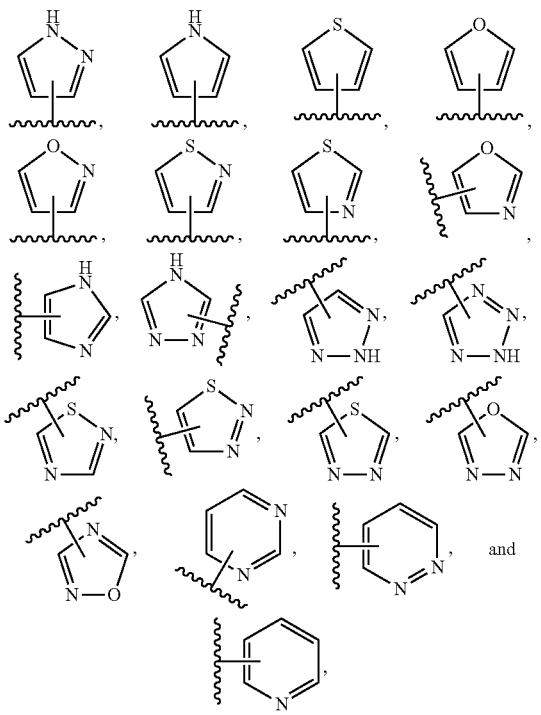

where the wavy line indicates the point of attachment to the rest of the molecule and wherein $B^1$ is optionally substituted with 1 to 3 $R^2$.

12. A compound of claim 1 or a tautomer or a pharmaceutically acceptable salt thereof wherein $L^1$ is a bond, and $Z^1$ is selected from the group consisting of:

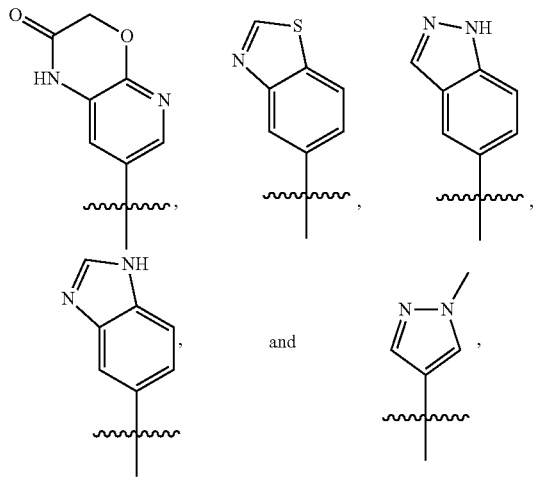

where the wavy line indicates the point of attachment to the rest of the molecule.

13. A compound of claim 1 or a tautomer or a pharmaceutically acceptable salt thereof, wherein $Y^1$ is $(CH_2)_v(Y^2)$ wherein v is 0 and $Y^2$ is cycloalkyl or heterocycloalkyl each optionally substituted with 1 to 3 $R^{10}$.

14. A compound of claim 13 or a tautomer or a pharmaceutically acceptable salt thereof, wherein $Y^2$ is tetrahydropyranyl, cyclopropyl, cyclobutyl, cyclopentyl or cyclohexyl, each optionally substituted with 1 to 3 $R^{10}$.

15. A compound of claim 13 or a tautomer or a pharmaceutically acceptable salt thereof, wherein $Y^1$ is

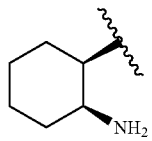

optionally substituted with 1 to 2 halo and where the wavy line indicates the point of attachment to the rest of the molecule.

16. A compound or a tautomer or a pharmaceutically acceptable salt thereof selected from the group consisting of:

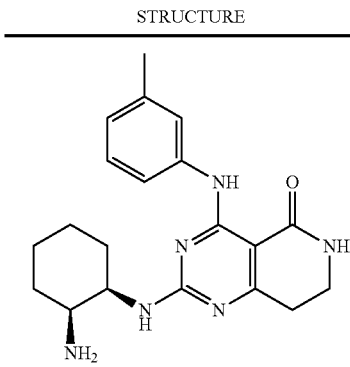

| STRUCTURE | NAME |
|---|---|
| | 2-(((1R,2S)-2-aminocyclohexyl)amino)-4-(m-tolylamino)-7,8-dihydropyrido[4,3-d]pyrimidin-5(6H)-one |
| 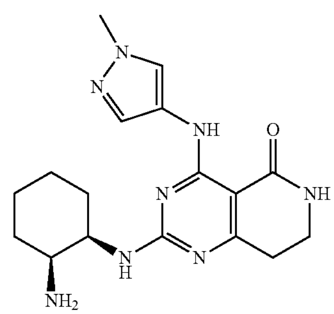 [SMILES: Cn1cc(Nc2nc(N[C@@H]3CCCC[C@@H]3N)nc3c2C(=O)NCC3)cn1] | 2-(((1R,2S)-2-aminocyclohexyl)amino)-4-((1-methyl-1H-pyrazol-4-yl)amino)-7,8-dihydropyrido[4,3-d]pyrimidin-5(6H)-one |
| 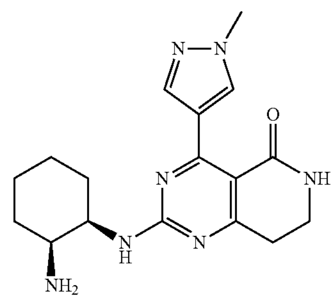 [SMILES: Cn1cc(-c2nc(N[C@@H]3CCCC[C@@H]3N)nc3c2C(=O)NCC3)cn1] | 2-(((1R,2S)-2-aminocyclohexyl)amino)-4-(1-methyl-1H-pyrazol-4-yl)-7,8-dihydropyrido[4,3-d]pyrimidin-5(6H)-one |
| 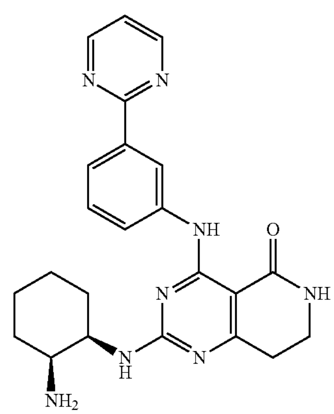 [SMILES: N[C@H]1CCCC[C@H]1Nc1nc2c(c(Nc3cccc(-c4ncccn4)c3)n1)C(=O)NCC2] | 2-(((1R,2S)-2-aminocyclohexyl)amino)-4-((3-(pyrimidin-2-yl)phenyl)amino)-7,8-dihydropyrido[4,3-d]pyrimidin-5(6H)-one |
| 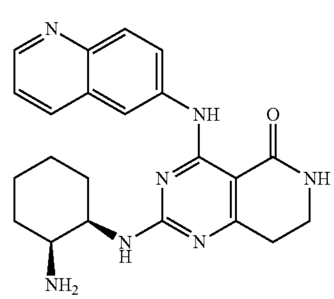 [SMILES: N[C@H]1CCCC[C@H]1Nc1nc2c(c(Nc3ccc4ncccc4c3)n1)C(=O)NCC2] | 2-(((1R,2S)-2-aminocyclohexyl)amino)-4-(quinolin-6-ylamino)-7,8-dihydropyrido[4,3-d]pyrimidin-5(6H)-one |

-continued

| STRUCTURE | NAME |
|---|---|
| 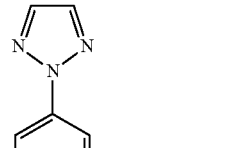 | 4-((3-(2H-1,2,3-triazol-2-yl)phenyl)amino)-2-(((1R,2S)-2-aminocyclohexyl)amino)-7,8-dihydropyrido[4,3-d]pyrimidin-5(6H)-one |
| 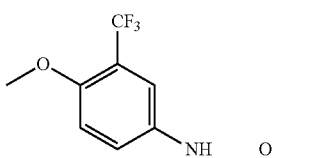 | 2-(((1R,2S)-2-aminocyclohexyl)amino)-4-((4-methoxy-3-(trifluoromethyl)phenyl)amino)-7,8-dihydropyrido[4,3-d]pyrimidin-5(6H)-one |
| 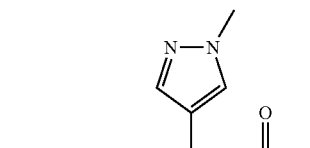 | 2-(((1R,2S)-2-aminocyclohexyl)amino)-4-(1-methyl-1H-pyrazol-4-yl)-7,8-dihydropyrido[4,3-d]pyrimidin-5(6H)-one |

-continued

| STRUCTURE | NAME |
|---|---|
| 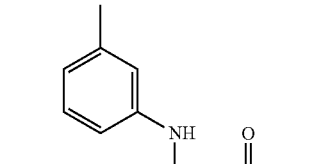 | 2-(cyclopentylamino)-4-(m-tolylamino)-7,8-dihydropyrido[4,3-d]pyrimidin-5(6H)-one |
| 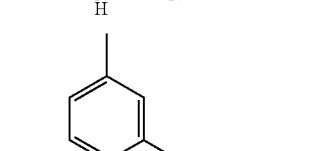 | 2-((3-aminotetrahydro-2H-pyran-4-yl)amino)-4-(m-tolylamino)-7,8-dihydropyrido[4,3-d]pyrimidin-5(6H)-one |
| 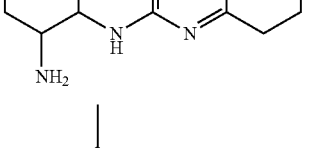 | 2-(cyclopropylamino)-4-(m-tolylamino)-7,8-dihydropyrido[4,3-d]pyrimidin-5(6H)-one. |

17. A pharmaceutical composition comprising a compound of claim 1 or a tautomer or a pharmaceutically acceptable salt thereof in combination with a pharmaceutically acceptable carrier or excipient.

18. A method for inhibiting Syk or JAK kinase or a signal transduction pathway mediated at least in part by Syk kinase activity comprising contacting a cell with a compound of claim 1.

* * * * *